US010357762B2

(12) United States Patent
Rogers et al.

(10) Patent No.: US 10,357,762 B2
(45) Date of Patent: Jul. 23, 2019

(54) MIXED METAL DOUBLE SALT IONIC LIQUIDS WITH TUNABLE ACIDITY

(71) Applicant: THE BOARD OF TRUSTEES OF THE UNIVERSITY OF ALABAMA, Tuscaloosa, AL (US)

(72) Inventors: Robin D. Rogers, Tuscaloosa, AL (US); Gabriela Gurau, Tuscaloosa, AL (US); Steven P. Kelley, Tuscaloosa, AL (US); Rajkumar Kore, Tuscaloosa, AL (US); Julia L. Shamshina, Northport, AL (US)

(73) Assignee: THE BOARD OF TRUSTEES OF THE UNIVERSITY OF ALABAMA, Tuscaloosa, AL (US)

(*) Notice: Subject to any disclaimer, the term of this patent is extended or adjusted under 35 U.S.C. 154(b) by 0 days.

(21) Appl. No.: 15/416,575

(22) Filed: Jan. 26, 2017

(65) Prior Publication Data

US 2017/0209858 A1    Jul. 27, 2017

Related U.S. Application Data

(60) Provisional application No. 62/287,180, filed on Jan. 26, 2016.

(51) Int. Cl.
| | | |
|---|---|---|
| *B01J 31/02* | (2006.01) | |
| *C07C 231/10* | (2006.01) | |
| *C07D 215/06* | (2006.01) | |
| *C07C 45/00* | (2006.01) | |
| *C07C 211/63* | (2006.01) | |

(52) U.S. Cl.
CPC .......... *B01J 31/0298* (2013.01); *C07C 45/00* (2013.01); *C07C 211/63* (2013.01); *C07C 231/10* (2013.01); *C07D 215/06* (2013.01)

(58) Field of Classification Search
CPC ...... C07C 45/65; C07C 231/10; C07D 215/06
See application file for complete search history.

(56) References Cited

U.S. PATENT DOCUMENTS

| | | | |
|---|---|---|---|
| 5,824,832 A | 10/1998 | Shyu et al. | |
| 2007/0093462 A1 | 4/2007 | Rogers et al. | |
| 2008/0207452 A1 | 8/2008 | Kramer et al. | |
| 2010/0331182 A1 | 12/2010 | Hong et al. | |
| 2011/0275517 A1 | 11/2011 | Satchivi et al. | |
| 2013/0109572 A1 | 5/2013 | Pernak et al. | |
| 2013/0252945 A1 | 9/2013 | Lovejoy et al. | |
| 2014/0274713 A1 | 9/2014 | Barrientos et al. | |

OTHER PUBLICATIONS

Ratti; Advances in Chemistry; 2014, Article ID 729842, 16 pages.*
Huang (Applied Catalysis A: General 277 (2004) 41-43).*
Liu (Applied Catalysis A: General 346 (2008) 189-193).*
Jonson (The Electrochemical Society interface; Spring 2007; 38-41).*
Rogers, et al., "Ionic liquid forms of the herbicide dicamba with increased efficacy and reduced volatility", Green Chem, 2013, 2110-2120.
Praczyk, et al., "Herbicidal Ionic Liquids with 2,4-D", Weed Sci. 2012, 60, 189-192. Abstract.
Carlin, et al., "Chemistry and Specification in Room-Temperature Chloroaluminate Molten Salts",Chemistry of Nonaqueous Solutions: Current Progress, VCH Publishing, New York, 1994, Ch. 5; 30 pages.
Cui, et al., "Identification of acidic species in chloroaluminate ionic liquid catalysts", Journal of Catalysis 320, 2014, 26-32.
Estager, et al., "Halometallate ionic liquids—revisite", Chemical Society Reviews 43, 2014, 847-886.
Grey, et al., "Aluminum-27 nuclear magnetic resonance study of the room-temperature melt aluminum trichloride butylpyridinium chloride", Am. Chem. Soc. 103, 1981, 7147-7151.
Huang, et al., "Effects of additives on the properties of chloroaluminate ionic liquids catalyst for alkylation of isobutane and butene", Applied Catalysis A: General 277, 2004, 41-43.
Kore, et al., "A simple, eco-friendly, and recyclable bi-functional acidic ionic liquid catalysts for Beckmann rearrangement", Journal of Molecular Catalysis A: Chemical 376, 2013, 90-97.
Liu, et al., "Alkylation of isobutene with 2-butene using composite ionic liquid catalysts", Applied Catalysis A: General 346, 2008, 189-193.
International Search Report and Written Opinion issued in co-pending International Application No. PCT/US15/59861, dated Feb. 2, 2016.
Wasserscheid, et al., "Ionic Liquids-New "Solutions" for Transition Metal Catalysis", Angew Chem Int Ed Engl. 39, 2000, 3772-3789.
Welton et al., "Room-Temperature Ionic Liquids. Solvents for Synthesis and Catalysis", Chemical Reviews, vol. 99, No. 8, Jul. 7, 1999, 2071-2083.

(Continued)

*Primary Examiner* — Pancham Bakshi
(74) *Attorney, Agent, or Firm* — Meunier Carlin & Curfman LLC

(57) ABSTRACT

Disclosed are double salt ionic liquids that include at least one organic cation and at least two metal halide anions. Methods of making the double salt ionic liquids can include combining two or more metal halide containing salts, wherein the metal halide containing salts include at least one organic cation and at least two metal halide anions. The reaction between the two or more salts at any ratio allows fine tuning, rate of dissolution, solubility, and bioavailability of the double salt ionic liquids. The ionic liquids disclosed herein can be used as a catalyst for catalyzing a chemical reaction. The chemical reaction can be an acid catalyzed chemical reaction such as a Lewis acid catalyzed reaction, a Beckmann rearrangement reaction, a Meyer-Schuster rearrangement reaction, a heterocyclic synthesis, a reaction for biodiesel production, a mercury-catalyzed type reaction, or a hydrogen-fluoride catalyzed type reaction.

20 Claims, 32 Drawing Sheets

(56) References Cited

OTHER PUBLICATIONS

Zhu, et al., "Effects of Chloroaluminate Ionic Liquid on Alkylation of Benzene with Mixture of Alkenes and Alkanes", Bulletin of Catalysis Society of India 6, 2007, 83-9.

* cited by examiner

MIXED METAL DOUBLE SALT IONIC LIQUIDS WITH TUNABLE ACIDITY

CROSS-REFERENCE TO RELATED APPLICATIONS

This application claims priority to U.S. Provisional Patent Application No. 62/287,180, filed Jan. 26, 2016, and entitled "MIXED METAL DOUBLE SALT IONIC LIQUIDS WITH TUNABLE ACIDITY," the entire disclosure of which is incorporated herein by reference.

FIELD

This disclosure relates generally to ionic liquids, particularly to mixed metal double salt ionic liquids with tunable acidity.

BACKGROUND

Brønsted acid compounds such as hydrofluoric acid and sulfuric acid are highly toxic and corrosive. However, they are useful as catalysts in isomerization, condensation, polymerization, and hydrolysis reactions. For example, hydrofluoric acid is used as a catalyst in conventional industrial processes to perform reactions such as aromatic and olefin alkylation, including in refinery processes for the production of high-octane gasoline, distillate, and lubricating base oil. Efforts to develop safer, alternative acid catalysts have encountered serious challenges.

Lewis acid ionic liquids, such as chloroaluminate, have been investigated for catalysts replacement of hydrofluoric acid and sulfuric acid (see for example, U.S. Pat. No. 5,824,832 to Sherif et al. and Zhu et al., Bulletin of Catalysis Society of India, 2007, 6, 83-89). The effect of the addition of different metals to chloroaluminates was also investigated on the catalytic activity of the resultant complexes. For example, it was reported that the addition of neutral copper (I) chloride (CuCl) into the chloroaluminate ionic liquids increased their catalytic activity (Estager et al., *Chemical Society Reviews*, 2014, 43, 847-886; Huang et al., *Applied Catalysis A: General*, 2004, 277, 41-43; Cui et al., *Journal of Catalysis*, 2014, 320, 26-32; Liu et al., *Applied Catalysis A: General*, 2008, 346, 189-193).

There is a need for replacing toxic and corrosive acid catalysts that are used in processes such as conventional alkylation reactions. The compositions and methods disclosed herein address these and other needs.

SUMMARY

Disclosed herein are compositions and methods of making and using such compositions. In a specific aspect, disclosed herein are ionic liquids. In some aspects, the ionic liquids can include at least one organic cation and at least two metal halide anions. The ionic liquids are salts of the at least one organic cation and the at least two metal halide anions with a melting point at or below about 150° C.

In some examples, the ionic liquid can have a structure according to the formula:

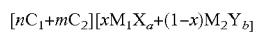

wherein $C_1$ and $C_2$ are cations; $M_1$ and $M_2$ are metals; $X_a$ and $Y_b$ are halides; n is a number from 0 to 5; m is a number from 0 to 5; x is a number from 0.01 to 0.99; wherein the sum of n+m is greater than 0; and wherein at least one of $C_1$ and $C_2$ comprises an organic cation.

In some examples, the at least one organic cation can be selected from an alkylammonium, an arylammonium, an allylammonium, an imidazolium, a pyridinium, a phosphonium, a sulphonium, and a combination thereof. For example, the at least one organic cation can be an ammonium cation of the structure $^+NR^1R^2R^3R^4$, wherein $R^1$, $R^2$, $R^3$, and $R^4$ are each independently selected from hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted heteroaryl, and substituted or unsubstituted carbonyl, or wherein two or more of $R^1$, $R^2$, $R^3$, and $R^4$ optionally combine to form a ring. In some examples, one or more of $R^1$, $R^2$, $R^3$, and $R^4$ can be methyl, ethyl, propyl, or butyl. In some examples, two or more of $R^1$, $R^2$, $R^3$, and $R^4$ can combine to form a ring, the ring including between 3 and 12 atoms. In some examples, two or more of $R^1$, $R^2$, $R^3$, and $R^4$ can combine to form a ring, the ring including at least one double bond.

In some other examples, the at least one organic cation can be a substituted or unsubstituted heteroaryl cation. The heteroaryl cation can be selected from a substituted or unsubstituted pyridinium cation, a substituted or unsubstituted imidazolium cation, a substituted or unsubstituted morpholinium, a substituted or unsubstituted pyrrolidinium cation, a substituted or unsubstituted quinolinium cation, a substituted or unsubstituted isoquinolinium cation, and a substituted or unsubstituted morpholinium cation.

In some examples, the at least one organic cation can be a phosphonium cation of the structure $^+PR^1R^2R^3R^4$, wherein $R^1$, $R^2$, $R^3$, and $R^4$ are each independently selected from hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted heteroaryl, and substituted or unsubstituted carbonyl, or wherein two or more of $R^1$, $R^2$, $R^3$, and $R^4$ optionally combine to form a ring.

In some examples, the at least one organic cation can be selected from dimethylammonium, trimethylammonium, tetramethylammmonium, diethylammonium, triethylammonium, tetraethylammmonium, dipropylammonium, tripropylammonium, and tetrapropylammmonium.

In some examples, the metals ($M_1$ and $M_2$) in the at least two metal halides anions of the ionic liquid can each be independently selected from a Group III metal, a transition metal, and a combination thereof. In some examples, the at least two metal halide anions are each independently selected from halometallates. For examples, the at least two metal halide anions can be each independently selected from chloroaluminate, chlorozincate, chloroferrate, chlorogallate, chlorostannate, chloroindate, chlorochromate, chlorocuprate, chlorotitannate, chlorozirconate, chloropalladate, and combinations thereof. The molar ratio of the at least two metal halide anions can be from 1 to 99. For example, the molar ratio of the at least two metal halide anions can be selected from 1, 1.5, 2, 2.33, 3, 4, and 9.

The ionic liquid can further include a solvent or a mixture of solvents.

The ionic liquids disclosed herein can be used as a catalyst for catalyzing a chemical reaction. In some embodiments, the chemical reaction can be an acid catalyzed chemical reaction. For example, the acid catalyzed chemical reaction can be a Lewis acid catalyzed reaction, chosen from Friedel Crafts alkylation or acylation, or similar reactions with carbonyl-containing substrates, Diels-Alder reactions, addition and conjugate addition to carbonyl compounds, addition of silyl enol ethers and allylsilanes to carbonyl compounds, a carbonyl-ene reaction, a Beckmann rearrangement reaction, a reaction for biodiesel production, a mercury-catalyzed type reaction, or a hydrogen-fluoride catalyzed type reaction. The catalytic ionic liquids can be recycled subsequent to use.

Methods of making the ionic liquids herein are also disclosed. The method can include combining two or more metal halide containing salts, wherein the metal halide containing salts include at least one organic cation and at least two metal halide anions.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
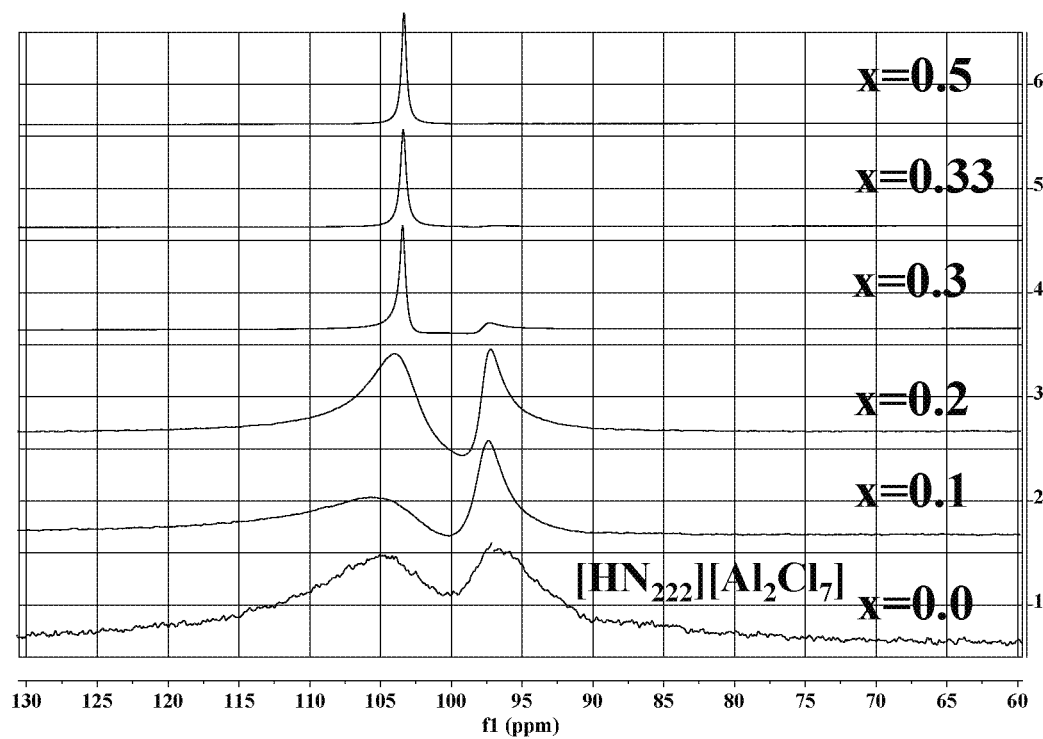
FIG. 1 is an $^{27}Al$ NMR spectrum of $[HN_{222}]_{(1+x)}[(1-x)Al_2Cl_7+xZnCl_4]$ with different molar fraction (55° C., neat, DSMO-$d_6$ lock); where x=0, the molecule is $[HN_{222}][Al_2Cl_7]$.

Provided herein are ionic liquid compositions. The ionic liquid can include at least one organic cation and at least two metal halide anions. By combining the anions and cations disclosed herein, a double salt ionic liquid can result. As such, the disclosed compositions in some aspects can be double salt ionic liquids and can be used in that form. Methods of making and using the compositions are also described herein.

The compositions and methods described herein can be understood more readily by reference to the following detailed description of specific aspects of the disclosed subject matter and the examples included therein. However, before the present compositions and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout this specification the word "comprise" and other forms of the word, such as "comprising" and "comprises," means including but not limited to, and is not intended to exclude, for example, other additives, components, integers, or steps.

The singular forms "a," "an," and "the" include plural referents unless the context clearly dictates otherwise. Thus, for example, reference to "a composition" includes mixtures of two or more such compositions, reference to "an ionic liquid" includes mixtures of two or more such ionic liquids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$ and $C_m$ indicates in each case the possible number of carbon atoms in the group.

References in the specification and concluding claims to the molar ratio of a particular element or component in a composition denotes the molar relationship between the element or component and any other elements or components in the composition or article for which a part by weight is expressed. Thus, in a compound containing 2 moles of X and 5 moles of Y, X and Y are present at a molar ratio of 2:5, and are present in such ratio regardless of whether additional components are contained in the compound.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both at the same time within one molecule, cluster of molecules, molecular complex, or moiety (e.g., zwitterions)) or that can be made to contain a charge. Methods for producing a charge in a molecule, portion of a molecule, cluster of molecules, molecular complex, moiety, or atom are disclosed herein and can be accomplished by methods known in the art, e.g., protonation, deprotonation, oxidation, reduction, alkylation, acetylation, esterification, deesterification, hydrolysis, etc.

The term "anion" is a type of ion and is included within the meaning of the term "ion." An "anion" is any molecule, portion of a molecule (e.g., zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion." A "cation" is any molecule, portion of a molecule (e.g., zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

The term "aliphatic" as used herein refers to a non-aromatic hydrocarbon group and includes branched and unbranched, alkyl, alkenyl, or alkynyl groups.

The term "alkyl," as used herein, refers to saturated straight, branched, primary, secondary or tertiary hydrocarbons, including those having 1 to 20 atoms. In some examples, alkyl groups will include $C_1$-$C_{12}$, $C_1$-$C_{10}$, $C_1$-$C_8$, $C_1$-$C_6$, $C_1$-$C_5$, $C_1$-$C_4$, $C_1$-$C_3$, or $C_1$-$C_2$ alkyl groups. Examples of $C_1$-$C_{10}$ alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl groups, as well as their isomers. Examples of $C_1$-$C_4$-alkyl groups include, for example, methyl, ethyl, propyl, 1-methylethyl, butyl, 1-methylpropyl, 2-methylpropyl, and 1,1-dimethylethyl groups.

Cyclic alkyl groups or "cycloalkyl" groups include cycloalkyl groups having from 3 to 10 carbon atoms. Cycloalkyl groups can include a single ring, or multiple condensed rings. In some examples, cycloalkyl groups include $C_3$-$C_4$, $C_4$-$C_7$, $C_5$-$C_7$, $C_4$-$C_6$, or $C_5$-$C_6$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

Alkyl and cycloalkyl groups can be unsubstituted or substituted with one or more moieties chosen from alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999, hereby incorporated by reference.

Terms including the term "alkyl," such as "alkylamino" or "dialkylamino," will be understood to comprise an alkyl group as defined above linked to another functional group, where the group is linked to the compound through the last group listed, as understood by those of skill in the art.

The term "aryl," as used herein, refers to a monovalent aromatic carbocyclic group of from 6 to 14 carbon atoms. Aryl groups can include a single ring or multiple condensed rings. In some examples, aryl groups include $C_6$-$C_{10}$ aryl groups. Aryl groups include, but are not limited to, phenyl, biphenyl, naphthyl, tetrahydronaphthyl, phenylcyclopropyl and indanyl. Aryl groups can be unsubstituted or substituted by one or more moieties chosen from halo, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "alkoxy," as used herein, refers to alkyl-O—, wherein alkyl refers to an alkyl group, as defined above. Similarly, the terms "alkenyloxy," "alkynyloxy," and "cycloalkoxy," refer to the groups alkenyl-O—, alkynyl-O—, and cycloalkyl-O—, respectively, wherein alkenyl, alkynyl, and cycloalkyl are as defined above. Examples of $C_1$-$C_6$-alkoxy groups include, but are not limited to, methoxy, ethoxy, $C_2CH_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1 methylbutoxy, 2-methylbutoxy, 3-methylbutoxy, 1,1-dimethylpropoxy, 1,2 dimethylpropoxy, 2,2-dimethyl-propoxy, 1-ethylpropoxy, n-hexoxy, 1 methylpentoxy, 2-methylpentoxy, 3-methylpentoxy, 4-methylpentoxy, 1,1 dimethylbutoxy, 1,2-dimethylbutoxy, 1,3-dimethylbutoxy, 2,2-dimethylbutoxy, 2,3 dimethylbutoxy, 3,3-dimethylbutoxy, 1-ethylbutoxy, 2-ethylbutoxy, 1,1,2 trimethylpropoxy, 1,2,2-trimethylpropoxy, 1-ethyl-1-methylpropoxy, and 1-ethyl-2-methylpropoxy.

The term "heteroaryl," as used herein, refers to a monovalent aromatic group of from 1 to 15 carbon atoms (e.g., from 1 to 10 carbon atoms, from 2 to 8 carbon atoms, from 3 to 6 carbon atoms, or from 4 to 6 carbon atoms) having one or more heteroatoms within the ring. The heteroaryl group can include from 1 to 4 heteroatoms, from 1 to 3 heteroatoms, or from 1 to 2 heteroatoms. In some examples, the heteroatom(s) incorporated into the ring are oxygen, nitrogen, sulfur, or combinations thereof. When present, the nitrogen and sulfur heteroatoms can optionally be oxidized. Heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings can be unsubstituted or substituted by one or more moieties as described for aryl above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

The term "halogen" or "halide," as used herein, refers to the atoms fluorine, chlorine, bromine and iodine. The prefix halo- (e.g., as illustrated by the term haloalkyl) refers to all degrees of halogen substitution, from a single substitution to a perhalo substitution (e.g., as illustrated with methyl as chloromethyl (—$CH_2C_1$), dichloromethyl (—$CHCl_2$), trichloromethyl (—$CCl_3$)).

The term "cyclic group" or "ring" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group or ring can contain one or more aryl groups, one or more non-aryl groups, or one or more aryl groups and one or more non-aryl groups.

The terms "amine" or "amino" as used herein are represented by the formula $NR^1R^2R^3$, where $R^1$, $R^2$, and $R^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula OC(O)A$^1$ or —C(O)OA$^1$, where A$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "hydroxyl" as used herein is represented by the formula —OH.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless otherwise stated herein, if a group is identified as being "substituted" it is meant that the group is substituted with one or more alkyl, alkoxy, alkenyl, alkynyl, aryl, heteroaryl, aldehyde, amino, carboxylic acid, ester, ether, halide, hydroxy, ketone, nitro, silyl, sulfonyl, sulfone, sulfoxide, or thiol groups.

The term "ionic liquid" describes a salt with a melting point below 150° C., whose melt is composed of discrete ions.

The term "double salt ionic liquid" describes an ionic liquid, which comprises two or more cations and/or two or more anions within the same composition.

It is understood that throughout this specification the identifiers "first" and "second" are used solely to aid in distinguishing the various components and steps of the disclosed subject matter. The identifiers "first" and "second" and the like are not intended to imply any particular order, amount, preference, or importance to the components or steps modified by these terms.

Reference will now be made in detail to specific aspects of the disclosed materials, compounds, compositions, articles, and methods, examples of which are illustrated in the accompanying Examples.

Materials and Compositions

In one aspect, disclosed herein are ionic liquid compositions. In some embodiments, the ionic liquid compositions disclosed herein can include at least one cation and at least two anions. The at least one cation, can include an organic group-containing cation, as described herein. The at least two anions, can include a metal halide anion, as described herein.

The term "ionic liquid" has many definitions in the art, but is used herein to refer to salts (i.e., compositions comprising cations and anions) that are liquid at a temperature of at or below about 150° C., e.g., at or below about 120, 100, 80, 60, 40, or 25° C. That is, at one or more temperature ranges or points at or below about 150° C. the disclosed ionic liquid compositions are liquid; although, it is understood that they can be solids at other temperature ranges or points. Since the disclosed ionic liquid compositions are liquid, and thus not crystalline solids, at a given temperature, the disclosed compositions do not suffer from the problems of polymorphism associated with crystalline solid. An ionic liquid is not considered a mere solution containing ions as solutes dissolved therein.

The use of the term "liquid" to describe the disclosed ionic liquid compositions is meant to describe a generally amorphous, non-crystalline, or semi-crystalline state. For example, while some structured association and packing of cations and anions can occur at the atomic level, the disclosed ionic liquid compositions have minor amounts of such ordered structures and are therefore not crystalline solids. The compositions disclosed herein can be fluid and free-flowing liquids or amorphous solids such as glasses or waxes at a temperature at or below about 150° C. In particular examples disclosed herein, the disclosed ionic liquid compositions are liquid at which the composition is applied (i.e., ambient temperature).

Further, the disclosed ionic liquid compositions are materials composed of at least two different ions; each of which can independently and simultaneously introduce a specific characteristic to the composition not easily obtainable with traditional dissolution and formulation techniques. Thus, by providing different ions and ion combinations, one can change the characteristics or properties of the disclosed ionic liquid compositions in a way not seen by simply preparing various crystalline salt forms. Examples of characteristics that can be controlled in the disclosed compositions include, but are not limited to, melting, solubility control, and rate of dissolution. It is this multi-nature/functionality of the disclosed ionic liquid compositions which allows one to fine-tune or design in very specific desired material properties.

Anions

As disclosed herein, the ionic liquids can include at least two anions. In some embodiments, the disclosed ionic liquids can include two or more anions (e.g., 3, 4, 5, 6, 7, 8, 9, 10, or more anions). The anions in the disclosed ionic liquids can be the same or different. In some aspects, the anions in the disclosed ionic liquids can be different, that is, the ionic liquids can comprise more than one kind of anion (e.g., 2, 3, 4, 5, 6, 7, 8, 9, 10, or more different kinds of anions).

The anions in the ionic liquids can each be independently selected from metal halide anions (also referred to herein as "halometallates"). The term "metal halide anion" as used herein refers to a complex polyatomic anion, which contain at least a halogen bonded to a primary metal. These complexes may have a number of halogen atoms bonded to the primary metal in excess of the usual valence number of the metal. Alternatively, one or more of such halogen can be replaced by oxygen or other atoms. The term "primary metal" is used to refer to a metal that can form a complex anion with a halogen. In some embodiments, the ionic liquid can include at least two metal halide anions.

In some embodiments, the primary metal in the metal halide anions can include a metal selected from Group II or Group III of the periodic table, transition metals, or combinations thereof. In some examples, the primary metal can be selected from aluminum, iron, chromium, zinc, copper, tin, titanium, palladium, zirconium, gallium, and combinations thereof.

The metal halide anions disclosed herein can include at least one halide selected from Cl, F, Br, and I.

In some examples, the at least two metal halide anions in the ionic liquids disclosed herein can be independently selected from chloroaluminate, chlorozincate, chloroferrate, chlorogallate, chlorostannate, chloroindate, chlorochromate, chlorocuprate, chlorotitannate, chlorozirconate, chloropalladate, and combinations thereof.

The at least two metal halide anions can be incorporated into the ionic liquids in any suitable molar ratio so long as there is a balance of charge with the cation(s). For example, if a singly charged cation is selected ($C_1$), and two singly charged metal halide anions are selected ($M_1X_a$ and $M_2Y_b$), they can be used in an amount that would give an ionic liquid with the following formula: $[C_1][M_1X_a]_{0.5}[M_2Y_b]_{0.5}$, where $C_1$ is a cation; $M_1$ and $M_2$ are metals; and $X_a$ and $Y_b$ are halides. This can indicate that half of the anions can be comprised of the first metal halide and half of the anions can be comprised of the second metal halide. Other examples would include $[C_1][M_1X_a]_{0.25}[M_2Y_b]_{0.75}[C_1][M_1X_a]_{0.25}[M_2Y_b]_{0.9}$ and the like. Also, a greater number of different anions can be paired with a properly selected cation, such as a 1 to 1 to 2 ratio of the first metal halide to the second metal halide to a third anion (such as, $[C_1][M_1X_a]_{0.25}[M_2Y_b]_{0.25}[M_3Z_c]_{0.5}$).

In some embodiments, the at least two metal halide anions can be incorporated into the disclosed ionic liquids in a molar ratio of 1:1 or greater. For example, the anions can be incorporated into the ionic liquid compositions in a molar ratio of 1:1.2 or greater, 1:1.3 or greater, 1:1.4 or greater, 1:1.5 or greater, 1:1.6 or greater, 1:1.7 or greater, 1:1.8 or greater, 1:1.9 or greater, 1:2 or greater, 1:2.3 or greater, 1:2.5 or greater, 1:2.8 or greater, 1:3 or greater, 1:4 or greater, 1:5 or greater, 1:6 or greater, 1:7 or greater, 1:8 or greater, 1:9 or greater, 1:10 or greater, 1:20 or greater, 1:30 or greater, 1:40 or greater, 1:50 or greater, 1:60 or greater, 1:70 or greater, 1:80 or greater, 1:90 or greater, or 1:99 or greater. In some embodiments, the anions can be incorporated into the ionic liquid compositions in a molar ratio of 1:20 or less, 1:15 or less, 1:10 or less, 1:9 or less, 1:8 or less, 1:7 or less, 1:6 or less, 1:5 or less, 1:4 or less, 1:3 or less, 1:2.5 or less, 1:2 or less, 1:1.9 or less, 1:1.8 or less, 1:1.7 or less, 1:1.5 or less, 1:1.3 or less, 1:1.2 or less, or 1:1 or less. In some embodiments, the anions can be incorporated into the ionic liquid compositions in a molar ratio of from 1:1 to 1:20, from 1:1 to 1:10, from 1:1 to 1:8, from 1:1 to 1:6, from 1:1 to 1:5, from 1:1 to 1:4, from 1:1 to 1:3, or from 1:1 to 1:2, and anything in-between. In some examples, the molar ratio of the at least two metal halide anions can be from 1 to 99, and anything in-between. For example, the molar ratio of the at least two metal halide anions can be selected from 1, 1.5, 2, 2.33, 3, 4, and 9. Some examples of the anions in the ionic liquid compositions are shown in Table 1. Whatever ratio is chosen, however, should result in a balance of charge with the cation(s).

Cations

As disclosed herein, the ionic liquids can include at least one cation. For example, the disclosed ionic liquids can comprise one or more cations (e.g., 2, 3, 4, 5, 6, 7, 8, 9, 10, or more different cations). The cations in the disclosed ionic liquids can be the same or different. In some aspects, the cations in the disclosed ionic liquids can be different, that is, the ionic liquids can comprise more than one kind of cation (e.g., 2, 3, 4, 5, 6, 7, 8, 9, 10, or more different kinds of cations).

The cation in the disclosed ionic liquids can be an organic group-containing cation (also referred to herein as "organic cation"). The organic cation can be a complex polyatomic cation, which contains at least an organic group bonded to a heteroatom. In some embodiments, the ionic liquid can include at least one organic cation.

Particular examples of organic cations that can be present in the disclosed ionic liquids include compounds that contain nitrogen, phosphorus, or a sulfur heteroatom. Nitrogen atom-containing groups can exist as a neutral compound or can be converted to a positively-charged quaternary ammonium species, for example, through alkylation or protonation of the nitrogen atom. Thus, compounds that possess a quaternary nitrogen atom (known as quaternary ammonium compounds (QACs)) are typically cations. According to the methods and compositions disclosed herein, any compound that contains a quaternary nitrogen atom or a nitrogen atom that can be converted into a quaternary nitrogen atom (cation precursor) can be a suitable cation for the disclosed ionic liquids.

In some examples, phosphorous atoms can exist as a charged phosphonium species, for example, through alkylation of the phosphorous atom. Thus, compounds that possess a quaternary phosphorous atom (known as quaternary phosphonium compounds) are typically cations. According to the methods and compositions disclosed herein, any compound that contains a quaternary phosphorus atom or a phosphorus atom that can be converted into a quaternary phosphonium atom can be a suitable cation for the disclosed ionic liquids.

In some examples, sulfur atoms can exist as a charged sulfonium species, for example, through alkylation of the sulfurous atom. Thus, compounds that possess a ternary sulfurous atom are typically cations. According to the methods and compositions disclosed herein, any compound that contains a ternary sulfurous atom or a sulfurous atom that can be converted into a ternary sulfurous atom can be a suitable cation for the disclosed ionic liquids.

Heteroaryls

Some specific nitrogen containing organic cations suitable for use herein are heteroaryls. In some embodiments, the heteroaryl can be an aliphatic heteroaryl. An aliphatic heteroaryl cation is a compound that comprises at least one aliphatic moiety bonded to a heteroaryl moiety. In the aliphatic heteroaryl cation, the aliphatic moiety can be any alkyl, alkenyl, alkynyl, heteroalkyl, heteroalkenyl, heteroalkynyl, cycloalkyl, cycloalkenyl, heterocycloalkyl, or heterocycloalkenyl group, as described herein.

In the heteroaryl cation, the heteroaryl moiety can be any heteroaryl moiety as described herein. For example, the heteroaryl moiety can be an aryl group having a nitrogen atom and optionally one or more heteroatoms (e.g., oxygen, sulfur, phosphorous, or halonium). Examples of specific heteroaryl moieties that can be used in the heteroaryl cations include, but are not limited to, substituted or unsubstituted benztriazoliums, substituted or unsubstituted benzimidazoliums, substituted or unsubstituted benzothiazoliums, substituted or unsubstituted pyridiniums, substituted or unsubstituted pyridaziniums, substituted or unsubstituted pyrimidiniums, substituted or unsubstituted pyraziniums, substituted or unsubstituted imidazoliums, substituted or unsubstituted pyrazoliums, substituted or unsubstituted oxazoliums, substituted or unsubstituted 1,2,3-triazoliums, substituted or unsubstituted 1,2,4-triazoliums, substituted or unsubstituted thiazoliums, substituted or unsubstituted piperidiniums, substituted or unsubstituted pyrrolidiniums, substituted or unsubstituted quinoliums, and substituted or unsubstituted isoquinoliums. As described herein, when the heteroatom of the heteroaryl is nitrogen, this forms a quaternary ammonium cation.

Further examples of heteroaryl cations include substituted or unsubstituted pyrazoles, substituted or unsubstituted pyridines, substituted or unsubstituted pyrazines, substituted or unsubstituted pyrimidines, substituted or unsubstituted pryidazines, substituted or unsubstituted indolizines, substituted or unsubstituted isoindoles, substituted or unsubstituted indoles, substituted or unsubstituted indazoles, substituted or unsubstituted imidazoles, substituted or unsubstituted oxazoles, substituted or unsubstituted triazoles, substituted or unsubstituted thiazoles, substituted or unsubstituted purines, substituted or unsubstituted isoquinolines, substituted or unsubstituted quinolines, substituted or unsubstituted phthalazines, substituted or unsubstituted quinooxalines, substituted or unsubstituted phenazine, substituted or unsubstituted morpholiniums, and the like, including derivatives and mixtures thereof.

Ammonium ($NR^1R^2R^3R^4$)

The disclosed ionic liquid compositions can also comprise an ammonium cation of the structure $NR^1R^2R^3R^4$, wherein $R^1$, $R^2$, $R^3$, and $R^4$ are each independently selected from hydrogen, substituted or unsubstituted aliphatic moiety, a substituted or unsubstituted aryl moiety, substituted or unsubstituted heteroaryl moiety, or wherein two or more of $R^1$, $R^2$, $R^3$, and $R^4$ optionally combine to form a ring.

The aliphatic moiety can be any alkyl, alkenyl, alkynyl, heteroalkyl, heteroalkenyl, heteroalkynyl, cycloalkyl, cycloalkenyl, heterocycloalkyl, or heterocycloalkenyl group, as described herein. For example, the aliphatic moiety can include substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl substituted or unsubstituted $C_{2-20}$ heteroalkenyl, or substituted or unsubstituted $C_{2-20}$ heteroalkynyl groups. Generally, the aliphatic moiety can comprise 1 or more, 2 or more, 3 or more, 4 or more, 5 or more, or 6 or more carbon atoms. In other examples, the aliphatic moiety can comprise a mixture of aliphatic groups having a range of carbon atoms. For example, the aliphatic moiety can comprise from 1 to 20, from 1 to 18, from 1 to 15, from 1 to 10, or from 1 to 6 carbon atoms. In some specific examples, the aliphatic moiety can contain 1, 2, 3, 4, 5, 6, 7, 8, 9, 10, 11, 12, 13, 14, 15, 16, 17, 18, 19, or 20 carbon atoms, where any of the stated values can form an upper or lower endpoint when appropriate. Examples of specific aliphatic moieties that can be used include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl, and decyl, dodecyl (lauryl), tetradecyl (myristyl), hexadecyl (palmityl or cetyl), octadecyl (stearyl), eicosyl (arachidyl), and linolenyl groups, including branched derivatives thereof and any mixtures thereof. The aliphatic moieties can further include alkoxymethyl groups (e.g., containing from 2 to 19 carbon atoms) or cycloalkoxymethyl groups (e.g., containing from 5 to 13 carbon atoms). In the aliphatic heteroaryl cations, the aliphatic moiety is bonded to a heteroatom in the heteroaryl moiety.

In some examples, the disclosed ionic liquid compositions can comprise an ammonium cation of the structure $NR^1R^2R^3R^4$, wherein $R^1$, $R^2$, $R^3$, and $R^4$ are each independently selected from hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted heteroaryl, or wherein two or more of $R^1$, $R^2$, $R^3$, and $R^4$ optionally combine to form a ring.

In some examples, two, three, or four of $R^1$-$R^4$ can comprise alkyl moieties. In some examples, the ammonium cation can comprise $NR^1R^1R^2R^3R^4$, wherein $R^1$ and $R^2$ are independently selected from substituted or unsubstituted $C_{1-20}$ alkyl, and $R^3$ and $R^4$ are independently selected from substituted or unsubstituted $C_{2-20}$ alkenyl. In some examples, the ammonium cation can be selected from dimethylammonium, trimethylammonium, tetramethylammmonium, diethylammonium, triethylammonium, tetraethylammmonium, dipropylammonium, tripropylammonium, or tetrapropylammmonium, diallyldimethyl ammonium, di-dodecyl dimethyl ammonium, di-tetradecyl dimethyl ammonium, dihexadecyl dimethyl ammonium, and the like, including combinations thereof. In some examples, three of $R^1$—$R^4$ can comprise alkyl moeities of equivalent length, such as in triethylammonium.

Alkoxyalkyl Ammonium

The disclosed ionic liquid compositions can also comprise an alkoxyalkyl ammonium cation of the structure $NR^1R^2R^3R^4$, wherein $R^1$, $R^2$, $R^3$, and $R^4$ are each independently selected from substituted or unsubstituted $C_{1-20}$ alkyl, wherein at least one of $R^1$, $R^2$, $R^3$, and $R^4$ is substituted with an alkoxy group. In some examples, at least one of $R^1$—$R^4$ can comprise ethoxymethyl.

Benzylalkyl Ammonium

The disclosed ionic liquid compositions can also comprise a benzylalkyl ammonium cation of the structure $NR^1R^2R^3R^4$, wherein $R^1$, $R^2$, $R^3$, are each independently selected from hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted $C_{1-20}$ heteroalkyl, substituted or unsubstituted $C_{2-20}$ heteroalkenyl, substituted or unsubstituted $C_{2-20}$ heteroalkynyl, or substituted or unsubstituted heteroaryl, or substituted or unsubstituted carbonyl, and wherein $R^4$ comprises a benzyl group. Examples of benzylalkyl ammonium cations include, but are not limited to, alkyl dimethyl benzyl ammonium cations (such as trimethyl benzyl ammonium, triethyl benzyl ammonium, or dimethyl propyl benzyl ammonium).

In some examples, the benzalkyl ammonium cation can comprise a mixture of molecules with varying lengths of alkyl groups.

Phosphonium ($PR^1R^2R^3R^4$)

The disclosed ionic liquid compositions can also comprise a phosphonium cation of the structure $PR^1R^2R^3R^4$, wherein $R^1$, $R^2$, $R^3$, and $R^4$ are each independently selected from hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted heteroaryl, or substituted or unsubstituted carbonyl.

In some examples, the phosphonium cation can comprise $PR^1R^2R^3R^4$, wherein $R^1$ and $R^2$ are independently selected from substituted or unsubstituted $C_{1-20}$ alkyl, and $R^3$ and $R^4$ are independently selected from substituted or unsubstituted $C_{2-20}$ alkenyl. In some examples, the phosphonium cation can comprise tetraalkyl phosphonium cations, alkoxyalkyl phosphonium cations, and benzalkyl phosphonium cations.

Some specific examples of phosphonium cations include, but are not limited to, tetramethylphosphonium, ethyltrimethylphoshonium, diallyldimethylphoshonium, triethylmethylphoshonium, butyltrimethylphosphonium, propyltriethylphosphonium, dimethyldiethyl phosphonium, lauryl dimethylethyl phosphonium, or mixtures thereof.

Tetraalkylphosphonium

The disclosed ionic liquid compositions can also comprise a tetraalkyl phosphonium cation of the structure $PR^1R^2R^3R^4$, wherein $R^1$, $R^2$, $R^3$, and $R^4$ are each independently selected from substituted or unsubstituted $C_{1-20}$ alkyl.

In some examples, a tetraalkylphosonium cation can comprise four short chain alkyl moieties (e.g., 10 or less carbon atoms in length), such as tetrabutylphoshonium. In some examples, a tetraalkylphosphonim caiton can comprise other lengths of alkyl chains, such as a mixture of two short chain alkyl moieties (e.g., 10 or less carbon atoms in length) and two long chain alkyl moieties (e.g., 10 or more carbon atoms in length).

In another example, a tetraalkylphosphonium cation can comprise one long chain alkyl moiety (e.g., 10 or more carbon atoms in length) and three short chain alkyl moieties (e.g., less than 10 carbon atoms in length), such as trihexyltetradecylphosphonium.

Alkoxyalkyl Phosphonium

The disclosed ionic liquid compositions can also comprise an alkoxyalkyl phosphonium cation of the structure $PR^1R^2R^3R^4$, wherein $R^1$, $R^2$, $R^3$, and $R^4$ are each independently selected from substituted or unsubstituted $C_{1-20}$ alkyl, wherein at least one of $R^1$, $R^2$, $R^3$, and $R^4$ is substituted with an alkoxy group. In some examples, at least one of $R^1$—$R^4$ can comprise ethoxymethyl.

Sulfonium ($SR^1R^2R^3$)

The disclosed ionic liquid compositions can also comprise a sulfonium cation of the structure $SR^1R^2R^3$, wherein $R^1$, $R^2$, and $R^3$ are each independently selected from hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted heteroaryl, or substituted or unsubstituted carbonyl.

In some examples, the sulfonium cation can comprise $SR^1R^2R^3$, wherein $R^1$ and $R^2$ are independently selected from substituted or unsubstituted $C_{1-20}$ alkyl, and $R^3$ is independently selected from substituted or unsubstituted $C_{2-20}$ alkenyl. In some examples, the sulfonium cation can comprise diallylmethyl sulfonium, di-dodecyl methyl sulfonium, di-tetradecyl methyl sulfonium, dihexadecyl methyl sulfonium, and the like, including combinations thereof.

In some embodiments, the disclosed ionic liquids can include two or more organic cations. The two or more cations can be incorporated into the ionic liquid compositions in a molar ratio of 1:1 or greater. For example, the cations can be incorporated into the ionic liquid compositions in a molar ratio of 1:1.2 or greater, 1:1.3 or greater, 1:1.4 or greater, 1:1.5 or greater, 1:1.6 or greater, 1:1.7 or greater, 1:1.8 or greater, 1:1.9 or greater, 1:2 or greater, 1:2.3 or greater, 1:2.5 or greater, 1:2.8 or greater, 1:3 or greater, 1:4 or greater, 1:5 or greater, 1:6 or greater, 1:7 or greater, 1:8 or greater, 1:9 or greater, 1:10 or greater, 1:20 or greater, 1:30 or greater, 1:40 or greater, 1:50 or greater, 1:60 or greater, 1:70 or greater, 1:80 or greater, 1:90 or greater, or 1:99 or greater. In some embodiments, the cations can be incorporated into the ionic liquid compositions in a molar ratio of 1:20 or less, 1:15 or less, 1:10 or less, 1:9 or less, 1:8 or less, 1:7 or less, 1:6 or less, 1:5 or less, 1:4 or less, 1:3 or less, 1:2.5 or less, 1:2 or less, 1:1.9 or less, 1:1.8 or less, 1:1.7 or less, 1:1.5 or less, 1:1.3 or less, 1:1.2 or less, or 1:1 or less. In some embodiments, the cations can be incorporated into the ionic liquid compositions in a molar ratio of from 1:1 to 1:20, from 1:1 to 1:10, from 1:1 to 1:8, from 1:1 to 1:6, from 1:1 to 1:5, from 1:1 to 1:4, from 1:1 to 1:3, or from 1:1 to 1:2, and anything in-between. In some examples, the molar ratio of the two or more organic cations can be from 1 to 99, and anything in-between. For example, the molar ratio of the two or more organic cations can be selected from 1, 1.5, 2, 2.33, 3, 4, and 9. Some examples are shown in Table 1. Whatever ratio is chosen, however, should result in a balance of charge with the anion(s).

Double Salt Ionic Liquids

The ionic liquids disclosed herein can be double salt ionic liquids. Double salt ionic liquids are ionic liquids that contain greater than one cation and/or greater than one anion. In some aspects, the double salt ionic liquids described herein encompass ionic compounds containing at least one cation with at least two anions which are liquid below 150° C. These salts have unique physical and chemical properties, which are different than ionic liquids comprised of one cation and one anion. In the double salt ionic liquids, the electrostatic interactions are entirely different from those in each of the two parent ionic liquids. These unique interactions between the ions and their physical and chemical properties are derived from the specific choice and abundance of each type of ion. In the double salt ionic liquids, each ion uniquely interacts with the other ions present, to yield a new compound. This differs from physical mixtures where the components only loosely interact or a eutectic.

Suitable ions can be selected based on the above sections to generate unique double salt ionic liquids by modifying the ratios of the ions to generate the compounds. Examples of suitable anions and cations are disclosed herein. It should be understood that when a particular compound is disclosed as being a cation, for example, it may also, in other circumstances, be an anion and vice versa. Many compounds are known to exist as cations in some environments and anions in other environments. Further, many compounds are known to be convertible to cations and anions through various chemical transformations.

Any combination of cations and anions can be made as long as the combination would result in an ionic liquid as described herein. In some aspects, the disclosed double salt ionic liquids can comprise more than one kind of anion (e.g., 2, 3, 4, 5, 6, 7, 8, 9, 10, or more different kinds of metal halides as anions) with one or more than one kind of cation (e.g., 1, 2, 3, 4, 5, 6, 7, 8, 9, 10 or more different kinds of organic cations). Specific examples include, but are not limited to, one kind of cation with 2, 3, 4, 5, 6, 7, 8, 9, 10, or more kinds of anions, 2 kinds of cations with 2, 3, 4, 5, 6, 7, 8, 9, 10, or more kinds of anions, 3 kinds of cations with 2, 3, 4, 5, 6, 7, 8, 9, 10, or more kinds of anions, 4 kinds of cations with 2, 3, 4, 5, 6, 7, 8, 9, 10, or more kinds of anions, 5 kinds of cations with 2, 3, 4, 5, 6, 7, 8, 9, 10, or more kinds of anions, 6 kinds of cations with 2, 3, 4, 5, 6, 7, 8, 9, 10, or more kinds of anions, 7 kinds of cations with 2, 3, 4, 5, 6, 7, 8, 9, 10, or more kinds of anions, 8 kinds of cations with 2, 3, 4, 5, 6, 7, 8, 9, 10, or more kinds of anions, 9 kinds of cations with 2, 3, 4, 5, 6, 7, 8, 9, 10, or more kinds of anions, 10 kinds of cations with 2, 3, 4, 5, 6, 7, 8, 9, 10, or more kinds of anions, or more than 10 kinds of cations with 2, 3, 4, 5, 6, 7, 8, 9, 10, or more kinds of anions.

In some aspects, the disclosed double salt ionic liquids can have a structure according to the formula:

$$[nC_1 + mC_2][xM_1X_a + (1-x)M_2Y_b]$$

wherein $C_1$ and $C_2$ are cations; $M_1$ and $M_2$ are metals; $X_a$ and $Y_b$ are halides; n is a number from 0 to 5; m is a number from 0 to 5; x is a number from 0.01 to 0.99; wherein the sum of n+m is greater than 0; and wherein at least one of $C_1$ and $C_2$ comprises an organic cation. In some examples, x can be a number from 0.05 to 0.95; 0.1 to 0.9; 0.15 to 0.85; 0.2 to 0.8; 0.25 to 0.75; 0.3 to 0.7; 0.35 to 0.65; 0.4 to 0.6; 0.45 to 0.55; 0.5 to 0.5; 0.55 to 0.45; 0.6 to 0.4; 0.65 to 0.35; 0.7 to 0.3; 0.75 to 0.35; 0.8 to 0.2; 0.85 to 0.15; 0.9 to 0.1; 0.05 to 0.95, and anything in-between, so that the net charge of the ionic liquid is zero. In some examples, n and m are each independently a number from 0 to 4.95; 0 to 4; 0 to 3.5; 0 to 3; 0 to 2.5; 0 to 2; 0 to 1.5; 0 to 1; 0 to 0.5; 0 to 3.5; and anything in-between, so that the net charge of the ionic liquid is zero. Some examples of double salt ionic liquids are given in Table 1.

Compositions comprising the ionic liquids described herein are also disclosed. The compositions can include, in addition to the cations and anions, nonionic species, such as a solvent. The amount of such nonionic species can be (e.g., less than about 99, 95, 90, 80, 70, 60, 50, 40, 30, 20, 10, 5, or 1 wt. % based on the total weight of the composition). In some examples described herein, the disclosed ionic liquid compositions are neat; that is, the only materials present in the disclosed ionic liquids are the cations and anions that make up the ionic liquid (the salt itself). It is understood, however, that even with neat ionic liquids, some additional materials or impurities can sometimes be present, albeit at low to trace amounts (e.g., less than about 10, 9, 8, 7, 6, 5, 4, 3, 2, or 1 wt. % based on the total weight of the composition).

TABLE 1

Double Salt Ionic Liquids

| Class | Anions | Example | Composition |
|---|---|---|---|
| Triethylammonium [chloroaluminate-chlorozinchate] | $[(1 - x)Al_2Cl_7 + xZnCl_4]$ | 1-I | $[HN_{222}]_{1.50}[0.50Al_2Cl_7 + 0.50ZnCl_4]$ |
| | | 1-II | $[HN_{222}]_{1.40}[0.60Al_2Cl_7 + 0.40ZnCl_4]$ |
| | | 1-III | $[HN_{222}]_{1.33}[0.67Al_2Cl_7 + 0.33ZnCl_4]$ |
| | | 1-IV | $[HN_{222}]_{1.30}[0.70Al_2Cl_7 + 0.30ZnCl_4]$ |
| | | 1-V | $[HN_{222}]_{1.10}[0.90Al_2Cl_7 + 0.10ZnCl_4]$ |
| Triethylammonium [chloroaluminate-chloroferrate] | $[(1 - x)AlCl_4 + xFeCl_4]$ | 2-I | $[HN_{222}][0.20AlCl_4 + 0.80FeCl_4]$ |
| | | 2-III | $[HN_{222}][0.25AlCl_4 + 0.75FeCl_4]$ |
| | | 2-III | $[HN_{222}][0.33AlCl_4 + 0.67FeCl_4]$ |
| | | 2-IV | $[HN_{222}][0.40AlCl_4 + 0.60FeCl_4]$ |
| | | 2-V | $[HN_{222}][0.50AlCl_4 + 0.50FeCl_4]$ |
| | | 2-VI | $[HN_{222}][0.60AlCl_4 + 0.40FeCl_4]$ |
| | | 2-VII | $[HN_{222}][0.67AlCl_4 + 0.33FeCl_4]$ |
| | | 2-VIII | $[HN_{222}][0.80AlCl_4 + 0.20FeCl_4]$ |
| Triethylammonium [chloroaluminate-chloroferrate] | $[(1 - x)Al_2Cl_7 + xFeCl_4]$ | 3-I | $[HN_{222}][0.50Al_2Cl_7 + 0.50FeCl_4]$ |
| Triethylammonium [chlorozinckate-[chloroferrate] | $[(1 - x)ZnCl_4 + xFeCl_4]$ | 4-I | $[HN_{222}]_{1.5}[0.50ZnCl_4 + 0.50FeCl_4]$ |
| Triethylammonium [chloroaluminate-chlorozinchate] | $[(1 - x)Al_2Cl_7 + xZnCl_3]$ | 5-I | $[HN_{222}][0.33Al_2Cl_7 + 0.67ZnCl_3]$ |
| Triethylammonium [chloroaluminate-hydrogensulfate] | $[(1 - x)Al_2Cl_7 + xHSO_4]$ | 6-I | $[HN_{222}][0.8Al_2Cl_7 + 0.2HSO_4]$ |
| | | 6-II | $[HN_{222}][0.67Al_2Cl_7 + 0.33HSO_4]$ |
| | | 6-III | $[HN_{222}][0.5Al_2Cl_7 + 0.5HSO_4]$ |
| | | 6-IV | $[HN_{222}][0.33Al_2Cl_7 + 0.67HSO_4]$ |
| Triethylammonium [chloroaluminate-chloroferrate] | $[(1 - x)AlCl_4 + xFeCl_3]$ | 7-I | $[HN_{222}]_{0.5}[0.50AlCl_4 + 0.50FeCl_3]$ |
| Triethylammonium [chlorozinckate-chloroaluminate] | $[(1- x)ZnCl_4 + xAlCl_3]$ | 8-I | $[HN_{222}][0.5AlCl_3 + 0.5ZnCl_4]$ |
| | | 8-II | $[HN_{222}]_{0.8}[0.6AlCl_3 + 0.4ZnCl_4]$ |
| | | 8-III | $[HN_{222}]_{0.66}[0.67AlCl_3 + 0.33ZnCl_4]$ |

Methods for Preparing the Compositions

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the active herbicides, and other biological agents disclosed herein can be obtained from commercial sources.

The disclosed ionic liquid and double salt ionic liquid compositions can be prepared by methods described herein. Generally, the particular cation(s) and anion(s) used to prepare the disclosed ionic liquids are selected as described herein. With the particular cation(s) and anion(s) in hand, they can be combined, resulting in ionic liquid compositions as disclosed herein. Providing ions used to prepare the disclosed ionic liquids depends, in one aspect, on the desired properties of the resulting ionic liquid composition. As described herein, the disclosed ionic liquid compositions can have multiple desired properties, which, at least in part, come from the properties of the cation(s) and/or anion(s) used to prepare the ionic liquid. Thus, to prepare the disclosed ionic liquids, one or more kinds of cations with a desired property(ies) are provided.

In some aspects, the double salt ionic liquids can be prepared with at least one cation and two or more anions, as described in the methods below. Such methods can include mixing of two ionic liquids.

In some embodiments, the double salt ionic liquids can be prepared by mixing two or more ionic liquids with a different anion identity (Scheme 1). The general formula of the double salt ionic liquids can be $[nC_1+mC_2][xM_1X_a+(1-x)M_2Y_b]$; wherein $C_1$ and $C_2$ are cations (not necessarily the same); $M_1$ and $M_2$ are metals; and $X_a$ and $Y_b$ are halides (not necessarily the same). Unlike in the case of the mixing of two solutions, the mixing of two ionic liquids results in a compound where the anions interact with one another. This results in a compound with a unique set of properties, such as melting point, viscosity, density, thermal decomposition, and water solubility with respect to the constituent salts.

In some embodiments, the molar ratio of the two or more ionic liquids used to form the double salt ionic liquid can be 1:1 or greater. For example, the molar ratio of the two or more ionic liquids used to form the double salt ionic liquid can be 1:1.2 or greater, 1:1.3 or greater, 1:1.4 or greater, 1:1.5 or greater, 1:1.6 or greater, 1:1.7 or greater, 1:1.8 or greater, 1:1.9 or greater, 1:2 or greater, 1:2.3 or greater, 1:2.5 or greater, 1:2.8 or greater, 1:3 or greater, 1:4 or greater, 1:5 or greater, 1:6 or greater, 1:7 or greater, 1:8 or greater, 1:9 or greater, 1:10 or greater, 1:20 or greater, 1:30 or greater, 1:40 or greater, 1:50 or greater, 1:60 or greater, 1:70 or greater, 1:80 or greater, 1:90 or greater, or 1:99 or greater. In some embodiments, the molar ratio of the two or more ionic liquids used to form the double salt ionic liquid can be 1:20 or less, 1:15 or less, 1:10 or less, 1:9 or less, 1:8 or less, 1:7 or less, 1:6 or less, 1:5 or less, 1:4 or less, 1:3 or less, 1:2.5 or less, 1:2 or less, 1:1.9 or less, 1:1.8 or less, 1:1.7 or less, 1:1.5 or less, 1:1.3 or less, 1:1.2 or less, or 1:1 or less. In some embodiments, the molar ratio of the two or more ionic liquids used to form the double salt ionic liquid can be 1:1 to 1:20, from 1:1 to 1:10, from 1:1 to 1:8, from 1:1 to 1:6, from 1:1 to 1:5, from 1:1 to 1:4, from 1:1 to 1:3, or from 1:1 to 1:2, and anything in-between.

No solvent is required, but it can be utilized if the salts are solid at room temperature or possess a high viscosity. When a solvent is utilized to improve mixing, it can be removed by reduced pressure.

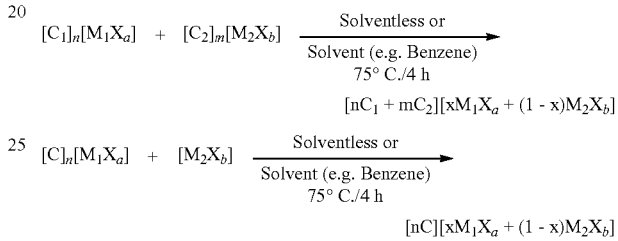

Scheme 1. General reaction scheme to prepare double salt ionic liquids by nonstoichiometric addition of salts or addition of neutral metal halides to ionic liquids.

As noted herein, providing a suitable ion can be based on selecting an ion that possesses a property that is desired (e.g., the ion has a property that is desired to be possessed by the resulting ionic liquid). Examples of properties that could be desired in a suitable cation and/or anion (and thus the ionic liquid made therefrom) include, but are not limited to, acidity, solubility, miscibility, and/or catalytic activity. While more specific properties are disclosed elsewhere herein, the disclosed methods and compositions are not limited to any particular combination of properties, as such will depend on the preferences and goals of the practitioner.

In some embodiments, the combination of two or more metal-containing salts to form double salt ionic liquids can lead to materials which are both new materials of matter and have different acidity and catalytic properties compared to the parent compounds. The pH of the double salt ionic liquid compositions disclosed herein can be 6.5 or less, 6 or less, 5.5 or less, 5 or less, 4.5 or less, 4 or less, 3.5 or less, 3 or less, 2.5 or less, 2 or less, 1.5 or less, or 1 or less. In some embodiments, the pH of the double salt ionic liquid compositions can be from 0 to 6.5, from 0 to 6, from 0 to 5.5, from 0 to 5, from 1 to 6.5, from 1 to 6, from 1 to 5.5, from 1 to 5, or from 1 to 4. In some embodiments, the reaction between the two or more salts at any ratio (not necessarily stoichiometric) can lead to an infinite number of new compounds which can be useful as tunable Lewis acid catalysts. Evidence for the formation of new species in the double salt ionic liquids include: (a) changes in physical state and color of the compound compared to their precursors, and (b) analytical data (nuclear magnetic resonance (such as $^1H$, $^{13}C$, or $^{27}Al$ NMR).

The disclosed ionic liquids are liquid at some temperature range or point at or below about 150° C. For example, the disclosed ionic liquids can be a liquid at or below about 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0, −1, −2, −3, −4, −5, −6, −7, −8, −9, −10, −11, −12, −13, −14, −15, −16, −17, −18, −19, −20, −21, −22, −23, −24, −25, −26, −27, −28, −29, or −30° C., where any of the stated values can form an upper or lower endpoint when appropriate. In further examples, the disclosed ionic liquids can be liquid at any point from about −30° C. to about 150° C., from about −20° C. to about 140° C., −10° C. to about 130° C., from about 0° C. to about 120° C., from about 10° C. to about 110° C., from about 20° C. to about 100° C., from about 30° C. to about 90° C., from about 40° C. to about 80° C., from about 50° C. to about 70° C., from about −30° C. to about 50° C., from about −30° C. to about 90° C., from about −30° C. to about 110° C., from about −30° C. to about 130° C., from about −30° C. to about 150° C., from about 30° C. to about 90° C., from about 30° C. to about 110° C., from about 30° C. to about 130° C., from about 30° C. to about 150° C., from about 0° C. to about 100° C., from about 0° C. to about 70° C., from about 0° to about 50° C., and the like.

Further, in some examples the disclosed ionic liquid compositions can be liquid over a wide range of temperatures, not just a narrow range of, say, 1-2 degrees. For example, the disclosed ionic liquid compositions can be liquids over a range of at least about 4, 5, 6, 7, 8, 9, 10, or more degrees. In other example, the disclosed ionic liquid compositions can be liquid over at least about 11, 12, 13, 14, 15, 16, 17, 18, 19, 20, or more degree temperature range. Such temperature ranges can begin and/or end at any of the temperature points disclosed in the preceding paragraph.

In many examples disclosed herein the disclosed ionic liquid compositions are liquid at the temperature at which they will be used or processed (e.g., ambient temperature). In still other examples, the disclosed compositions can be liquid at the temperature at which they are formulated or processed.

Methods of Use

Ionic liquids have been of general interest because they are environmentally-friendly alternatives to organic solvents for various chemical processes, e.g., liquid/liquid extractions, catalysis, separations, and electrochemistry. Ionic liquids have also become popular alternative media for chemical synthesis because of their low volatility and low toxicity. See e.g., Wasserscheid and Keim, *Angew Chem Int Ed Engl*, 2000, 39:3772; and Wasserscheid, "Ionic Liquids in Synthesis," 1$^{st}$ Ed., Wiley-VCH, 2002. Further, ionic liquids can reduce costs, disposal requirements, and hazards associated with volatile organic compounds. Other exemplary properties of ionic liquids are high ionic conductivity, non-volatility, non-flammability, high thermal stability, wide temperature for liquid phase, highly solvability, and non-coordinating. For a review of ionic liquids see, for example, Welton, *Chem Rev.* 1999, 99:2071-2083; and Carlin et al., Advances in Nonaqueous Chemistry, Mamantov et al. Eds., VCH Publishing, New York, 1994.

The specific physical properties (e.g., melting point, viscosity, density, water solubility, acidity, etc.) of ionic liquids are determined by the choice of cation and anion, as is disclosed more fully herein. As an example, the melting point for an ionic liquid can be changed by making structural modifications to the ions or by combining different ions. Similarly, the particular chemical properties (e.g., catalytic activity), can be selected by changing the constituent ions of the ionic liquid.

The disclosed double salt ionic liquid compositions have many uses. In some embodiments, the double salt ionic liquid compositions can be used as a catalyst. Methods of catalyzing a chemical reaction using the double salt ionic liquids described herein are disclosed. The method can include contacting the double salt ionic liquid with a reactant. In some embodiments, the chemical reaction can be an acid catalyzed chemical reaction. For example, the acid catalyzed chemical reaction can be a Lewis acid catalyzed reaction chosen from Friedel Crafts alkylation or acylation, or similar reactions with carbonyl-containing substrates, Diels-Alder reactions, addition and conjugate addition to carbonyl compounds, addition of silyl enol ethers and allylsilanes to carbonyl compounds, a carbonyl-ene reaction, a Beckmann rearrangement reaction, a reaction for biodiesel production, a mercury-catalyzed type reaction, or a hydrogen-fluoride catalyzed type reaction. In some examples the methods for catalyzing a chemical reaction using the double salt ionic liquids further includes recycling the catalyst for subsequent use.

Methods for enhancing the catalytic activity of an ionic liquid are also disclosed. The method can include converting a metal halide ionic liquid or Lewis acid ionic liquid compound into a double salt ionic liquid by introducing a second ion, which allows for enhancement of the catalytic activity of the ionic liquid.

Without wishing to be bound by theory, the cations and anions that form the double salt ionic liquid allows the tuning of the acidity, rate of dissolution, solubility, miscibility, and availability of the double salt ionic liquids, and thus control of catalytic performance. In particular, because the double salt ionic liquids are liquids at reaction conditions, the metallic ions can be combined at any ratio within their limits of solubility or miscibility, allowing (a) tunable acidity through varying the ratios of metals resulting in an increased efficiency over a variety of catalytic reactions, (b) low vapor pressure, which increases safety when compared to the use of highly toxic and volatile HF, and (c) the ability to act as both homogeneous and heterogeneous catalysts (when applied to solid support phases). Heterogeneous catalysts combine the advantages of solid phase catalysts with the kinetics of homogeneous catalysts. This provides more efficient catalytic process applicable to many acidic catalysts.

EXAMPLE

The following examples are set forth below to illustrate the compositions, methods, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Synthesis and Characterization of DSIL: Triethylammonium [Chloroaluminate-Chlorozincate] $\{[HN_{222}]_{(1+x)}[Al_2Cl_7+xZnCl_4]\}$ Under Solventless Conditions Experimental: For the synthesis of $[HN_{222}]_{(1+x)}[(1-x)Al_2Cl_7+xZnCl_4]$ DSIL, a very faint brown liquid $[HN_{222}][Al_2Cl_7]$ was placed into a 20 mL screw top borosilicate glass vial and white solid $[HN_{222}]_2[ZnCl_4]$ was added under flow of argon (using a glove bag). The screw top vial was equipped with Teflon coated magnetic stir bar. After addition of the reactants, the vial was capped using a cap with a Teflon/silicon (10/90) septum, and sealed with Parafilm. The vial was then removed from the glove bag and the reaction mixture was heated in a temperature controlled oil bath with magnetic stirring at 75° C. for 4 h (Scheme 2).

Scheme 2. Reaction scheme to prepare
$[HN_{222}]_{(1+x)}[(1-x)Al_2Cl_7+xZnCl_4]$
DSIL by nonstoichiometric addition of metal salts.

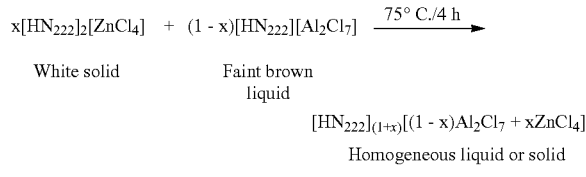

By following the above procedure, $[HN_{222}]_{(1+x)}[(1-x)Al_2Cl_7+xZnCl_4]$ DSILs were prepared with different molar fraction (x) of the metal salts. Observations are summarized in Table 2. When the metal salts were combined in the range of x=0.1 to 0.6, homogeneous liquid or solid DSILs were obtained. Changes in the physical state (such as melting point) and color of the system indicated a possible formation of new species in the DSIL. These DSILs were characterized by several spectroscopic techniques which are explained below.

Table 2 summarizes the observed changes on the DSIL.

TABLE 2

$[HN_{222}]_{(1+x)}[(1-x)(Al_2Cl_7) + x(ZnCl_4)]$ DSIL prepared under solventless at 75° C. for 4 h

| | Physical Observations | | |
|---|---|---|---|
| Composition (x) | After addition (room temperature) | After heating (75° C., 1 to 4 h) | After cooling (to room temperature) |
| 0.0 | | Faint brown liquid | |
| 0.1 | Brown liquid + some white solid | Gray viscous liquid | |
| 0.2 | | | |
| 0.3 | | Milky white liquid | Milky white solid** |
| 0.33 | | Brown liquid | Gray crystalline solid* |
| 0.4 | | | |
| 0.5 | Faint brown viscous liquid + white solid | Pink liquid | |
| 0.6 | | Viscous faint yellow liquid | |
| 0.67 | | Mixture of light pink at the bottom + solid at the top ($[HN_{222}][ZnCl_4]$) | |
| 0.8 | | | |
| 0.9 | | | |
| 1.0 | | White solid | |

Where x is molar fraction of $[HN_{222}]_2[ZnCl_4]$ in $[HN_{222}]_{(1+x)}[(1-x)(Al_2Cl_7) + x(ZnCl_4)]$ system;
*Crystal formation when cool to RT;
**Solid formation when cool to RT.

Characterization: Table 3 summarizes the results obtained with the analytical techniques used for characterization of the $[HN_{222}]_{(1+x)}[(1-x)(Al_2Cl_7)+x(ZnCl_4)]$ system. All characterization details are provided below.

TABLE 3

Summary of the results obtained during characterization of the $[HN_{222}]_{(1+x)}[(1 - x)(Al_2Cl_7) + x(ZnCl_4)]$ system

| Characterization technique | Composition (x) | |
|---|---|---|
| | 0.1-0.3 | 0.4   0.5 |
| $^{27}$Al NMR | Two peaks were observed (at 96 and 104 ppm), indicating two types of Al species. | One peak was observed (at 104 ppm) indicating one type of Al species. |
| $^1$H NMR | A significant change in the chemical shift of NH proton indicates a change in N atom's electronic environment. Very slight change in the chemical shift of $CH_3$ and $CH_2$ protons of ethyl group on ammonium cation was also observed. | |
| $^{13}$C NMR | A significant upfield shift of $CH_3$ and $CH_2$ carbon atoms of ethyl group on ammonium cation was observed when the composition (ratio) was changed indicates a change in ethyl carbon atoms' electronic environment. | |

$^{27}$Al NMR: To identify the species present in $[HN_{222}]_{(1+x)}[(1-x)Al_2Cl_7+xZnCl_4]$ DSIL, samples were characterized by $^{27}$Al NMR under solventless (using dimethyl xulfoxide-$d_6$ as an external lock solvent, represented here as DMSO-$d_6$) at 55° C. The pure $[HN_{222}][Al_2Cl_7]$ has two Al signals in $^{27}$Al NMR spectrum, one of which is symmetric tetrahedral Al (likely $[AlCl_4]^-$, [J. Am. Chem. Soc. (1981), 103, 7147-7151]) and the other is non-linear corner sharing tetrahedral $C_2$ geometry Al (likely $[Al_2Cl_7]^-$, [J. Am. Chem. Soc. (1981), 103, 7147-7151]). Upon addition of $[HN_{222}]_2[ZnCl_4]$, non-linear corner sharing tetrahedral $C_2$ peak disappears and is no longer detected in the salts with x higher than 0.33, indicating disappearance of $[Al_2Cl_7]^-$ species (FIG. 1).

Figure 2:
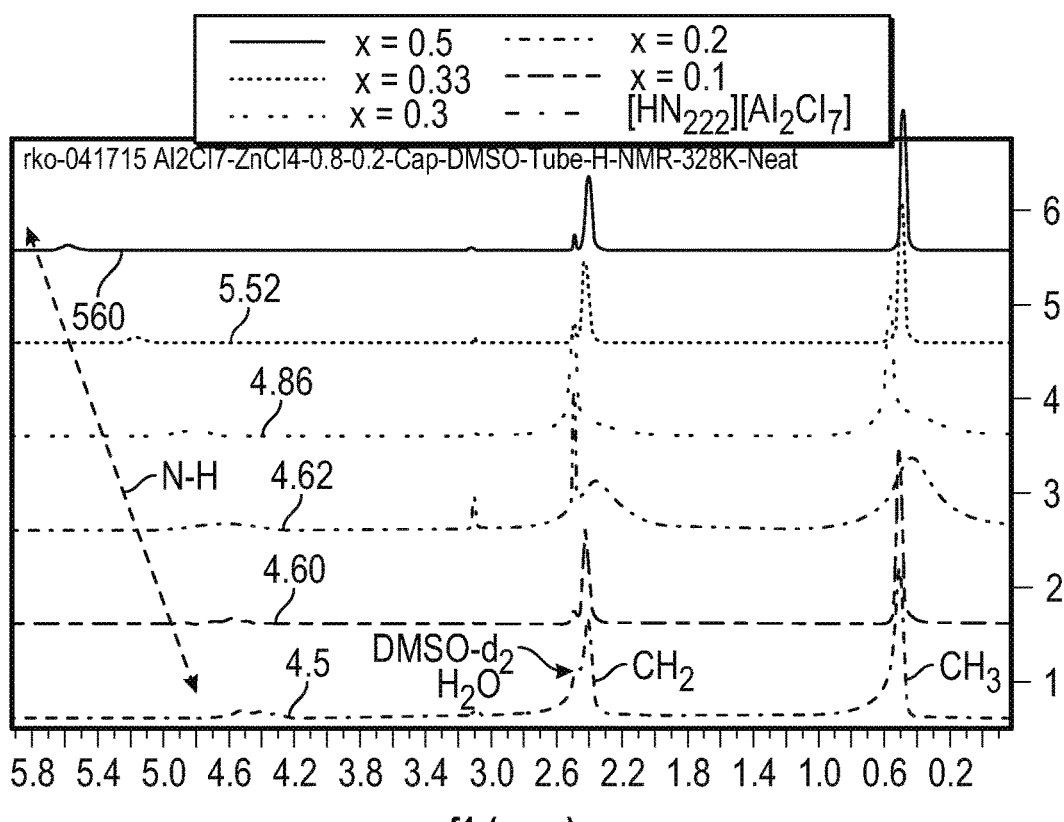
FIG. 2 is a $^1H$ NMR spectrum of $[HN_{222}]_{(1+x)}[(1-x)Al_2Cl_7+xZnCl_4]$ with different molar fraction (55° C., neat, DSMO-$d_6$ lock); where x=0, the molecule is $[HN_{222}][Al_2Cl_7]$.

$^1$H NMR: DSIL were also characterized by solventless $^1$H NMR (using DMSO-$d_6$ as an external lock solvent) at 55° C. There was observed slight change in the chemical shift of $CH_3$ and $CH_2$ protons of the ethyl group from ammonium cation (irregular, both upfield and downfield shift), and a significant change in the location of N—H proton in $[HN_{222}][(1-x) Al_2Cl_7+xZnCl_4]$ DSIL, with increasing the molar ratio of Al. Typically N—H is considered to be an "exchangeable proton" and usually might appear at any place on the ppm scale from 4 ppm to 11 ppm. The $^1$H shift of N—H proton could be either attributed to its "exchange" property or to changes in the speciation (FIG. 2).

Figure 3:
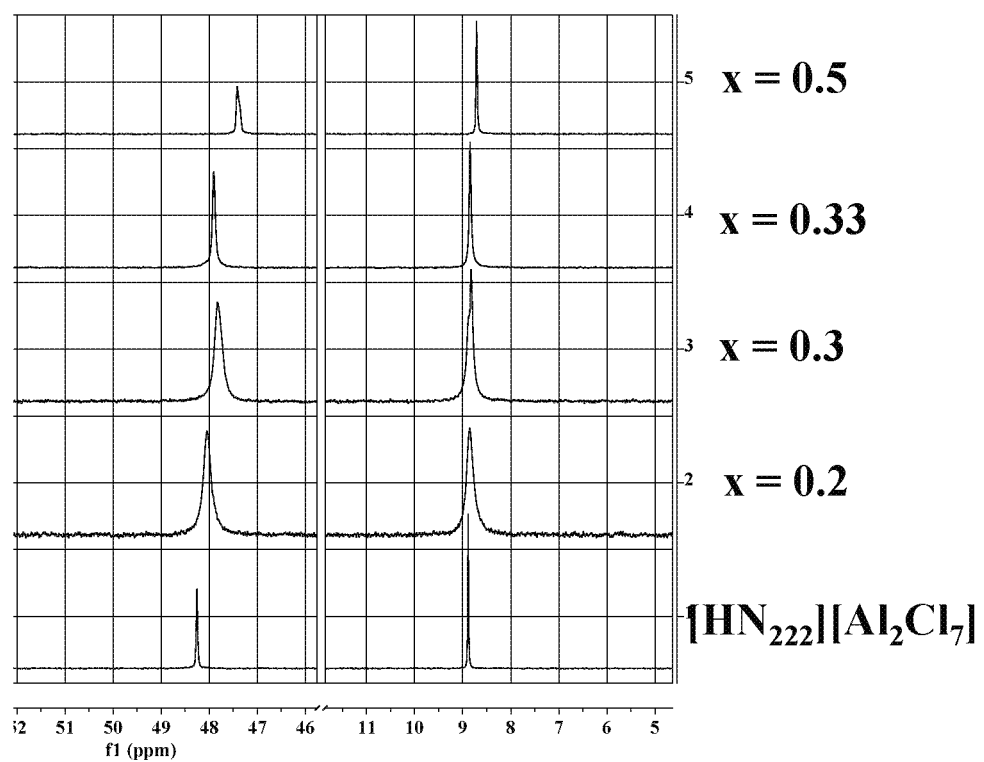
FIG. 3 is a $^{13}C$ NMR spectrum of $[HN_{222}]_{(1+)}[(1-x)Al_2Cl_7+xZnCl_4]$ with different molar fraction (55° C., neat, DSMO-$d_6$ lock); where x=0, the molecule is $[HN_{222}][Al_2Cl_7]$.

$^{13}$C NMR: DSIL were also characterized by solventless $^{13}$C NMR at 55° C., and it was found that there is a significant large chemical shift in the $^{13}$C NMR peaks for $CH_3$ and $CH_2$ protons of ethyl group on ammonium cation in $[HN_{222}]_{(1-x)}[(1-x)Al_2Cl_7+xZnCl_4]$ DSIL (FIG. 3), for all different compositions. Specifically, as the molar ratio of Al in the DSIL decreases, an upfield shift in the $^{13}$C NMR peaks was observed.

Figure 4:
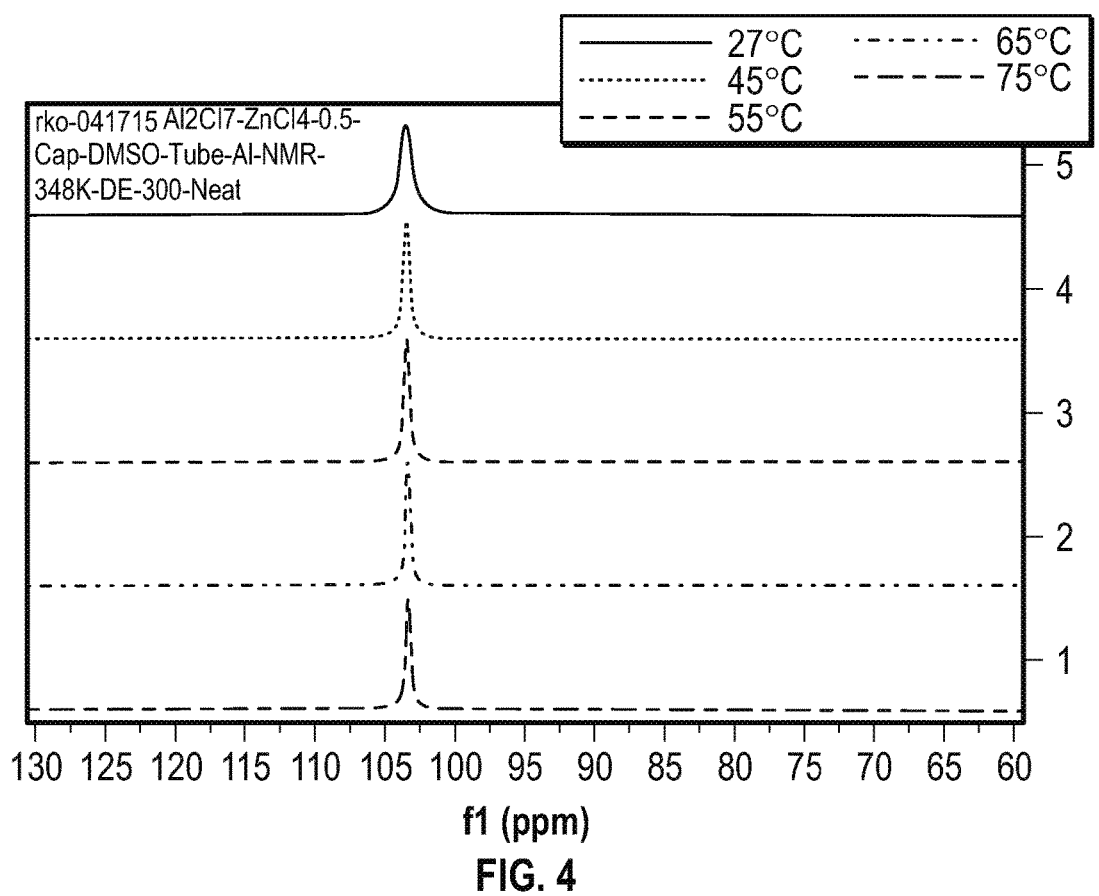
FIG. 4 is an $^{27}Al$ NMR spectrum of $[HN_{222}]_{1.5}[0.5Al_2Cl_7+0.5ZnCl_4]$ at different NMR instrument temperature (27-65° C., neat, DSMO-$d_6$ lock).

Temperature effect on the chemical shift in $^{27}$Al NMR and $^1$H NMR ($[HN_{222}]_{1.5}[0.5Al_2Cl_7+0.5ZnCl_4]$, x=0.5 as example), to study the effect of temperature on both cation and anion: To investigate the effect of temperature on the chemical shift of aluminum, we studied the $^{27}$Al NMR of $[HN_{222}]_{1.5}[0.5Al_2Cl_7+0.5ZnCl_4]$ at various NMR instrument temperatures (FIG. 4). as the temperature of the probe of NMR-instrument decreased, the Al peak position does not change, indicating no change in speciation upon temperature change (i.e. in the system x=0.5 the speciation does not depend on temperature) and peaks became broader due to the higher viscosity of the DSIL at lower temperatures (FIG. 4).

Figure 5:
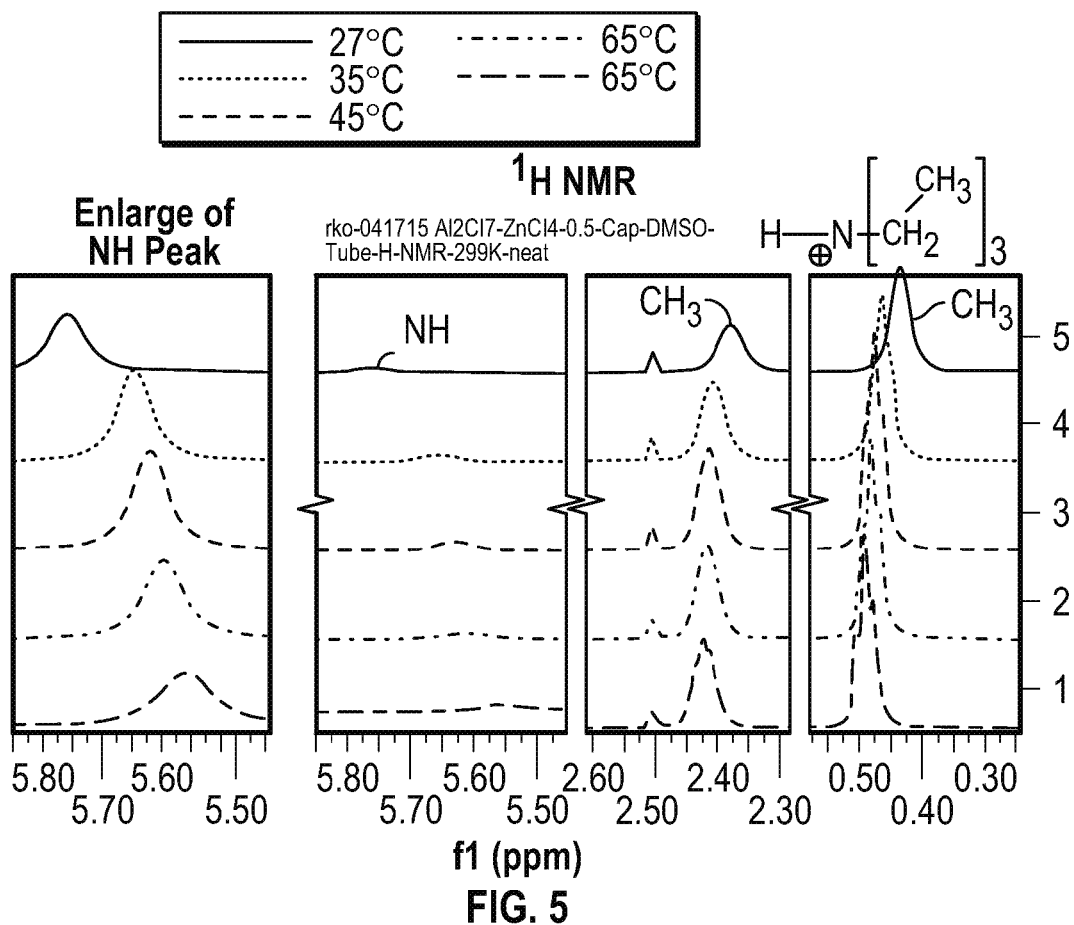
FIG. 5 is a $^1H$ NMR spectrum of $[HN_{222}]_{1.5}[0.5Al_2Cl_7+0.5ZnCl_4]$ at different NMR instrument temperature (27-65° C., neat, DSMO-$d_6$ lock).

On the example of DSIL with x=0.5, by reducing the temperature of NMR probe, there was observed a downfield shift of N—H peak, and an upfield shift of $CH_3$ and $CH_2$ protons of ethyl group (FIG. 5).

To see if there is any difference in the $[HN_{222}]_{1.5}$ $[0.5Al_2Cl_7+0.5ZnCl_4]$ when DSIL is prepared neat or in benzene as a solvent, this system was prepared using benzene and compared with the corresponding DSIL prepared under solventless conditions.

For the synthesis of $[HN_{222}]_{1.5}[0.5Al_2Cl_7+0.5ZnCl_4]$, 2 mmol of faint brown liquid $[HN_{222}][Al_2Cl_7]$ was placed into a 5 mL screw top vial and 2 mmol of white solid $[HN_{222}]_2[ZnCl_4]$ was added under flow of argon (using a glove bag). After that, 2 g benzene were added to the vial. (When benzene was added, a biphasic system (liquid clathrate) was formed immediately.) The screw top vial was equipped with Teflon coated magnetic stir bar. After addition of the reactants, the vial was capped using a cap with a Teflon/silicon (10/90) septum, and sealed with Parafilm. The vial was then removed from the glove bag and the reaction mixture was heated in a temperature controlled oil bath with magnetic stirring at 75° C. for 4 h (Scheme 2, Section 1).

After 4 h, the two phases were separated using a Pasteur glass pipet, and both layers were characterized by $^1H$ NMR and $^{27}Al$ NMR and compared with the corresponding DSIL prepared under solventless. Benzene layer was characterized before and after benzene removal. In Table 4, a summary on the results obtained with the analytical techniques used for characterization of the $[HN_{222}]_{1.5}[0.5Al_2Cl_7+0.5ZnCl_4]$. All characterization details are provided below.

Figure 8:
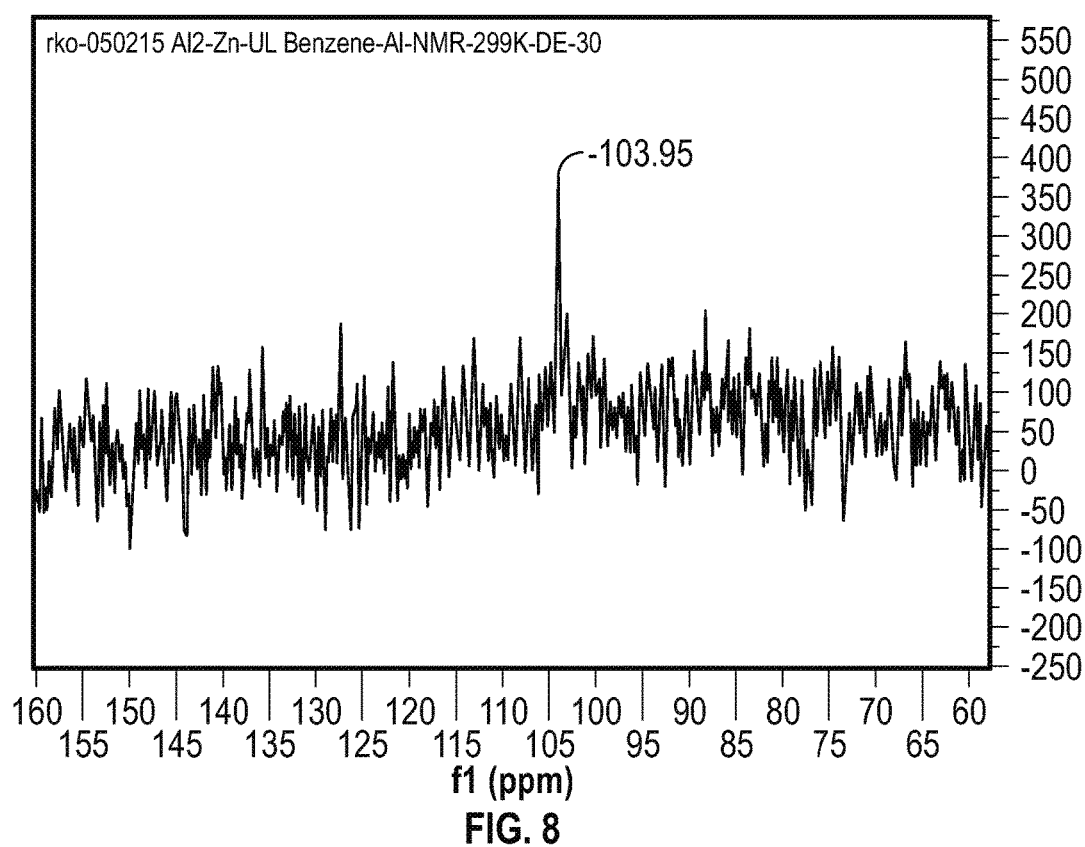
FIG. 8 is an $^{27}Al$ NMR spectrum of an upper benzene layer when $[HN_{222}]_{1.5}[0.5Al_2Cl_7+0.5ZnCl_4]$ system is prepared in benzene (27° C., neat, DSMO-$d_6$ lock).
Figure 9:
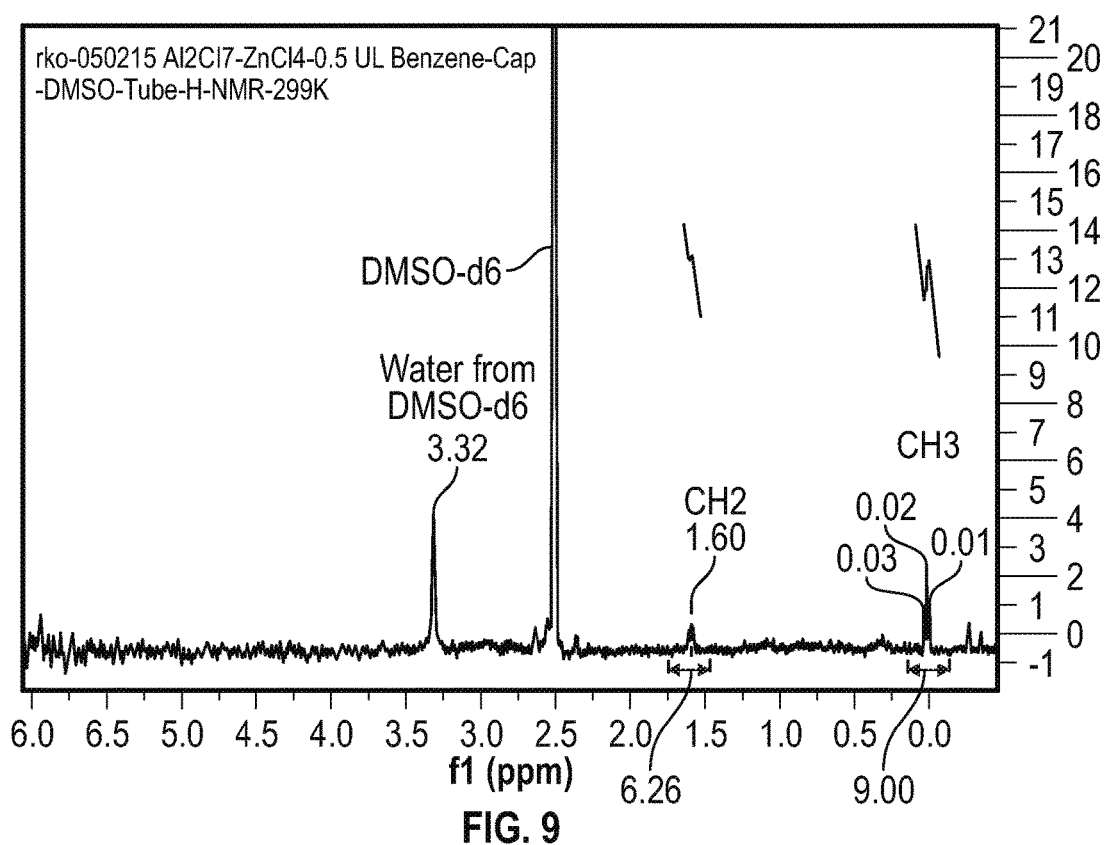
FIG. 9 is a $^1H$ NMR spectrum of an upper benzene layer when $[HN_{222}]_{1.5}[0.5Al_2Cl_7+0.5ZnCl_4]$ system is prepared in benzene (27° C., neat, DSMO-$d_6$ lock).

Upper (Benzene-Rich) Layer from the $[HN_{222}]_{1.5}$ $[0.5Al_2Cl_7+0.5ZnCl_4]$ Prepared in Benzene as a Solvent The upper layer was analyzed using $^{27}Al$ NMR and $^1H$ NMR. As can be seen in FIGS. 8 and 9, traces of the product were detected, almost undetectable by NMR (required significant increase if spectrum intensity) due to low product concentration in the upper layer.

Synthesis and Characterization of DSIL: Triethylammonium [Chloroaluminate-Chloroferrate] $\{[HN_{222}][(1-x)AlCl_4+xFeCl_4]\}$ Under Solventless Conditions For the synthesis of $[HN_{222}][(1-x)AlCl_4+xFeCl_4]$ DSIL, white solid $[HN_{222}][AlCl_{14}]$ was taken in a 20 mL sample vial and green solid $[HN_{222}][FeCl_4]$ compound was added under flow of argon (using a glove bag). The screw top vial was equipped with Teflon coated magnetic stir bar. After addition of the reactants, the vial was capped using a cap with a Teflon/silicon (10/90) septum, and sealed with Parafilm. The vial was then removed from the glove bag and heated with a temperature controlled oil bath with magnetic stirring at 75° C. for 4 h (Scheme 3).

Scheme 3. Reaction scheme to prepare
$[HN_{222}][(1 - x)AlCl_4 + xFeCl_4]$
DSIL by nonstoichiometric addition of metal salts.

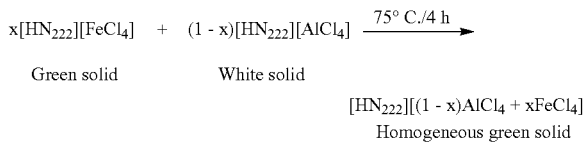

TABLE 4

Summary of the results obtained during characterization of the
$[HN_{222}]_{1.5}[0.5Al_2Cl_7 + 0.5ZnCl_4]$

| | | Using Benzene as a solvent (Liquid Clathrate) | | | |
| --- | --- | --- | --- | --- | --- |
| | | Lower layer | | Upper layer | |
| Characterization technique | Solventless | Before benzene evaporation | After benzene evaporation | Before benzene evaporation | After benzene evaporation |
| Color | Pink viscous liquid | Pink viscous liquid | Pink non-viscous liquid | Colorless liquid | Colorless liquid |
| $^{27}Al$ NMR | 1 peak observed, at 104 ppm | | | | |
| $^1H$ NMR | 3 peaks observed, at 0.44 ($CH_3$), 2.38 ($CH_2$), 5.6 (N—H) ppm | Non-comparable (solvent effect) | Same system as solventless ($[HN_{222}]^+$) | Impurities (traces) of the product were present | White solid |

Figure 6:
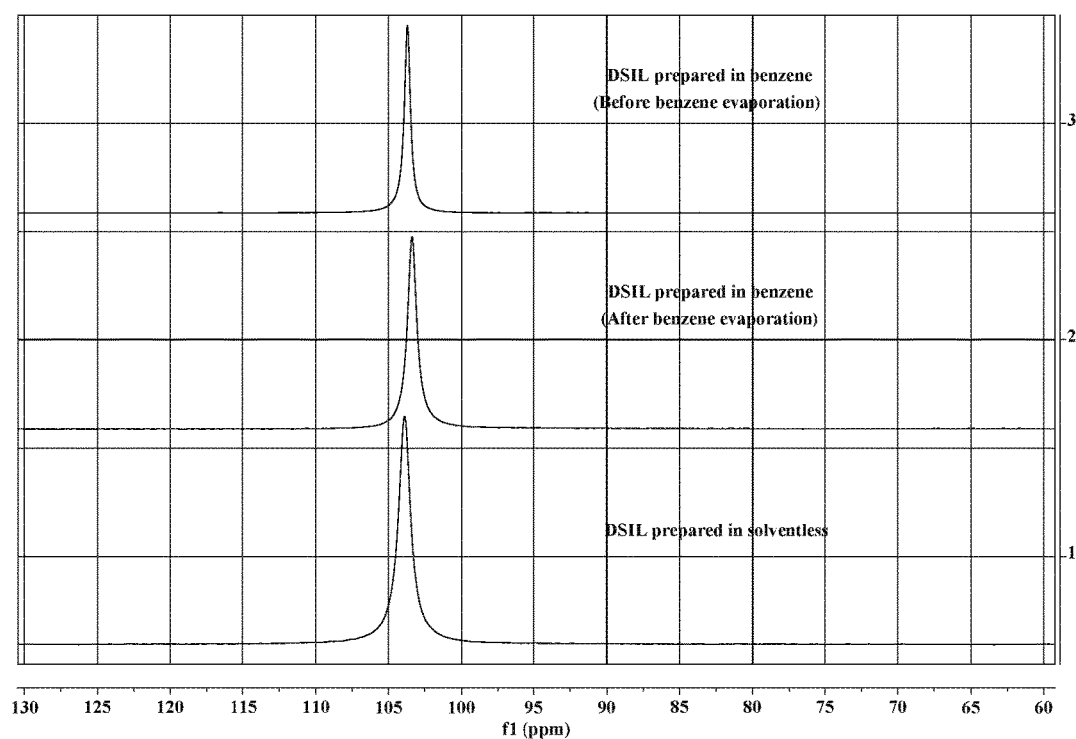
FIG. 6 is an $^{27}Al$ NMR spectrum of $[HN_{222}]_{1.5}[0.5Al_2Cl_7+0.5ZnCl_4]$ prepared in benzene before (top spectrum) and after (middle spectrum) solvent evaporation, compared with solventless (bottom spectrum) (27° C., neat, DSMO-$d_6$ lock).

Lower Layer from the $[HN_{222}]_{1.5}[0.5Al_2Cl_7+0.5ZnCl_4]$ Prepared in Benzene as a Solvent $^{27}Al$ NMR: After benzene evaporation, the pink liquid obtained appeared no different than the same system prepared solventless. The $[HN_{222}]_{1.5}[0.5Al_2Cl_7+0.5ZnCl_4]$ was thus found in the lower layer after its synthesis in benzene. $^{27}Al$ NMR indicated no change in the spectra of the DSIL when it was prepared under solventless or when it was prepared in benzene either before or after solvent removal (FIG. 6).

Figure 7:
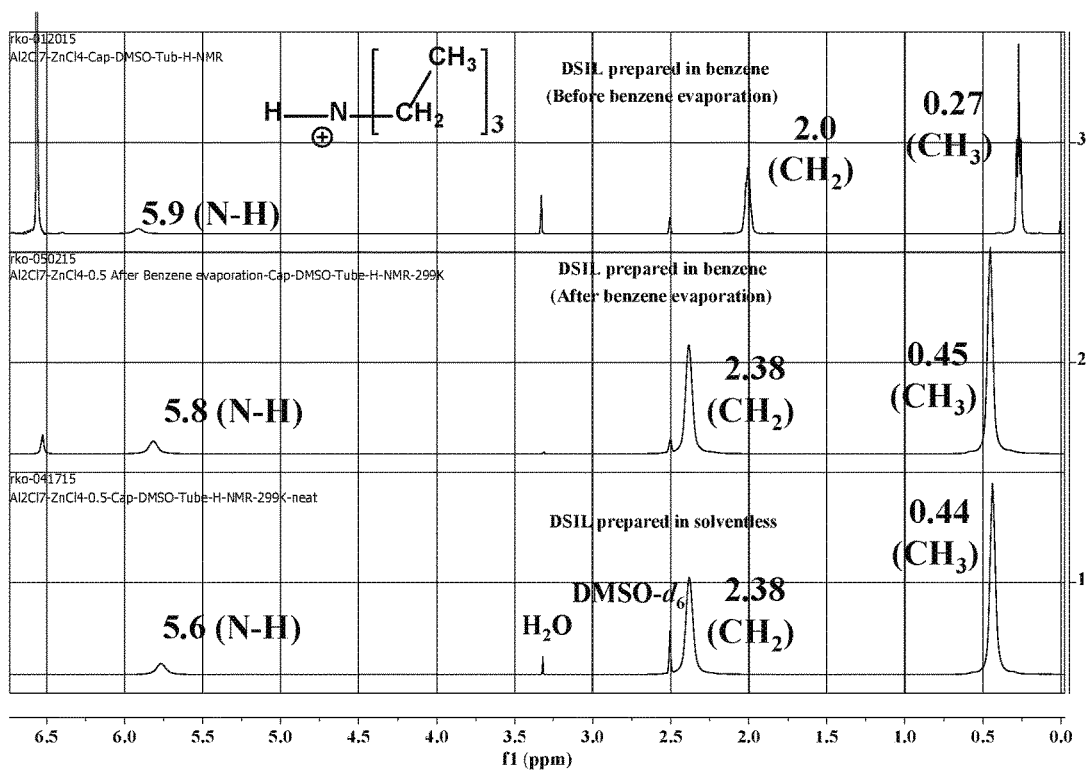
FIG. 7 is a $^1H$ NMR spectrum of $[HN_{222}]_{1.5}[0.5Al_2Cl_7+0.5ZnCl_4]$ system prepared in benzene before (top spectrum) and after (middle spectrum) solvent evaporation, compared with solventless (bottom spectrum) (27° C., neat, DSMO-$d_6$ lock).

$^1H$ NMR: $^1H$ NMR indicated no change in the spectra of $[HN_{222}]_{1.5}[0.5Al_2Cl_7+0.5ZnCl_4]$ prepared under solventless or in benzene after its evaporation. The chemical shift observed before benzene evaporation is attributed to benzene solvent effect (FIG. 7). This indicates no differences between the DSIL prepared with or without solvent.

By following the above procedure (Scheme 3) $[HN_{222}]$ $[(1-x)AlCl_4+xFeCl_4]$ DSILs were prepared in different molar fraction of the metal salts and observations are summarized in the Table 5. Homogeneous green solid (liquid at 50° C.) DSILs were formed in the entire evaluated range. The changes in their physical properties (such as mp) and color indicate a possible formation of new species in the DSIL. These DSIL were characterized by several spectroscopic techniques which are explained below. Table 5 summarizes the physical changes observed during DSIL preparation under solventless.

TABLE 5

$[HN_{222}][(1-x)(AlCl_4) + x(FeCl_4)]$ DSIL prepared under solventless at 75° C. for 4 h

| | Physical Observations | | |
|---|---|---|---|
| Composition (x) | After addition (room temperature) | After heating (75° C., 1 to 4 h) | After cooling (to room temperature) |
| 0.0 | | White solid | |
| 0.2 | Mixture of white and green solids | Yellow liquid | Homogeneous green solid |
| 0.33 and 0.4 | | Green liquid | |
| 0.5, 0.6, 0.67, 0.75, and 0.8 | | Dark green liquid | |
| 1.0 | | Green solid | |

Table 6 summarizes the results obtained with the analytical techniques used for characterization of the $[HN_{222}][(1-x)AlCl_4+xFeCl_4]$ DSIL. All characterization details are provided below.

TABLE 6

Summary of the results obtained during characterization of the $[HN_{222}][(1-x)AlCl_4 + xFeCl_4]$ DSIL

| Characterization technique | Modifying the composition (x) in $[HN_{222}][(1-x)AlCl_4 + xFeCl_4]$ system |
|---|---|
| $^{27}$Al, $^{1}$H, $^{13}$C, NMR | Significant downfield shift of Al/H/C peak when the ratio of Al in the DSIL composition was increased |
| Temperature related $^{1}$H and $^{27}$Al NMR | Significant downfield shift with temperature increase |

Figure 10:
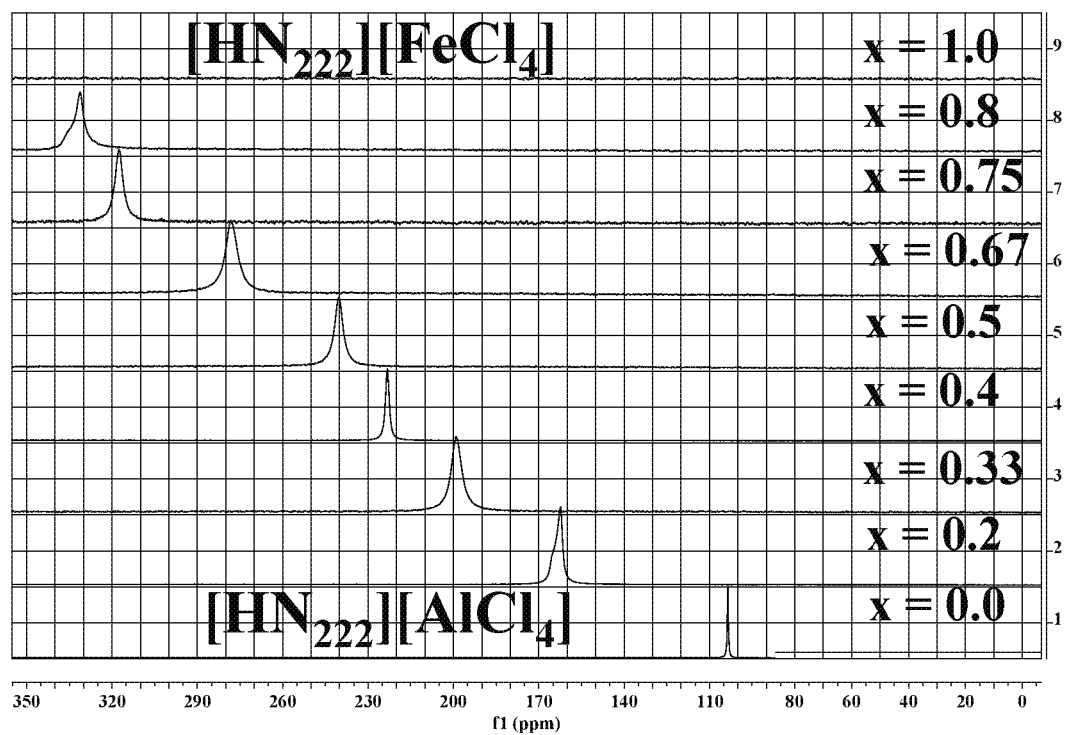
FIG. 10 is an $^{27}Al$ NMR spectrum of $[HN_{222}][(1-x)AlCl_4+xFeCl_4]$ with different molar fraction (55° C., neat, DSMO-$d_6$ lock).

$^{27}$Al NMR: To identify the speciation in $[HN_{222}][(1-x)AlCl_4+xFeCl_4]$ DSIL, samples were characterized by $^{27}$Al NMR (external lock with DMSO-$d_6$ at 55° C.). In $^{27}$Al NMR a single peak was detected independently on the composition, however a graduate downfield chemical shift was observed with increase of amount of FeCl$_4$; the dependence of chemical shift (represented as $\Delta\delta_{Al}$ in FIG. 10) on FeCl$_4$ composition was linear.

Figure 11:
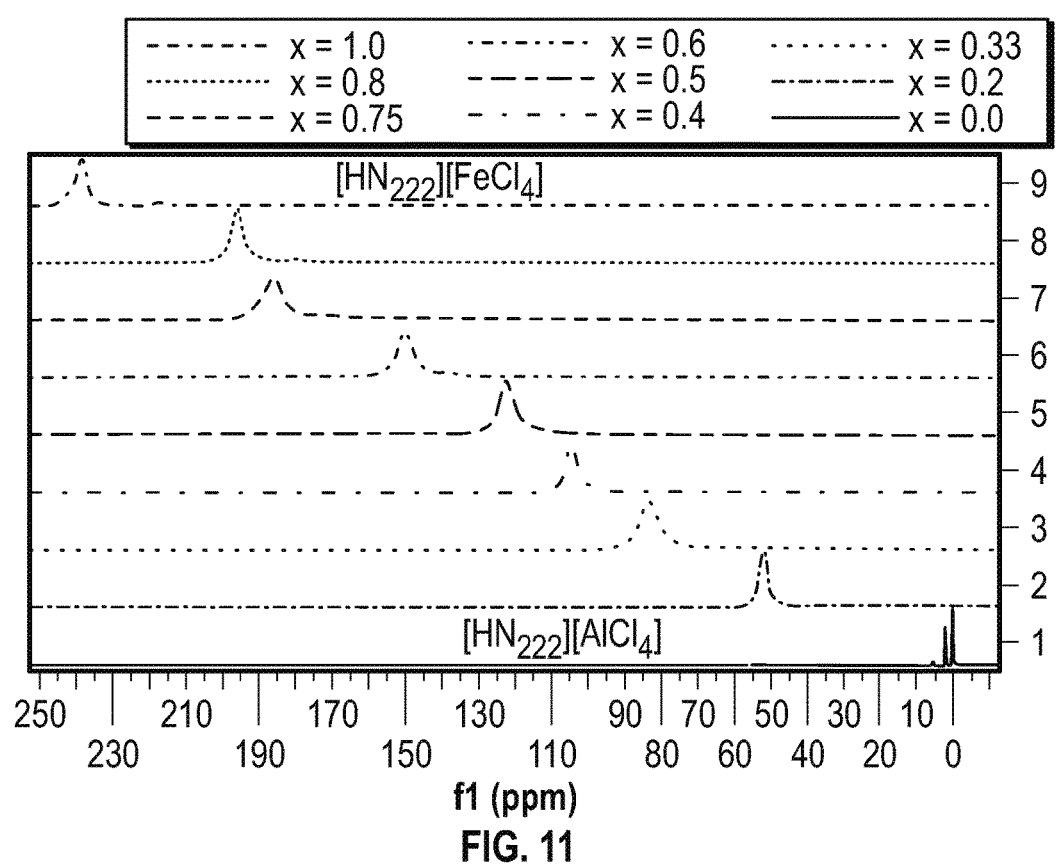
FIG. 11 is a $^{27}Al$ NMR spectrum of $[HN_{222}][(1-x)AlCl_4+xFeCl_4]$ with different molar fraction (55° C., neat, DSMO-$d_6$ lock).

$^{1}$H NMR: DSIL were also characterized by $^{1}$H NMR under solventless (using DMSO-$d_6$ as an external lock solvent) at 55° C. and a graduate downfield chemical shift was observed with increase of amount of FeCl$_4$; the dependence of chemical shift on FeCl$_4$ amount was linear (FIG. 11).

Figure 12:
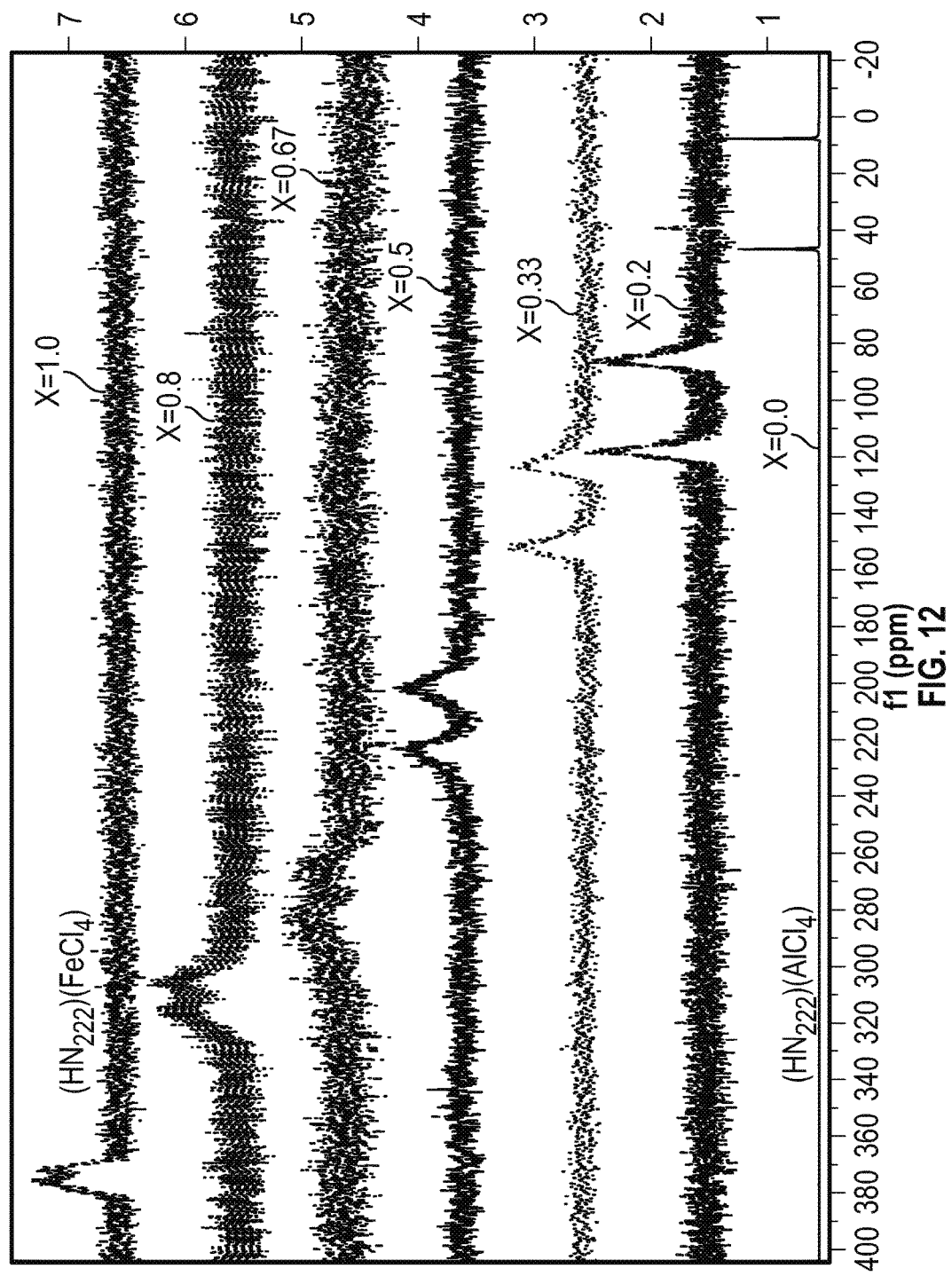
FIG. 12 is a $^{13}C$ NMR spectrum of $[HN_{222}][(1-x)AlCl_4+xFeCl_4]$ with different molar fraction (55° C., neat, DSMO-$d_6$ lock).

$^{13}$C NMR: DSIL were characterized by $^{13}$C NMR at 55° C. for neat samples and, similarly to both $^{27}$Al and $^{1}$H NMR, a graduate downfield chemical shift was observed with increase of amount of FeCl$_4$; the dependence of chemical shift of CH$_2$ and CH$_3$ carbon peaks on FeCl$_4$ amount added was also linear (FIG. 12). As the molar fraction of Al in the DSIL decreases, then there is a significant downfield shift in the $^{13}$C NMR peak.

Figure 13A:
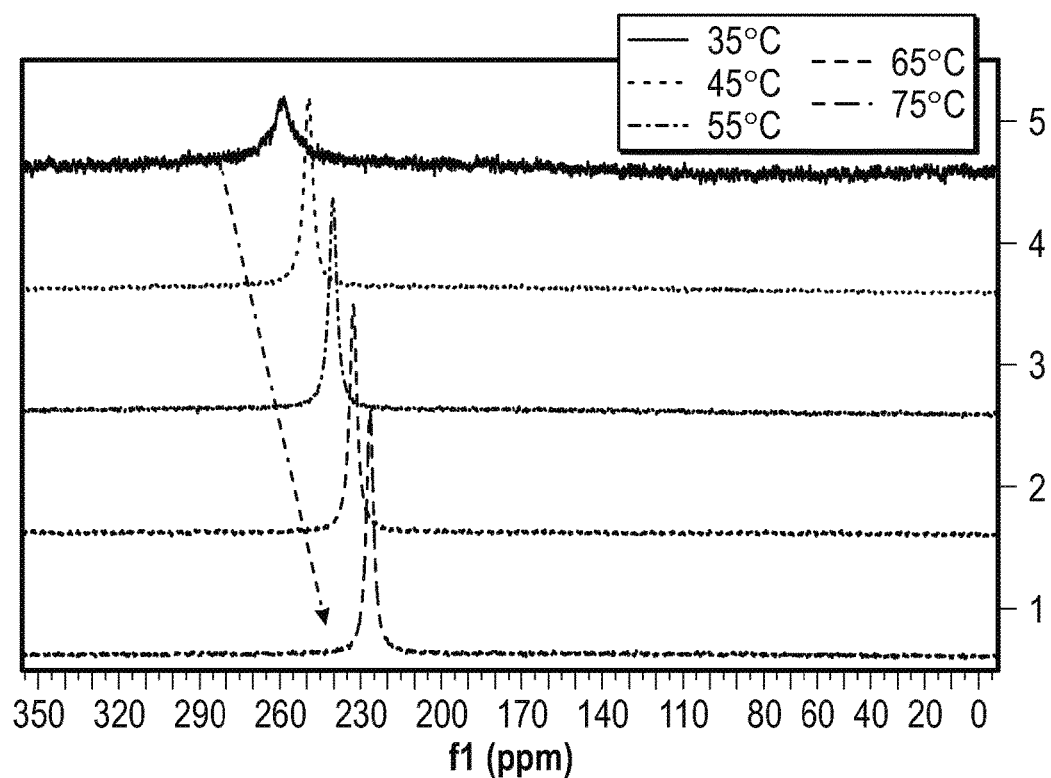
FIG. 13A is an $^{27}Al$ NMR spectrum of $[HN_{222}][0.5AlCl_4+0.5FeCl_4]$ at different NMR instrument temperature (30-75° C., neat, DSMO-$d_6$ lock).
Figure 13B:
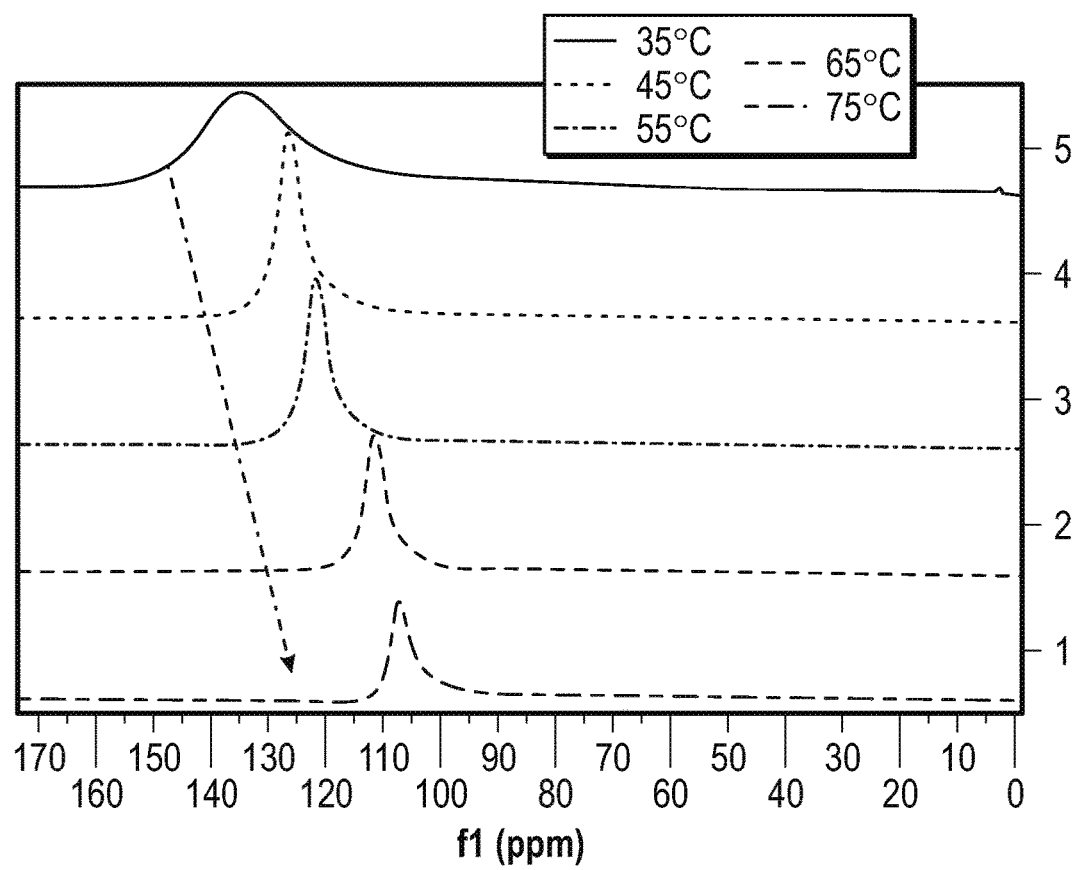
FIG. 13B is a $^1H$ NMR spectrum of $[HN_{222}][0.5AlCl_4+0.5FeCl_4]$ at different NMR instrument temperature (30-75° C., neat, DSMO-$d_6$ lock).

Temperature Effect (on the example of $[HN_{222}][(1-x)AlCl_4+xFeCl_4]$ system, x=0.5: To investigate the effect of temperature on the chemical shift of protons present in DSIL, we studied the $^{27}$Al NMR and $^{1}$NMR of $[HN_{222}][0.5AlCl_4+0.5FeCl_4]$ at various NMR probe temperatures (FIGS. 13A and 13B). In this $[HN_{222}][0.5AlCl_4+0.5FeCl_4]$, with decrease in the temperature of NMR instrument, there was a significant increase of the chemical shift of aluminum signal (in $^{27}$Al NMR) and proton signals (in $^{1}$H NMR), FIGS. 13A and 13B.

Synthesis and Characterization of DSIL: Triethylammonium [Chloroaluminate-Chloroferrate] $\{[HN_{222}][(1-x)AlCl_4+xFeCl_4]\}$ in Solvent (Benzene), on the Example of $[HN_{222}][0.5AlCl_4+0.5FeCl_4]$ To see if there is any difference in the $[HN_{222}][0.5AlCl_4+0.5FeCl_4]$ when DSIL is prepared in benzene as a solvent, this system using benzene was prepared and compared with DSIL prepared under solventless.

For the synthesis of $[HN_{222}][0.5AlCl_4+0.5FeCl_4]$, 2 mmol of white solid $[HN_{222}][AlCl_4]$ was placed into a 20 mL screw top vial and 2 mmol of green solid $[HN_{222}][FeCl_4]$ was added under flow of argon (using a glove bag). After that 2 g benzene were added to the vial. (When benzene was added, a biphasic system (liquid clathrate) was formed, immediately.) The screw top vial was equipped with Teflon coated magnetic stir bar. After addition of the reactants, the vial was capped using a cap with a Teflon/silicon (10/90) septum, and sealed with Parafilm. The vial was then removed from the glove bag and reaction mixture heated in a temperature controlled oil bath with magnetic stirring at 75° C. for 4 h (Scheme 3, above in section 1).

After 4 h, the two phases were separated using a Pasteur glass pipet, and both layers were characterized by $^{1}$H NMR and $^{27}$Al NMR. Benzene layer was first characterized before benzene was evaporated and then after evaporation of benzene.

Figure 14:
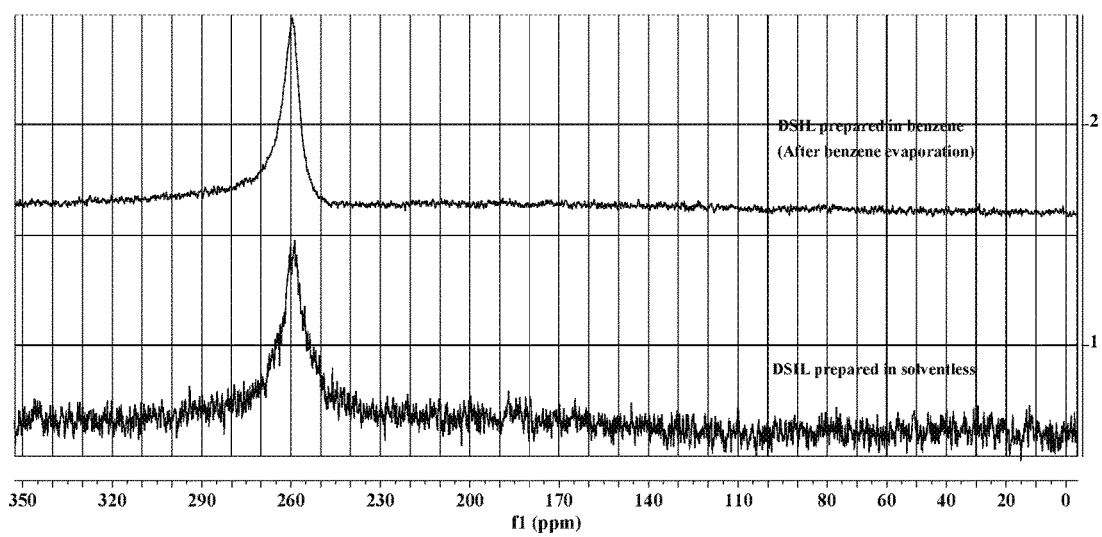
FIG. 14 is a pair of $^{27}Al$ NMR spectra of $[HN_{222}][0.5AlCl_4+0.5FeCl_4]$ system prepared in benzene, after evaporation of benzene (top spectra) and compared with solventless (bottom spectra) at 35° C., neat, DSMO-$d_6$ lock.

Lower Layer from the $[HN_{222}]_{1.5}[0.5Al_2Cl_7+0.5FeCl_4]$ Prepared in Benzene as a Solvent $^{27}$Al NMR: $^{27}$Al NMR indicated no change in the spectra of $[HN_{222}][0.5AlCl_4+0.5FeCl_4]$ prepared under solventless vs. $[HN_{222}][0.5AlCl_4+0.5FeCl_4]$ prepared in benzene after the solvent removal (FIG. 14).

Figure 15:
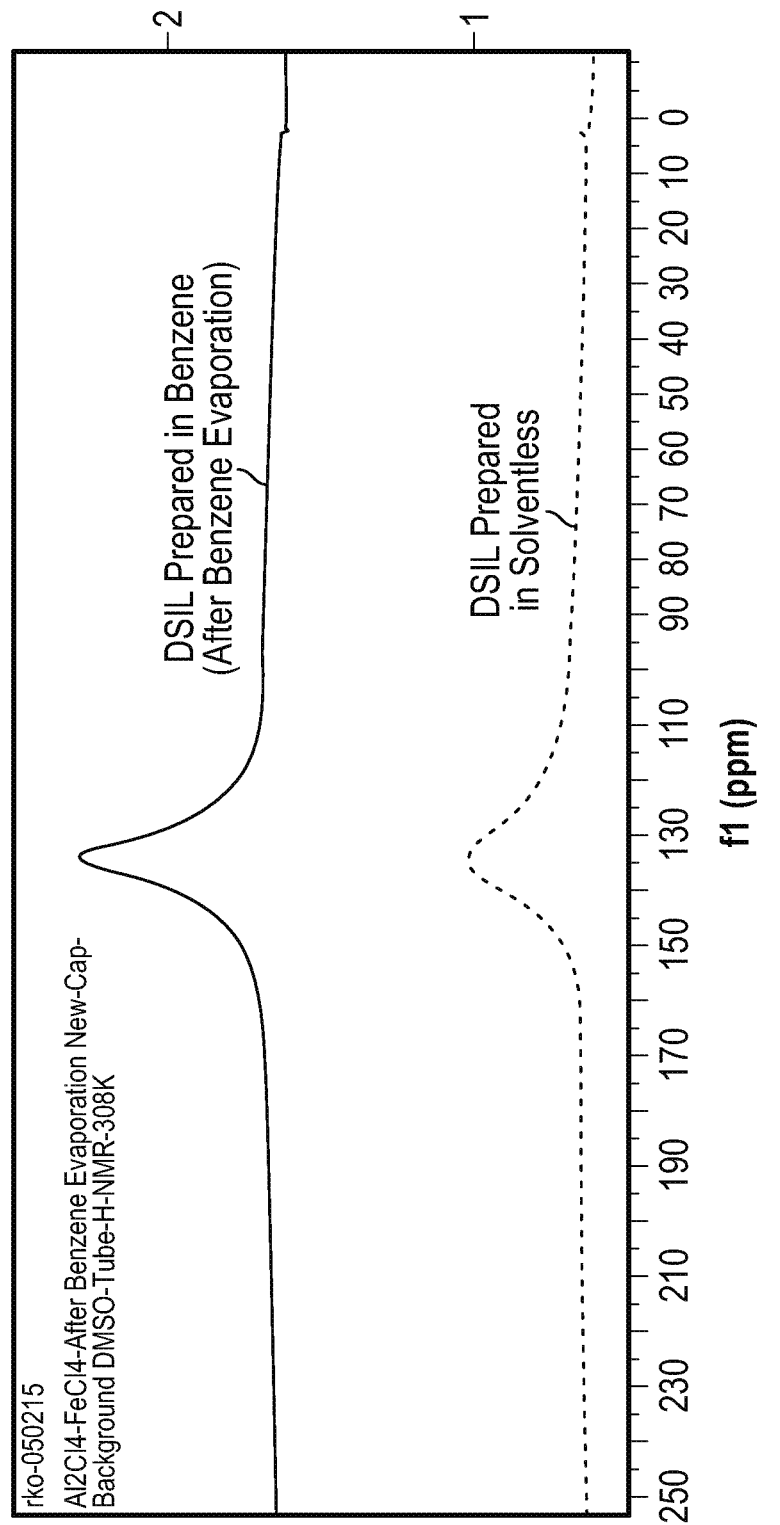
FIG. 15 is a pair of $^1H$ NMR spectra of $[HN_{222}][0.5AlCl_4+0.5FeCl_4]$ system prepared in benzene, after evaporation of benzene (top spectrum) and compared with solventless (bottom spectrum) at 35° C., neat, DSMO-$d_6$ lock.

$^{1}$H NMR: $^{1}$H NMR indicated no change in the spectra of $[HN_{222}][0.5AlCl_4+0.5FeCl_4]$ prepared under solventless vs. $[HN_{222}][0.5AlCl_4+0.5FeCl_4]$ prepared in benzene after the solvent removal (FIG. 15).

Synthesis and Characterization of DSIL: Triethylammonium [Chloroaluminate-Chlorozincate] $\{[HN_{222}]_{2x}[(1-x)AlCl_3+xZnCl_4]\}$ Under Solventless Conditions For the synthesis of $[HN_{222}]_{2x}[(1-x)AlCl_3+xZnCl_4]$ DSIL, white solid $[HN_{222}]_2[ZnCl_4]$ was placed into a 20 mL screw top borosilicate glass vial and white solid AlCl$_3$ was added under flow of argon (using a glove bag). The screw top vial was equipped with Teflon coated magnetic stir bar. After addition of the reactants, the vial was capped using a cap with a Teflon/silicon (10/90) septum, and sealed with Parafilm. The vial was then removed from the glove bag and the reaction mixture was heated in a temperature controlled oil bath with magnetic stirring at 75° C. for 4 h (Scheme 4).

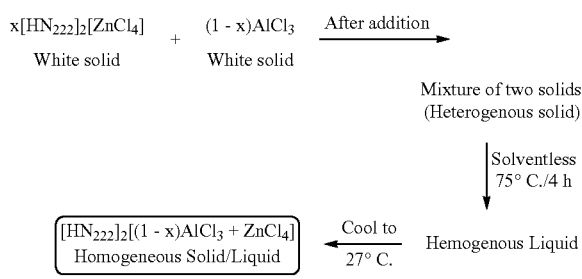

Scheme 4. Reaction scheme to prepare $[HN_{222}]_{2x}(1-x)AlCl_3 + xZnCl_4]$ DSIL by nonstoichiometric addition of metal salts.

By following the above procedure, $[HN_{222}]_{2x}[(1-x)AlCl_3+xZnCl_4]$ DSILs were prepared with different molar fraction (x) of the metal salts. Observations are summarized in Table 7. When the metal salts were combined in the range of x=0.33 to 0.5, homogeneous liquid at 75° C. but homogeneous solid forms when it cool to room temperature. Changes in the physical state (such as melting point) and color of the system indicated a possible formation of new species in the DSIL. These DSIL were characterized by several spectroscopic techniques which are explained below. Table 7 summarizes the observed changes on the DSIL.

TABLE 7

$[HN_{222}]_{2x}[(1-x)AlCl_3 + xZnCl_4]$ DSIL prepared under solventless at 75° C. for 4 h

| | Physical Observations | | |
|---|---|---|---|
| Composition (x) | After addition (room temperature) | After heating (75° C., 1 to 4 h) | After cooling (to room temperature) |
| 0.0 | | $AlCl_3$ (White solid) | |
| 0.1 | Mixture of white solid and green solid | Gray liquid with some solid | Dark black liquid with some solid ppt. |
| 0.25 | | Milky white liquid | Heterogeneous milky liquid and solid ppt. |
| 0.33 | | Colorless liquid | Colorless hard solid* |
| 0.4 | | Brown liquid | Brown soft solid* |
| 0.5 | | Colorless liquid | Colorless viscous liquid |
| 0.6, 0.75, 0.9 | | Faint gray sticky solid at the bottom and a white dry powder | |
| 1.0 | | $[HN_{222}]_2[ZnCl_4]$ (White solid) | |

Where x is molar fraction of $[HN_{222}]_2[ZnCl_4]$ in $[HN_{222}]_{2x}[(1-x)AlCl_3 + xZnCl_4]$ system;
*Crystal formation when cool to RT.

Table 8 summarizes the results obtained with the analytical techniques used for characterization of the $[HN_{222}]_{2x}[(1-x)AlCl_3+xZnCl_4]$ system. All characterization details are provided below.

TABLE 8

Summary of the results obtained during characterization of the $[HN_{222}]_{2x}[(1-x)AlCl_3 + xZnCl_4]$ system

| Characterization technique | Composition (x) | | |
|---|---|---|---|
| | 0.33 | 0.4 | 0.5 |
| $^{27}$Al NMR | Two peaks were observed (at 96 and 104 ppm), indicating two types of Al species. | | One peak was observed (at 104 ppm) indicating one type of Al species. |
| $^1$H NMR | A significant change in the chemical shift of NH proton indicates a change in N atom's electronic environment but no change in the chemical shift of $CH_3$ and $CH_2$ protons of ethyl group on ammonium cation was observed. | | |

Figure 16A:
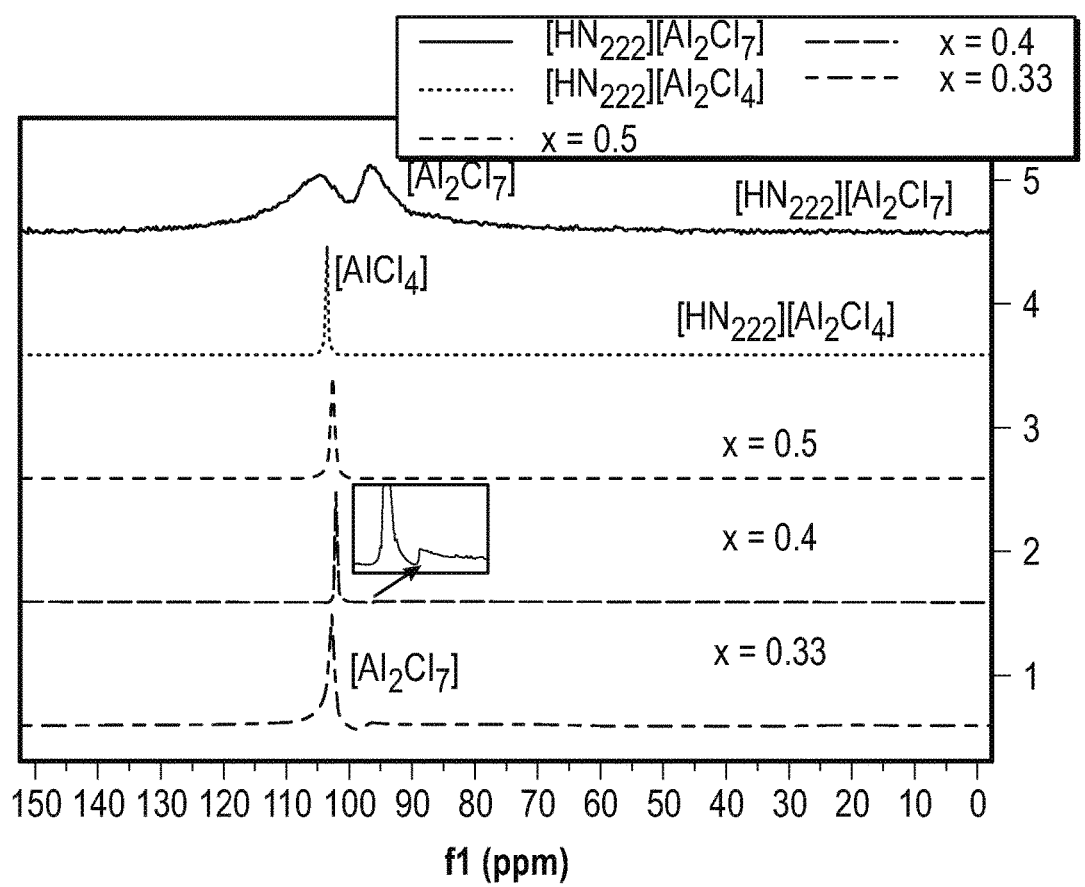
FIG. 16A is a group of $^{27}Al$ NMR spectra of $[HN_{222}]_{2x}[(1-x)AlCl_3+xZnCl_4]$ at x=0.33, 0.4, and 0.5 (55° C., neat, DSMO-$d_6$ lock).
Figure 16B:
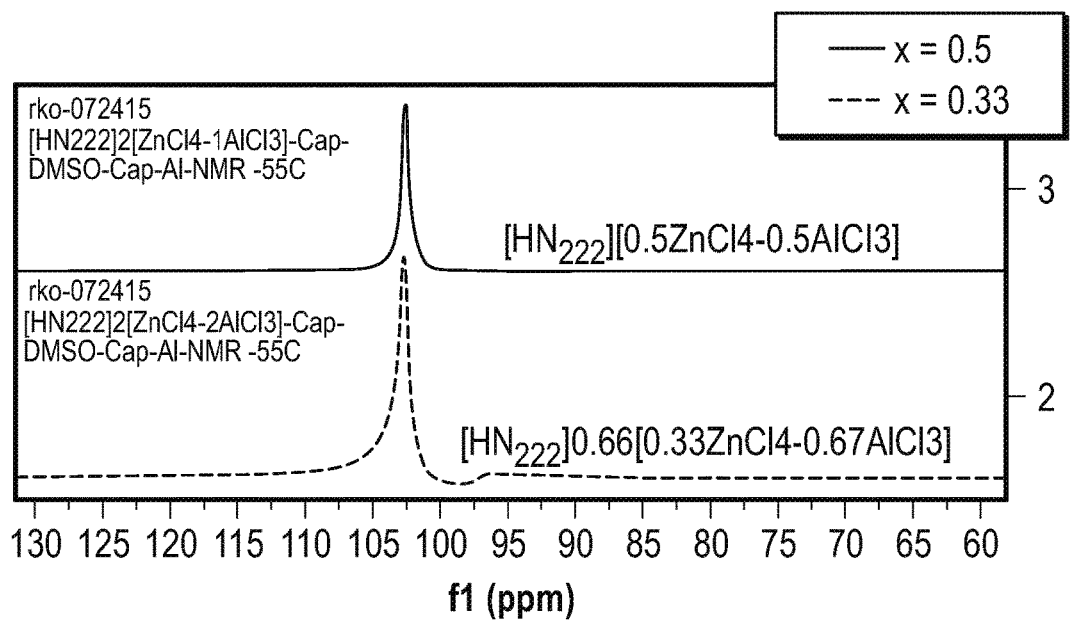
FIG. 16B is a pair of $^{27}Al$ NMR spectra of $[HN_{222}]_{2x}[(1-x)AlCl_3+xZnCl_4]$ at x=0.33 and 0.5 (55° C., neat, DSMO-$d_6$ lock).

$^{27}$Al NMR: To identify the species present in $[HN_{222}]_{2x}[(1-x)AlCl_3+xZnCl_4]$ DSIL, the homogenous samples were characterized by $^{27}$Al NMR under solventless (using dimethyl sulfoxide-$d_6$ as an external lock solvent, represented here as DMSO-$d_6$) at 55° C. Upon addition of $[HN_{222}]_2[ZnCl_4]$ into $AlCl_3$ at 0.33 molar ratio, two Al species were detected which are consistent with $[AlCl_4]^-$ and $[Al_2Cl_7]^-$ species indicate the formation of new compounds, but the signal for $[Al_2Cl_7]^-$ in the x=0.4 system was much smaller as compared to that in x=0.33 system indicating relatively lower concentration of this species. But at 0.5 molar ratio, only one Al species was detected which is consistent with $[AlCl_4]^-$ (FIGS. 16A and 16B).

Figure 17A:
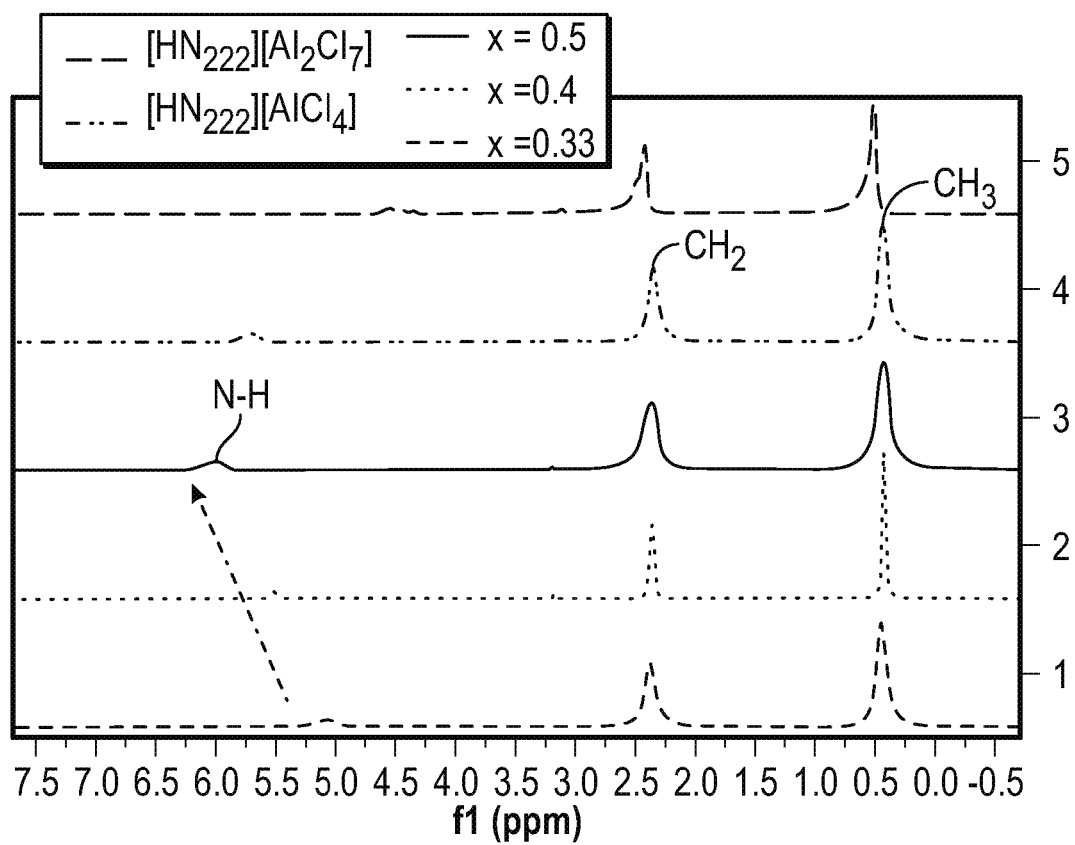
FIGS. 17A-B are $^1H$ NMRs of $[HN_{222}]_{2x}[(1-x)AlCl_3+xZnCl_4]$ at x=0.33, 0.4, and 0.5 (55° C., neat, DSMO-$d_6$ lock).
Figure 17B:
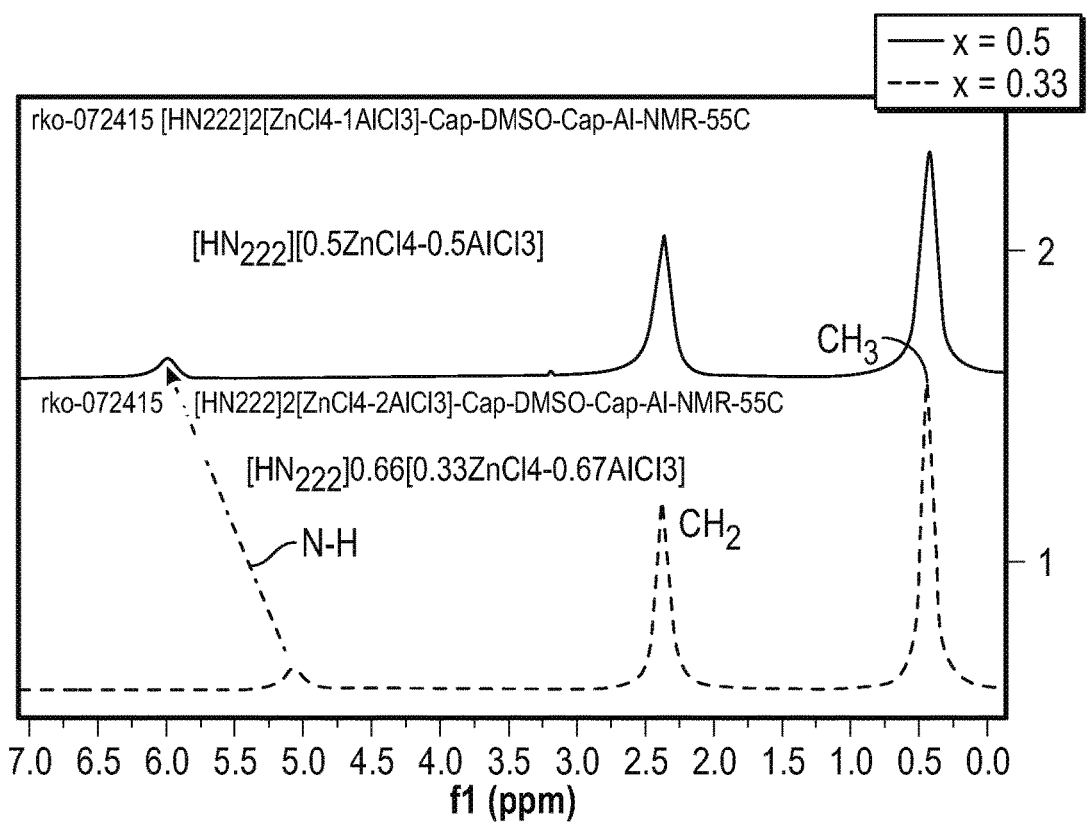

$^1$H NMR: DSIL were also characterized by solventless $^1$H NMR (using DMSO-$d_6$ as an external lock solvent) at 55° C. There was significant change in the location of N—H proton in $[HN_{222}]_{2x}[(1-x)AlCl_3+xZnCl_4]$ DSIL, with increasing the molar ratio of Al but no change observed in the chemical shift of $CH_3$ and $CH_2$ protons of the ethyl group from ammonium cation (FIGS. 17A and 17B). The N—H proton shifts upfield as $AlCl_3$ increases, consistent with a decrease in $Cl^-$ basicity as the amount of highly acidic $Al^-$ ions increases. To confirm this, control experiments were carried out with $[HN_{222}][AlCl_4]$, and $[HN_{222}][Al_2Cl_7]$. It was observed that the N—H proton shifting downfield in less Lewis acidic $[HN_{222}][AlCl_4]$ than $[HN_{222}][Al_2Cl_7]$.

Figure 18A:
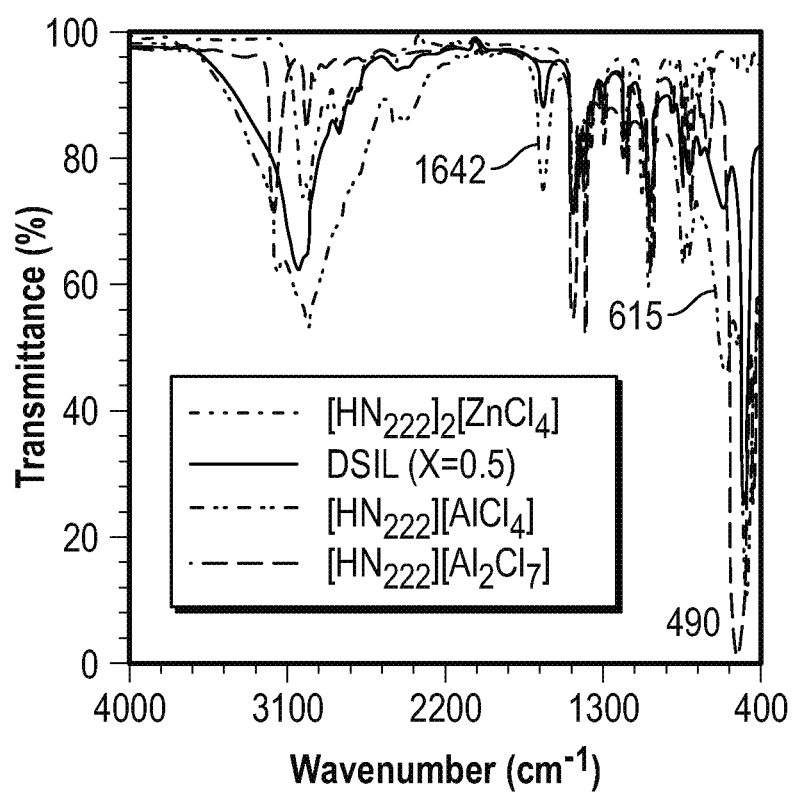
FIGS. 18A-C are IR spectra of $[HN_{222}][0.5AlCl_3+0.5ZnCl_4]$ and compared with some controlled samples.
Figure 18B:
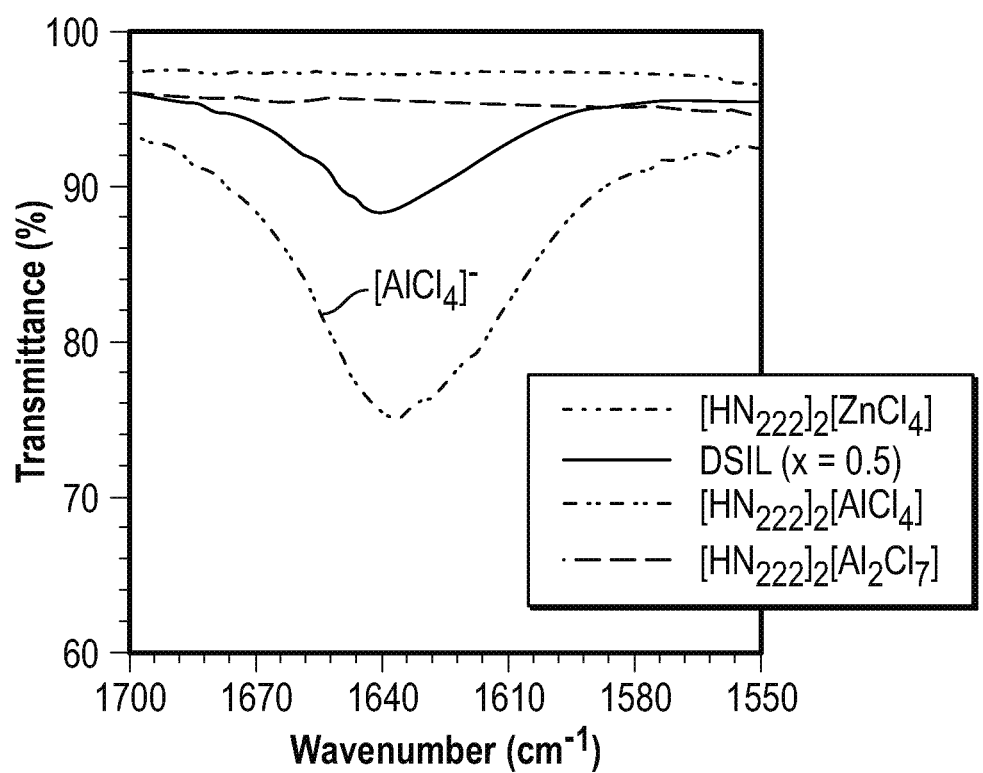
Figure 18C:
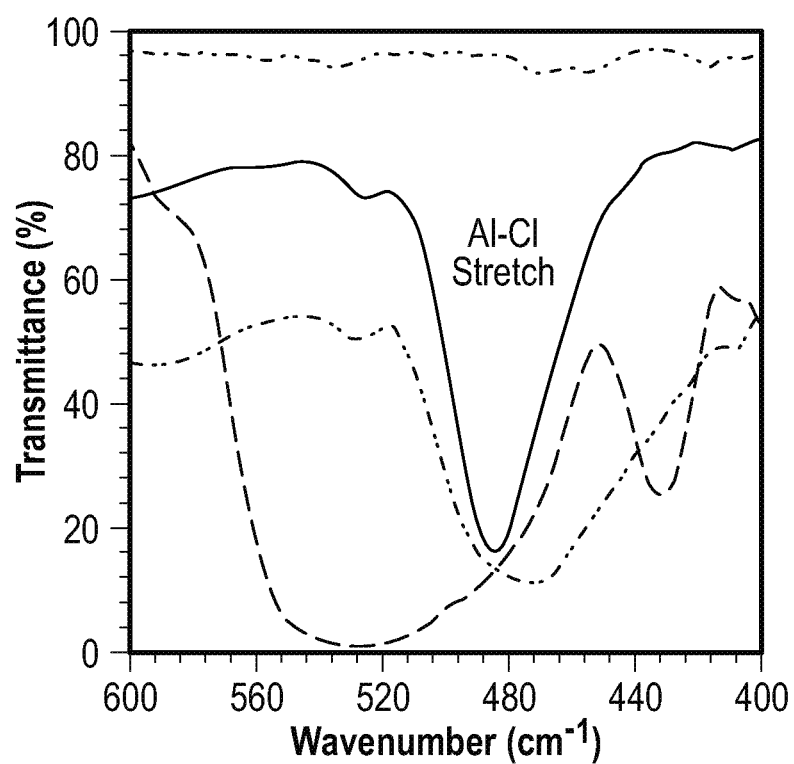

IR:

IR spectra were also recorded on the neat DSILs and generally agree with the NMR results. These DSIL formed at x=0.5 shows IR bands at 490, 613, and 1642 cm$^{-1}$ that are consistent with $[HN_{222}][AlCl_4]$ except for the broadening of the band towards lower wavenumbers (FIGS. 18A, 18B, and 18C). The IR bands at 613 and 1642 are not shifted greatly from their positions in $[HN_{222}][AlCl_4]$ and are associated with C—H bending modes and the interaction of the $[HN_{222}]^+$ ion with the metal complex. The peak at 490 is assigned to the Al—Cl stretching mode and, in contrast to the other two peaks, shows a marked broadening towards lower wavenumbers when compared $[HN_{222}][AlCl_{14}]$. Interestingly, in $[HN_{222}][Al_2Cl_7]$, the IR band in the DSIL is broadened in the opposite direction. While the increased acidity of $[Al_2Cl_7]^-$ would be expected to cause stronger Al—Cl interactions and thus correlates with the blue shift relative to $[AlCl_4]^-$, the DSIL shows a red shift likely caused by weakening of Al—Cl bonds by interactions with $Zn^{2+}$. This could have important consequences for catalysis although the DSIL has lower acidity than $[Al_2Cl_7]^-$, its weaker Al—Cl bonds may indicate the $Cl^-$ are more labile and thus the catalytic $Al^{3+}$ centers are more accessible to substrates.

Figure 19A:
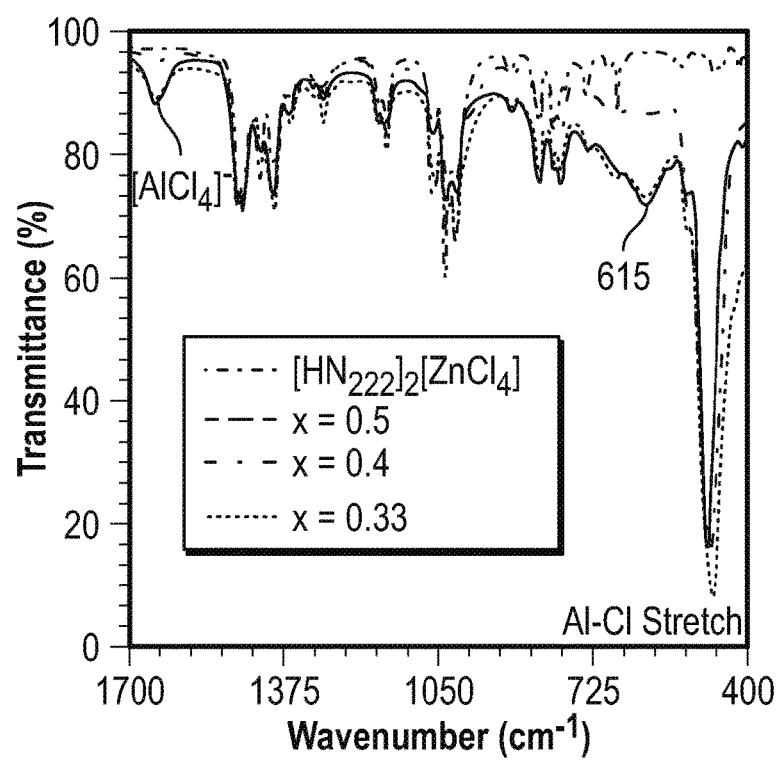
FIGS. 19A-B are IR spectra of $[HN_{222}]_{2x}[(1-x)AlCl_3+xZnCl_4]$ at x=0.33, 0.4, and 0.5 and compared with $[HN_{222}]_2[ZnCl_4]$.
Figure 19B:
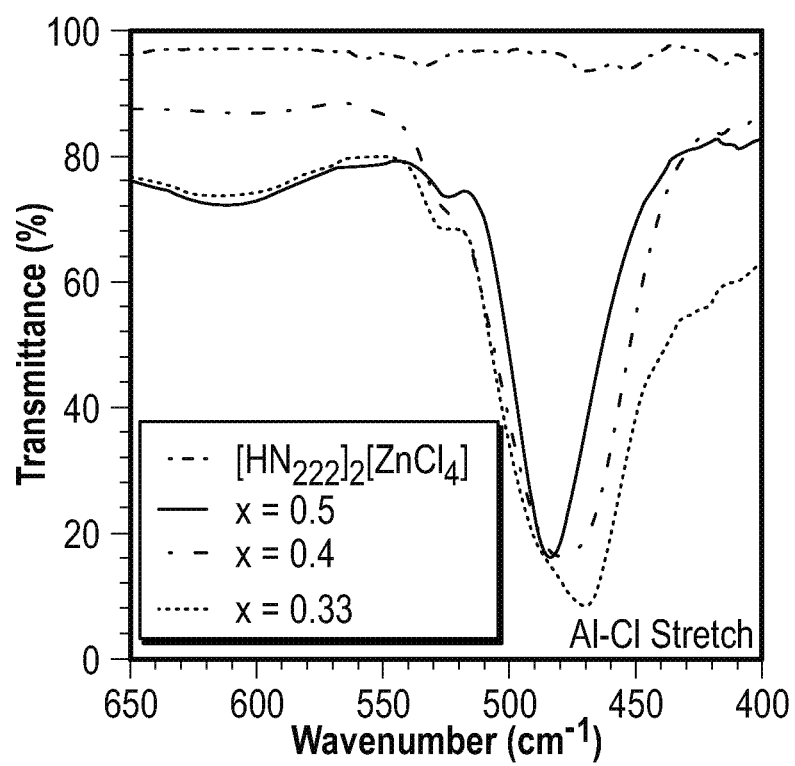

The stretch at ~490 cm$^{-1}$ is sensitive to the amount of $AlCl_3$ in the system. The broadening towards lower wavenumbers is most pronounced at lower amounts of $AlCl_3$, i.e. the greatest ratios of $[ZnCl_4]^-$ to $AlCl_3$ (FIGS. 19A and 19B). The peak is also becomes less symmetric at these compositions, with x=0.33 appearing to be a convolution of two peaks. This shows that there is complete $Cl^-$ transfer from $[ZnCl_4]^{2-}$ to $AlCl_3$ at all compositions and possibly $Al^{3+}$ species with more than four $Cl^-$ ions in the coordination sphere at high ratios of $ZnCl_4^{2-}$ to $Al^{3+}$. This could occur, for instance, if a $[ZnCl_4]^{2-}$ ion were to act as a bidentate ligand for an $Al^{3+}$ center.

SCXRD: The soft brown solid $[HN_{222}]_{0.8}$ $[0.6AlCl_3+0.4ZnCl_4]$ neat sample was crystallized by heating at 100° C. followed by very slow cooling and later sample was put for logger days (more than 30 days). DSIL crystals was collected on the glass plate contains Paratone-N oil and single crystal was collected under microscope. The collected single crystal was monitored by SCXRD and found the unit cell of the DSIL system well matches with the $[HN_{222}][AlCl_4]$.

Figure 20:
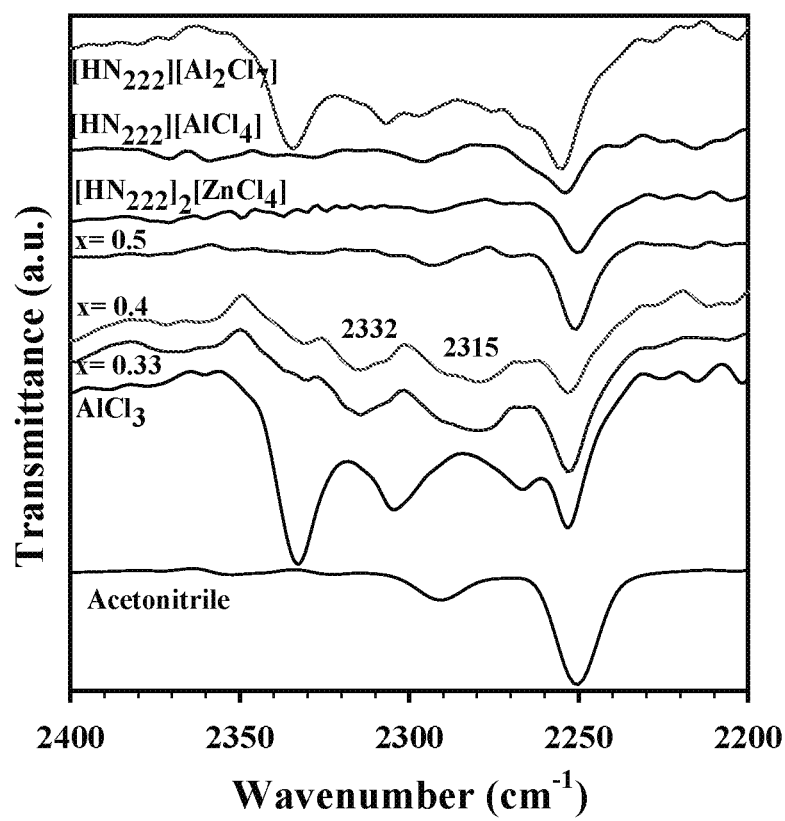
FIG. 20 are acetonitrile-IR spectra of $[HN_{222}]_{2x}[(1-x)AlCl_3+xZnCl_4]$ at x=0.33, 0.4, and 0.5 and compared with $[HN_{222}]_2[ZnCl_4]$, $[HN_{222}][AlCl_4]$ and $[HN_{222}][Al_2Cl_7]$.

Acetonitrile (ACN)-IR: Acetonitrile is a weak base and can be used as a probe molecule in IR spectroscopy to characterize Lewis acidity (Kore et al., *Journal of Molecular Catalysis A: Chemical*, 2013, 376, 90-97). It is well known that the CN group can react with Lewis acid to produce CN-Lewis acid adduct, which shows a new absorption peak at 2200-2400 cm$^{-1}$ in the FT-IR spectra. Upon increasing the strength of Lewis acid, the absorption peak shifts to higher wave number. ACN shows two IR bands at 2252 and 2292 cm$^{-1}$ for the CN stretching vibrations, when the ACN complex with $[HN_{222}]_{2x}[(1-x) AlCl_3+xZnCl_4]$ at 0.33 and 0.4 mole fractions, both show the appearance of a new band at higher wavenumbers 2315 and 2332 cm$^{-1}$ (FIG. 20). [HN$_{222}$][Al$_2$Cl$_7$] has more acidic than DSIL. These results are indicating that DSIL contains both strong as well as weak Lewis acidity. However, it may be noted that the peak in the Lewis acidic region was not detected for the DSIL at 0.5 mole fraction as well as [HN$_{222}$][AlCl$_4$].

Synthesis and Characterization of DSIL System: Triethylammonium [Chloroaluminate-Chlorozincate] {[HN$_{222}$]$_{2x}$[(1−x)AlCl$_3$+xZnCl$_4$]} in Solvent (Benzene) on the Example of [HN$_{222}$][0.5AlCl$_3$+0.5ZnCl$_4$]

To see if there is any difference in the [HN$_{222}$][0.5AlCl$_{3+0.5}$ZnCl$_4$] when DSIL is prepared neat or in benzene as a solvent, we have prepared this system using benzene and compared with the corresponding DSIL prepared under solventless.

For the synthesis of [HN$_{222}$][0.5AlCl$_3$+0.5ZnCl$_4$], 5 mmol of white solid [HN$_{222}$]$_2$[ZnCl$_4$] was placed into a 30 mL screw top vial and 5 mmol of white solid AlCl$_3$ was added under flow of argon (using a glove bag). After that, 11 g benzene were added to the vial (When benzene was added, a biphasic system (liquid clathrate) was formed immediately). The screw top vial was equipped with Teflon coated magnetic stir bar. After addition of the reactants, the vial was capped using a cap with a Teflon/silicon (10/90) septum, and sealed with Parafilm. The vial was then removed from the glove bag and the reaction mixture was heated in a temperature controlled oil bath with magnetic stirring at 75° C. for 4 h (Scheme 4).

Figure 22:
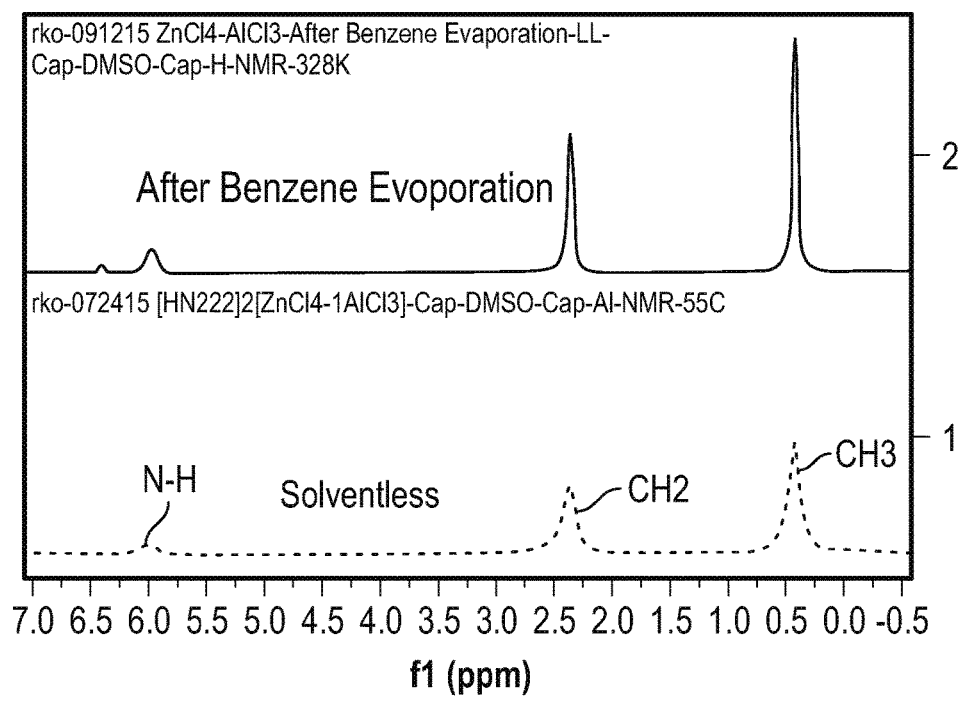
FIG. 22 is a group of $^1H$ NMR spectra of $[HN_{222}][0.5AlCl_3+0.5ZnCl_4]$ prepared in benzene before (top spectrum) and after (middle spectrum) solvent evaporation, compared with solventless (bottom spectrum) (55° C., neat, DSMO-$d_6$ lock).

After 4 h, the two phases were separated using a Pasteur glass pipet, and both layers were characterized by $^1$H NMR and $^{27}$Al NMR and compared with the corresponding DSIL prepared under solventless. Benzene layer was characterized before and after benzene removal. Table 9 summarizes the results obtained with the analytical techniques used for characterization of the [HN$_{222}$][0.5AlCl$_3$+0.5ZnCl$_4$]. All characterization details are provided below.

effect (FIG. 22). This indicates no differences between the DSIL prepared with or without solvent.

Figure 23:
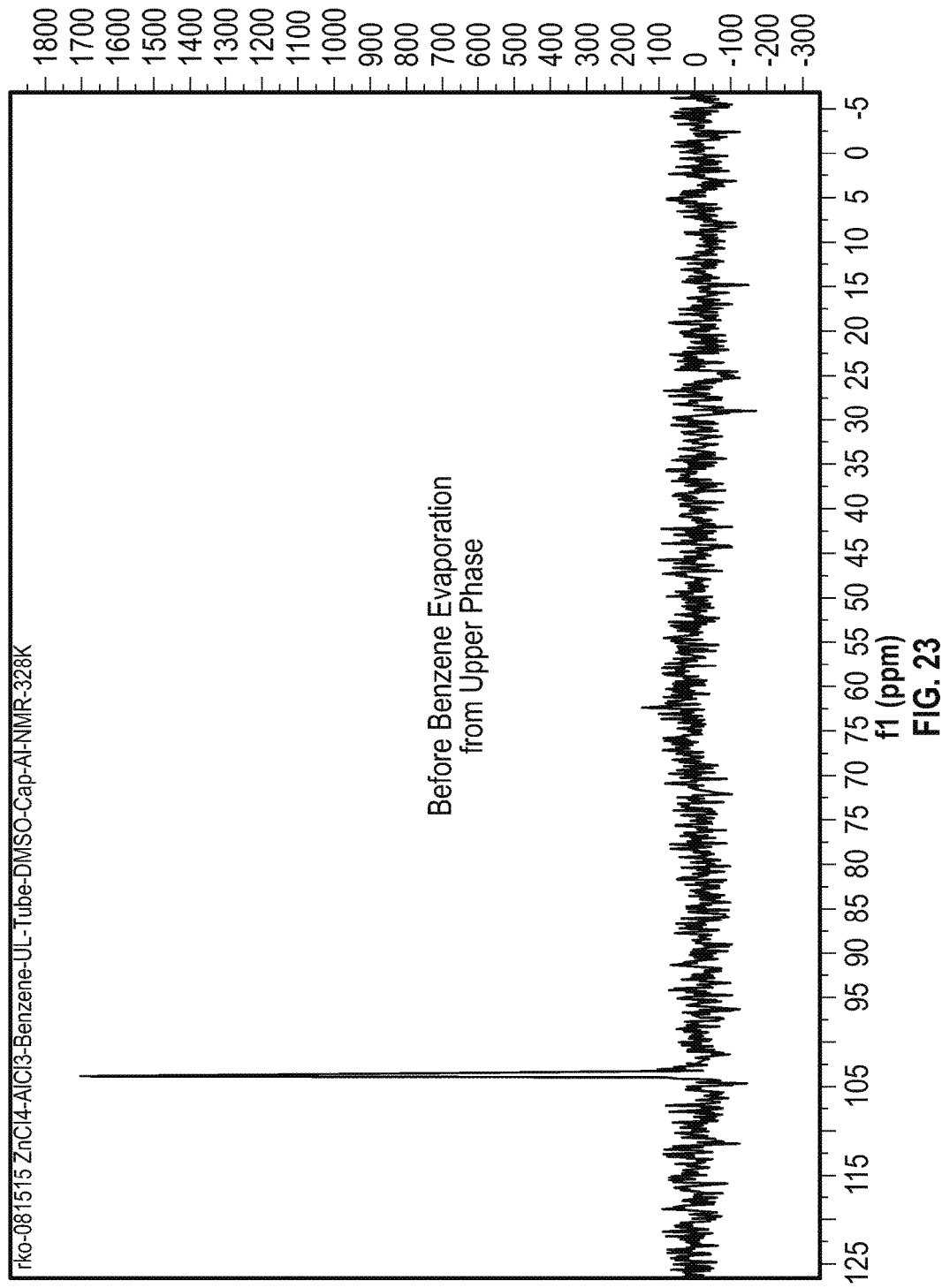
FIG. 23 is an $^{27}Al$ NMR spectrum of an upper benzene layer when $[HN_{222}][0.5AlCl_3+0.5ZnCl_4]$ system is prepared in benzene (55° C., neat, DSMO-$d_6$ lock).
Figure 24:
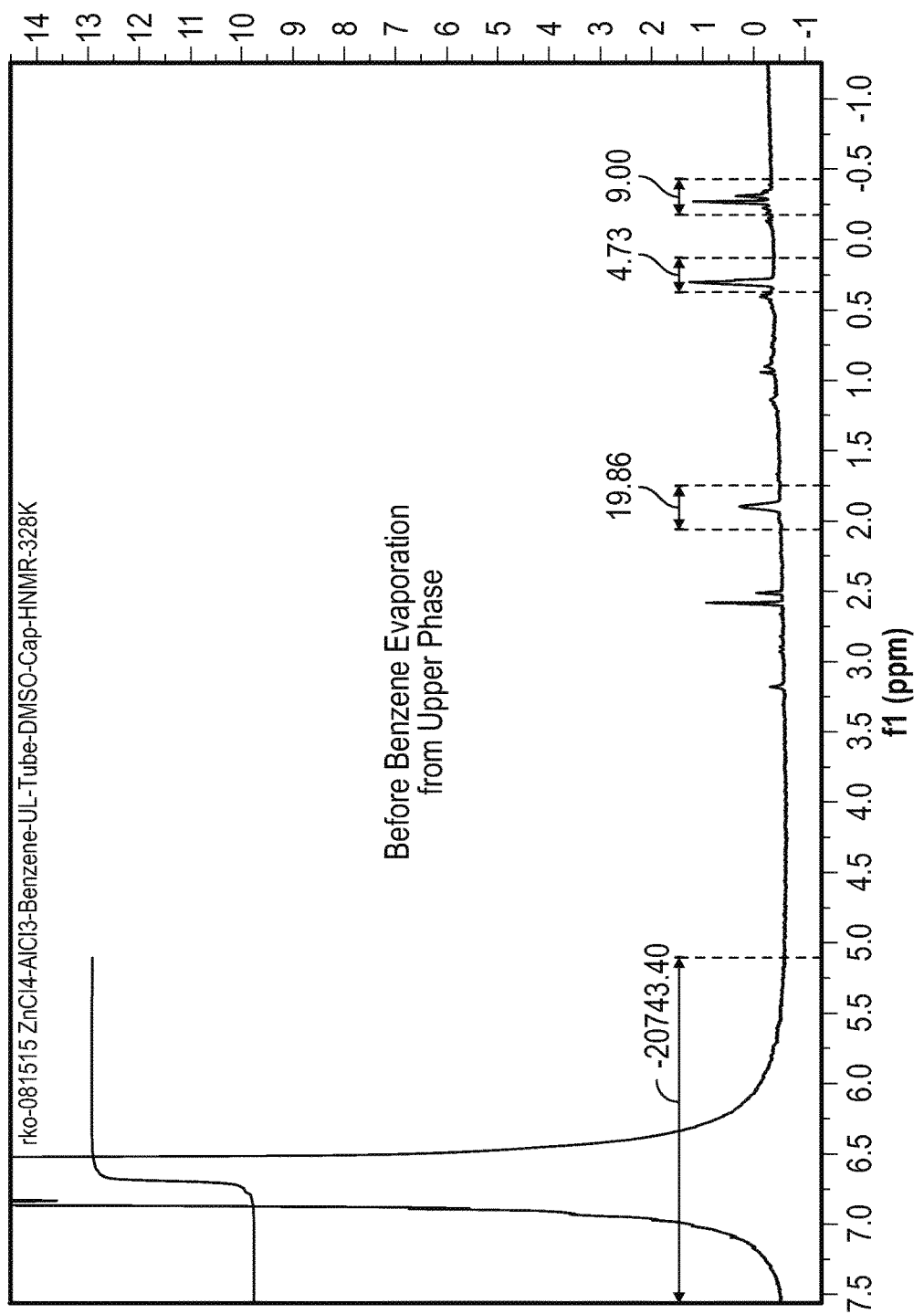
FIG. 24 is a $^1H$ NMR spectrum of an upper benzene layer when $[HN_{222}][0.5AlCl_3+0.5ZnCl_4]$ system is prepared in benzene (55° C., neat, DSMO-$d_6$ lock).

Upper (Benzene-Rich) Layer from the [HN$_{222}$][0.5AlCl$_3$+0.5ZnCl$_4$] Prepared in Benzene as a Solvent The upper layer was analyzed using $^{27}$Al NMR and $^1$H NMR. As can be seen in FIGS. 23 and 24, traces of the product were detected, almost undetectable by NMR (required significant increase if spectrum intensity) due to low product concentration in the upper layer.

Synthesis and Characterization of DSIL: Triethylammonium [Chloroaluminate-Chlorozincate] {[HN$_{222}$][(1−x)Al$_2$Cl$_7$+xZnCl$_3$]} Under Solventless Conditions Experimental: For the synthesis of [HN$_{222}$][(1−x)Al$_2$Cl$_7$+xZnCl$_3$] DSIL, a very faint brown liquid [HN$_{222}$][Al$_2$Cl$_7$] was placed into a 20 mL screw top borosilicate glass vial and colorless highly viscous liquid [HN$_{222}$][ZnCl$_3$] was added under flow of argon (using a glove bag). The screw top vial was equipped with Teflon coated magnetic stir bar. After addition of the reactants, the vial was capped using a cap with a Teflon/silicon (10/90) septum, and sealed with Parafilm. The vial was then removed from the glove bag and the reaction mixture was heated in a temperature controlled oil bath with magnetic stirring at 75° C. for 4 h (Scheme 5).

Scheme 5. Reaction scheme to prepare
[HN$_{222}$][(1 − x)Al$_2$Cl$_7$ + xZnCl$_3$]
DSIL by nonstoichiometric addition of metal salts.

x[HN$_{222}$][ZnCl$_3$]  +  (1 − x)[HN$_{222}$][Al$_2$Cl$_7$]  $\xrightarrow{75° C./4 \text{ h}}$ Colorless viscous liquid    Faint brown liquid

TABLE 9

Summary of the results obtained during characterization of the [HN$_{222}$][0.5AlCl$_3$ + 0.5ZnCl$_4$]

| | | Using Benzene as a solvent (Liquid Clathrate) | | | |
| --- | --- | --- | --- | --- | --- |
| | | Lower layer | | Upper layer | |
| Characterization technique | Solventless | Before benzene evaporation | After benzene evaporation | Before benzene evaporation | After benzene evaporation |
| Color | Colorless viscous liquid | Colorless liquid | Colorless viscous liquid | Colorless liquid | Colorless solid |
| $^{27}$Al NMR | | 1 peak observed, at 104 ppm | | | |
| $^1$H NMR | [HN$_{222}$]$^+$ | Non-comparable (solvent effect) | Same system as solventless ([HN$_{222}$]$^+$) | Impurities (traces) of the product were present | |

Figure 21:
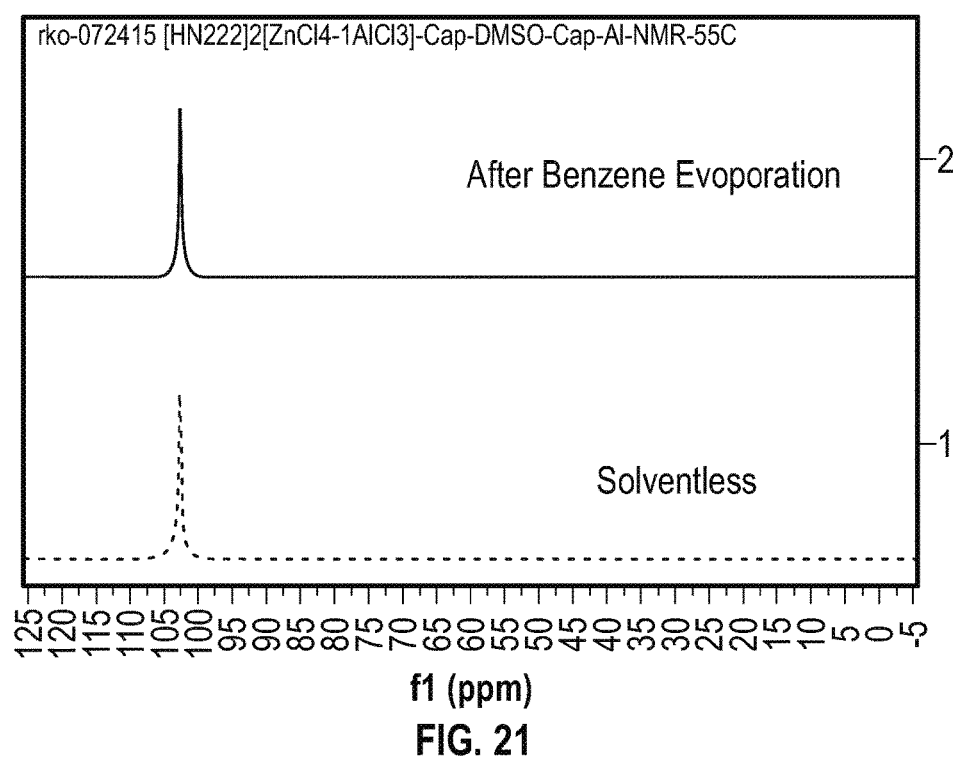
FIG. 21 is a pair of $^{27}Al$ NMR spectra of $[HN_{222}][0.5AlCl_3+0.5ZnCl_4]$ system prepared in benzene after benzene evaporation (top spectrum), compared with solventless (bottom spectrum) (55° C., neat, DSMO-$d_6$ lock).

Lower Layer from the [HN$_{222}$][0.5AlCl$_3$+0.5ZnCl$_4$] Prepared in Benzene as a Solvent $^{27}$Al NMR: After benzene evaporation, the colorless viscous liquid obtained appeared no different than the same system prepared solventless. The [HN$_{222}$][0.5AlCl$_3$+0.5ZnCl$_4$] was thus found in the lower layer after its synthesis in benzene. $^{27}$Al NMR indicated no change in the spectra of the DSIL when it was prepared under solventless or when it was prepared in benzene either before or after solvent removal (FIG. 21).

$^1$H NMR: $^1$H NMR indicated no change in the spectra of [HN$_{222}$][0.5AlCl$_3$+0.5ZnCl$_4$] prepared under solventless or in benzene after its evaporation. The chemical shift observed before benzene evaporation is attributed to benzene solvent -continued

[HN$_{222}$][(1 − x)Al$_2$Cl$_7$ + xZnCl$_3$]

Homogeneous liquid

By following the above procedure, [HN$_{222}$][(1−x)Al$_2$Cl$_7$+xZnCl$_3$] DSILs were prepared with different molar fraction (x) of the metal salts. Observations are summarized in Table 10. When the metal salts were combined in the range of x=0.67, homogeneous brown liquid DSIL was obtained. Changes in the physical state (such as melting point) and color of the system indicated a possible formation of new species in the DSIL. These DSILs were characterized by several spectroscopic techniques which are explained below.

Table 10 summarizes the observed changes on the DSIL.

TABLE 10

[HN$_{222}$][(1 − x)(Al$_2$Cl$_7$) + x(ZnCl$_3$)] DSIL prepared under solventless at 75° C. for 4 h

| Composition (x) | Physical Observations After cooling (to room temperature) |
|---|---|
| 0.0 | Faint brown liquid |
| 0.33 | Mixture of brown liquid and white precipitate at the bottom |
| 0.5 | Could of liquid and solid |
| 0.67 | Homogeneous brown liquid |
| 1.0 | White solid |

Where x is molar fraction of [HN$_{222}$][ZnCl$_3$] in [HN$_{222}$][(1 − x)(Al$_2$Cl$_7$) + x(ZnCl$_3$)] system.

Figure 25:
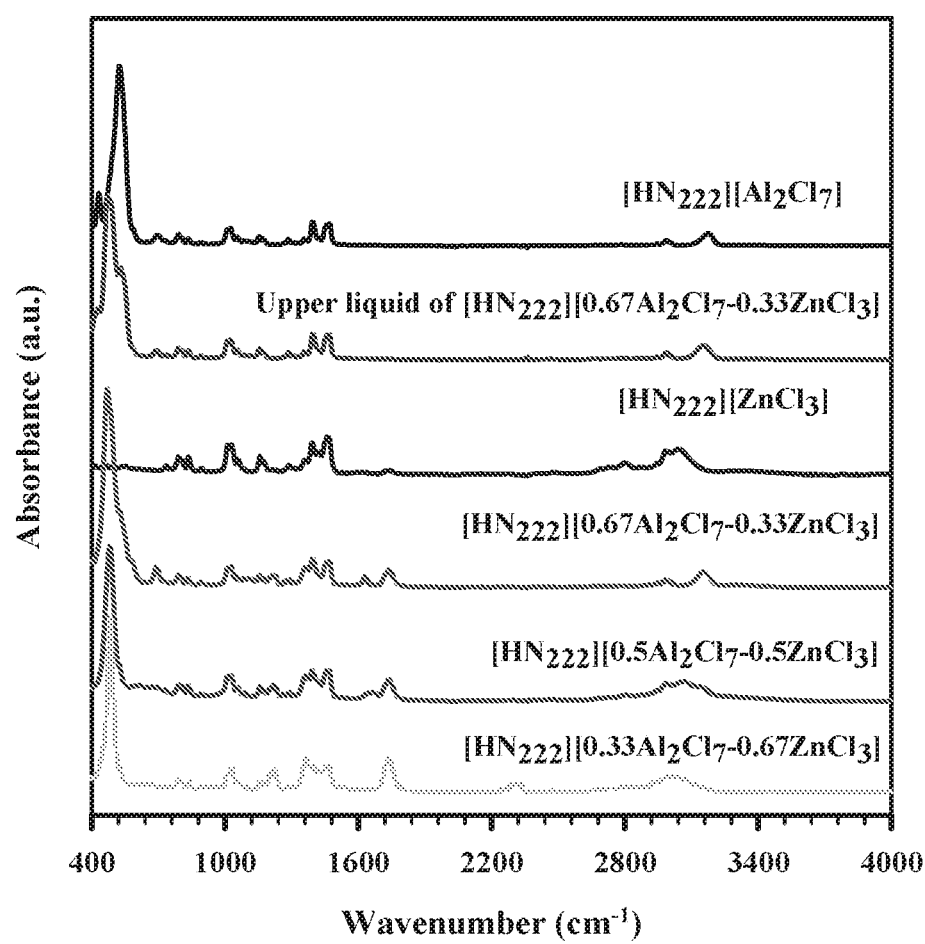
FIG. 25 are IR spectra of $[HN_{222}][(1-x)Al_2Cl_7+xZnCl_3]$ at x=0.33, 0.5, and 0.67 and compared with $[HN_{222}][ZnCl_3]$ and $[HN_{222}][Al_2Cl_7]$.

IR: DSIL were characterized by solventless IR. With increasing the amount of ZnCl$_3^-$ into [HN$_{222}$][(1−x)(Al$_2$Cl$_7$)+x(ZnCl$_3$)] DSILs, the IR band v (Al—Cl) shift to lower wavenumber. The lower IR band v (Al—Cl) of Al$_2$Cl$_7^-$ species shifting due to the interaction of ZnCl$_3^-$ with Al$_2$Cl$_7^-$ species. (FIG. 25).

Figure 26:
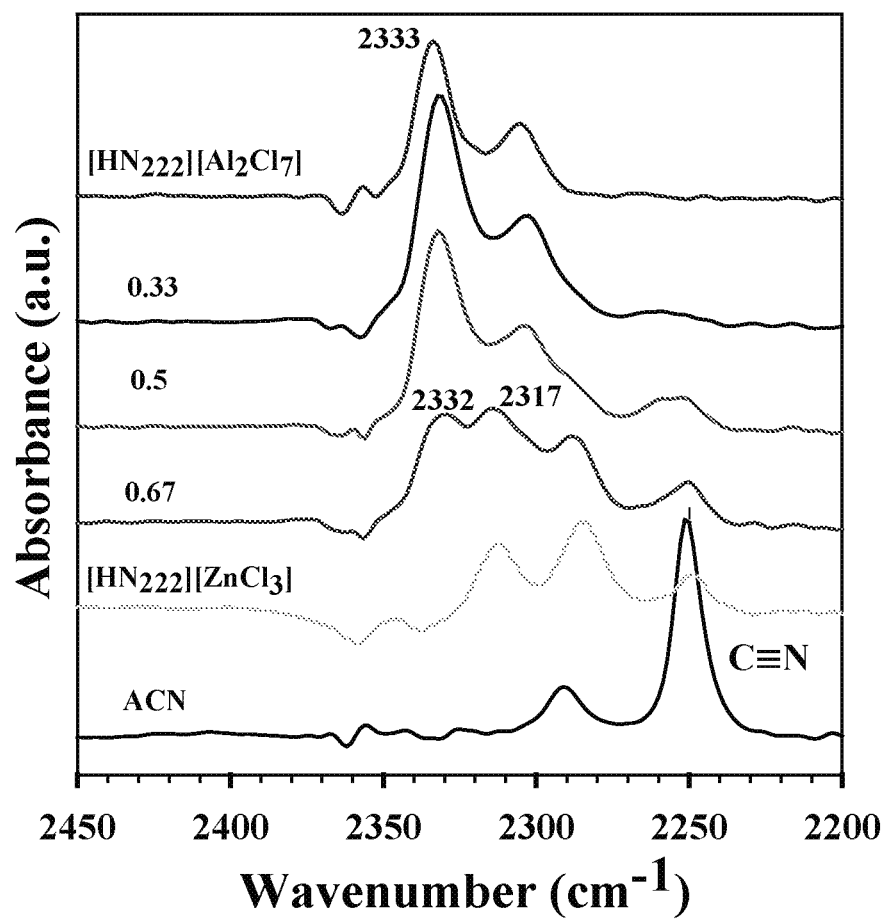
FIG. 26 are Acetonitrile-IR spectra of $[HN_{222}][(1-x)Al_2Cl_7+xZnCl_3]$ at x=0.33, 0.5, and 0.67 and compared with $[HN_{222}][ZnCl_3]$ and $[HN_{222}][Al_2Cl_7]$.

Acetonitrile (ACN) IR: Acetonitrile (ACN) is a weak base and used as a probe molecule in IR spectroscopy to characterize the Lewis acidity (Kore et al., *Journal of Molecular Catalysis A: Chemical*, 2013, 376, 90-97). It is well known that the CN group can react with Lewis acid to produce CN-Lewis acid adduct, which shows a new absorption peak at 2200-2400 cm$^{-1}$ in the FT-IR spectra. Upon increasing the strength of Lewis acid, the absorption peak shifts to higher wave number. ACN shows two IR bands at 2252 and 2292 cm$^{-1}$ for the CN stretching vibrations, when the ACN complex with [HN$_{222}$][ZnCl$_3$] and [HN$_{222}$][Al$_2$Cl$_7$], both show the appearance of a new band at higher wavenumbers 2315 and 2333 cm$^{-1}$ respectively (FIG. 26). [HN$_{222}$][Al$_2$Cl$_7$] has more acidic than [HN$_{222}$][ZnCl$_3$]. With increasing the amount of ZnCl$_3^-$ into DSIL, Lewis acidic IR band (2333 cm$^{-1}$) shift to lower wavenumber means decreasing their acidic strength. However, it may be noted that only at 0.67 molar ratio has two type of bands (2332 and 2317 cm$^{-1}$), indicating the two both strong as well as week acidic sites are available in the system.

Synthesis and Characterization of DSIL: Triethylammonium [Chloroaluminate-Hydrogen Sulfate] {[HN$_{222}$][(1-x)Al$_2$Cl$_7$+xHSO$_4$]} Under Solventless Conditions Experimental: For the synthesis of [HN$_{222}$][(1-x)Al$_2$Cl$_7$+xHSO$_4$] DSIL, a very faint brown liquid [HN$_{222}$][Al$_2$Cl$_7$] was placed into a 10 mL screw top borosilicate glass vial and pale yellow solid [HN$_{222}$][HSO$_4$] was added under flow of argon (using a glove bag). The screw top vial was equipped with Teflon coated magnetic stir bar. After addition of the reactants, the vial was capped using a cap with a Teflon/silicon (10/90) septum, and sealed with Parafilm. The vial was then removed from the glove bag and the reaction mixture was heated in a temperature controlled oil bath with magnetic stirring at 75° C. for 12 h (Scheme 6).

Scheme 6. Reaction scheme to prepare
[HN$_{222}$][(1 - x)Al$_2$Cl$_7$ + xHSO$_4$]
DSIL by nonstoichiometric addition of metal salts.

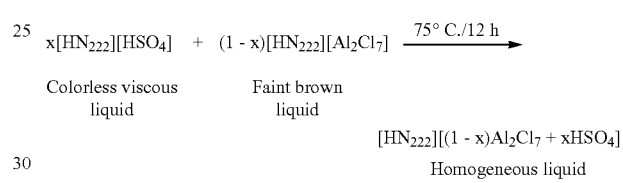

x[HN$_{222}$][HSO$_4$] + (1 - x)[HN$_{222}$][Al$_2$Cl$_7$] $\xrightarrow{75° C./12 h}$ Colorless viscous liquid    Faint brown liquid

[HN$_{222}$][(1 - x)Al$_2$Cl$_7$ + xHSO$_4$]
Homogeneous liquid

By following the above procedure, [HN$_{222}$][(1-x)Al$_2$Cl$_7$+xHSO$_4$] DSILs were prepared with different molar fraction (x) of the metal salts. Observations are summarized in Table 11. When the metal salts were combined in the range of x=0.2-0.67, homogeneous liquid DSIL were obtained. Changes in the physical state (such as melting point) and color of the system indicated a possible formation of new species in the DSIL.

Table 11 summarizes the observed changes on the DSIL.

TABLE 11

[HN$_{222}$][(1−x)Al$_2$Cl$_7$ + xHSO$_4$] DSIL prepared under solventless at 75 °C. for 12 h

| Composition (x) | Physical Observations | | |
|---|---|---|---|
| | RT addition | 75° C. after 12 h | Cool to RT |
| 0.0 | | Faint brown liquid | |
| 0.2 | | Black liquid | Black viscous liquid |
| 0.33 | Mixture of faint brown liquid and white solid at the bottom | Black liquid | Black highly viscous liquid |
| 0.5 | | Greyish white viscous liquid | Greyish white gel |
| 0.67 | Heterogeneous system | Faint Brown gel | |
| 0.8 | (Wet solid) | Wet solid | Faint brown gel and solid |
| 1.0 | Pale yellow solid | Pale yellow gel | Pale yellow solid (Hair like crystals) |

Where x is molar fraction of [HN$_{222}$][HSO$_4$] in [HN$_{222}$][(1 − x)Al$_2$Cl$_7$ + xHSO$_4$] system.

Application of [HN$_{222}$]$_{2x}$[(1−x)AlCl$_3$+xZnCl$_4$] DSIL in Beckmann Rearrangement Reactions For the Beckmann rearrangement reaction, 0.1 mmol of catalyst was placed into a 5 mL screw top borosilicate glass vial and followed by addition of 2 mL of acetonitrile as a solvent. Further, 1 mmol of acetophenone oxime was added into the above mixture under atmospheric of argon (using a glove bag). The screw top vial was equipped with Teflon coated magnetic stir bar. After addition of the reactants, the vial was capped using rubber septum, and sealed with Parafilm. The vial was then removed from the glove bag and the reaction mixture was heated in a temperature controlled oil bath with magnetic stirring at 80° C. for 3 h (Scheme 7). After 3 h, a small aliquot mixture was withdrawal from the reaction mixture and monitored by using GC-MS and summarized in the Table 12.

Scheme 7. Beckmann rearrangement reaction using [HN$_{222}$]$_{2x}$[(1 − x)AlCl$_3$ + xZnCl$_4$].

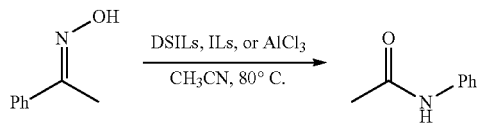

TABLE 12

Comparative catalytic activity data in the Beckmann rearrangement of acetophenone oxime

| E. N. | Catalyst | Conversion of Acetophenone oxime (%) | Selectivity of Acetanilide (%) |
|---|---|---|---|
| 1 | [HN$_{222}$]$_2$[ZnCl$_4$] | 43.5 | 13.1 |
| 2 | [HN$_{222}$][0.5AlCl$_3$ + 0.5ZnCl$_4$] | 87.5 | 81.3 |
| 3 | [HN$_{222}$]$_{0.6}$[0.6AlCl$_3$ + 0.4ZnCl$_4$] | 91.2 | 86.2 |
| 4 | [HN$_{222}$]$_{0.66}$[0.67AlCl$_3$ + 0.33ZnCl$_4$] | 99.3 | 97.4 |
| 5 | AlCl$_3$ | 84.5 | 69.8 |
| 6 | [HN$_{222}$][AlCl$_4$] | 85.0 | 70.1 |
| 7 | [HN$_{222}$][Al$_2$Cl$_7$] | 88.5 | 89.8 |

Reaction condition: Catalyst (0.1 mmol), acetophenone oxime (1 mmol), acetonitrile (2 mL), reaction temperature (80° C.) and time (3 h). Side product is acetophenone. Note: In the reactions a white solid precipitated formed at the bottom, except for the trial with [HN$_{222}$]$_2$[ZnCl$_4$].

The Lewis acidity compared by FT-IR noted above (FIG. 20), suggested that AlCl$_3$ was the most acidic. It is believed that if this reaction is an acid-catalyzed reaction, then with increased acidity, the catalytic activity should increase and AlCl$_3$ should have been the most active. However, in this example the maximum activity was observed for the DSIL at 0.33 and indeed all three of the DSILs had higher activity than AlCl$_3$.

The best catalyst in this example was DSIL at 0.33 (100% conversion with 97.2% selectivity; Table 12), where the [AlCl$_4$]$^-$ anion is the predominant species. Nonetheless when the use of [HN$_{222}$][AlCl$_4$] was investigated, relatively low activity (85% conversion with 70.1% selectivity) was found. Further to note that significant activity was found using DSIL because synergetic effect of Zn species combined with AlCl$_4^-$ anion in DSIL. DSIL at 0.33 exhibited even more activity than most acidic [HN$_{222}$][Al$_2$Cl$_7$] IL due to easily accessible catalytic Al$^{3+}$ centers to substrates. These catalytic activity differences are well correlated with the FT-IR data of Al—Cl stretch. This further confirmed the role of the Zn species in the catalyst.

The recyclability of the DSIL catalyst in the Beckmann rearrangement reaction was investigated with the most active DSIL at 0.33. As noted above, when any of the DSILs was used as catalyst, a white precipitate formed. To reuse the catalyst, the reaction mixture was decanted and the catalyst was washed 2-3 times with acetonitrile. Further to this recovered catalyst, reactant was again charged into the reaction vial for the next run. The same procedure was continued up to a third 3$^{rd}$ cycle. The conversion in the 1$^{st}$, 2$^{nd}$, and 3$^{rd}$ cycle using DSIL in the Beckmann rearrangement of acetophenone oxime was 100, 97.3, 65.3% respectively.

Application of [HN$_{222}$]$_{2x}$[(1−x)AlCl$_3$+xZnCl$_4$] DSIL in Meyer-Schuster Rearrangement Reaction For the Meyer-Schuster rearrangement reaction, 1.0 mmol of phenylacetylene and 1.05 mmol of benzaldehyde were placed into a 5 mL screw top borosilicate glass vial and followed by addition of 0.1 mmol of catalyst under atmospheric of argon (using a glove bag). The screw top vial was equipped with Teflon coated magnetic stir bar. After addition of the reactants, the vial was capped using rubber septum, and sealed with Parafilm. The vial was then removed from the glove bag and the reaction mixture was heated in a temperature controlled oil bath with magnetic stirring at 90° C. for 24 h (Scheme 8). After 24 h, a small aliquot mixture was withdrawal from the reaction mixture and dissolved in ethyl acetate and monitored by using GC-MS and summarized in the Table 13.

Scheme 8. Meyer-Schuster rearrangement reaction.

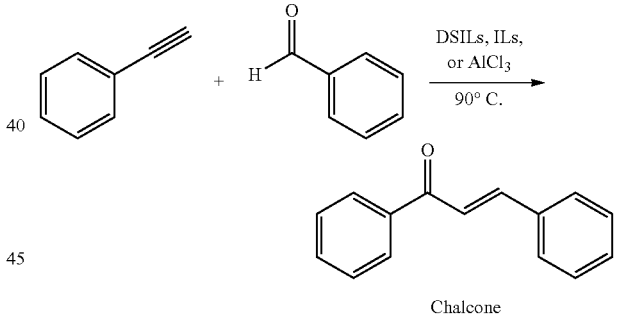

Chalcone

TABLE 13

Comparative catalytic activity in the Meyer-Schuster rearrangement.

| E. N. | Catalyst | Conversion of phenyl acetylene (%) | Selectivity of chalcone (%) |
|---|---|---|---|
| 1 | [HN$_{222}$]$_2$[ZnCl$_4$] | 0 | 0 |
| 2 | [HN$_{222}$][0.5AlCl$_3$ + 0.5ZnCl$_4$] | 50 | 12.6 |
| 3 | [HN$_{222}$]$_{0.6}$[0.6AlCl$_3$ + 0.4ZnCl$_4$] | 78 | 21 |
| 4 | [HN$_{222}$]$_{0.66}$[0.67AlCl$_3$ + 0.33ZnCl$_4$] | 100 | 79 |
| 5 | AlCl$_3$ | 100 | 60.6 |
| 6 | [HN$_{222}$][AlCl$_4$] | 100 | 42 |
| 7 | [HN$_{222}$][Al$_2$Cl$_7$] | 100 | 86 |

Reaction conditions: catalyst (0.1 mmol), phenyl acetylene (1 mmol), benzaldehyde (1.05 mmol), reaction temperature (90° C.) and time (24 h). Side product is oligomeric product of chalcone.

The Lewis acidity compared by FT-IR noted above (FIG. 20), suggested that $AlCl_3$ was the most acidic. It is believes that if this reaction is acid-catalyzed reaction, then with increased acidity, the catalytic activity should increase and $AlCl_3$ should have been the most active. However, in this example the maximum activity was observed for the DSIL at 0.33 and indeed all three of the DSILs had higher activity than $AlCl_3$.

The best catalyst in this example was DSIL at 0.33 (100% conversion with 79% selectivity; Table 13), where the $[AlCl_4]^-$ anion is the predominant species. Nonetheless when the use of $[HN_{222}][AlCl_4]$ was investigated, relatively low activity (100% conversion with 42% selectivity) was found. Further to note that significant activity found using DSIL because synergetic effect of Zn species combined with $AlC_{14}^-$ anion in DSIL. These catalytic activity differences are well correlated with the FT-IR data of Al—Cl stretch. This further confirmed the vital role of presence of Zn species in catalyst.

Application of $[HN_{222}]_{2x}[(1-x)AlCl_3+xZnCl_4]$ DSIL in Heterocyclic Quinoline Synthesis For the heterocyclic quinoline reaction, 1.0 mmol of phenylacetylene, 1.0 mmol of aniline, and 1.05 mmol of benzaldehyde were placed into a 5 mL screw top borosilicate glass vial and followed by addition of 0.1 mmol of catalyst under atmospheric of argon (using a glove bag). The screw top vial was equipped with Teflon coated magnetic stir bar. After addition of the reactants, the vial was capped using rubber septum, and sealed with Parafilm. The vial was then removed from the glove bag and the reaction mixture was heated in a temperature controlled oil bath with magnetic stirring at 90° C. for 24 h (Scheme 9). After 24 h, a small aliquot mixture was withdrawal from the reaction mixture and dissolved in ethyl acetate and monitored by using GC-MS and summarized in the Table 14.

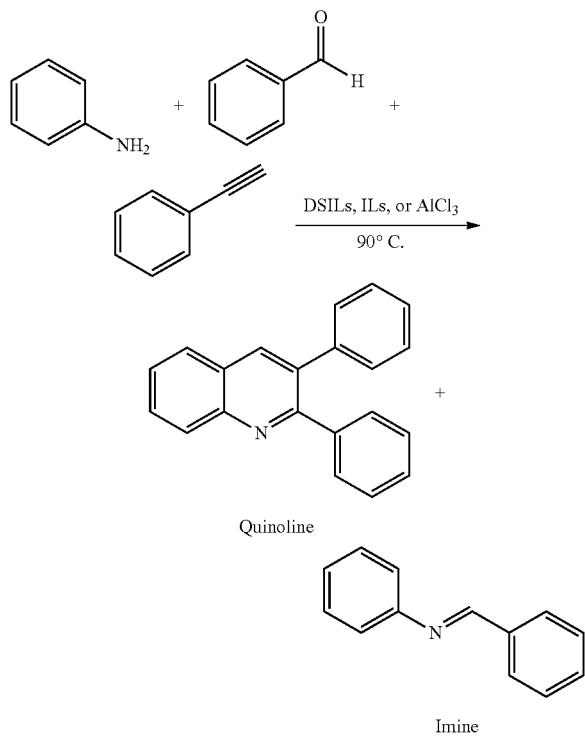

Scheme 9. Heterocyclic quinoline reaction.

TABLE 14

Comparative catalytic activity in the Meyer-Schuster rearrangement.

| E. N. | Catalyst | Conversion of phenyl acetylene (%) | Selectivity of chalcone (%) |
|---|---|---|---|
| 1 | $[HN_{222}]_2[ZnCl_4]$ | 75.8 | 17 |
| 2 | $[HN_{222}]_{0.66}[0.67AlCl_3 + 0.33ZnCl_4]$ | 100 | 92 |
| 3 | $[HN_{222}][AlCl_4]$ | 100 | 88 |
| 4 | $[HN_{222}][Al_2Cl_7]$ | 100 | 60 |

Reaction condition: Catalyst (0.1 mmol), acetophenone oxime (1 mmol), acetonitrile (2 mL), reaction temperature (90° C.) and time (24 h). Side product is imine.

The best catalyst in this example was DSIL at 0.33 (100% conversion with 92% selectivity; Table 14), where the $[AlCl_4]^-$ anion is the predominant species. $[HN_{222}][AlCl_4]$ showed relatively low activity at 100% conversion with 88% selectivity. The significant activity found using DSIL may be due to synergetic effect of Zn species combined with $AlCl_4^-$ anion in DSIL. It is believed that DSIL at 0.33 exhibited even more activity than most acidic $[HN_{222}][Al_2Cl_7]$ IL due to easily accessible catalytic $Al^{3+}$ centers to substrates. These catalytic activity differences are well correlated with the FT-IR data of Al—Cl stretch. This further confirm the role of Zn species in the catalyst.

Preparation of Double Salt Ionic Liquids (DSIL)

General: Anhydrous benzene, $FeCl_3$ (97% purity), and anhydrous ethanol were purchased from Sigma-Aldrich (St. Louis, Mo.); while $AlCl_3$ (99% purity) and triethylammonium hydrochloride (98% purity) were purchased from Alfa Aesar (Ward Hill, Mass.). Dimethyl sulfoxide-$d_6$ (99.9% purity), used as NMR solvent, was purchased from Cambridge Isotope Laboratory, Inc (Andover, Mass.).

Examples 1-6 are DSIL Prepared by Nonstoichiometric Addition of a Hallometallate IL to a Second Hallometallate IL Example 1-I. Triethylammonium [Chloroaluminate-chlorozinchate [$HN_{222}$]1.50][$0.50Al_2Cl_7$+ $0.50ZnCl_4$]

In an Ar-filled glove bag, a 20 mL borosilicate glass screw-top vial equipped with a Teflon coated magnetic stir bar was loaded with 5 mmol of liquid $[HN_{222}][Al_2Cl_4]$ followed by addition of 5 mmol of white, crystalline $[HN_{222}]_2[ZnCl_4]$. After addition, the mixture was observed to form a mixture of liquid and white wet solid. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a viscous, faint brown liquid. The reaction was monitored at 1 h, 2 h and 4 h, and a color change from faint brown to pink was observed. After 4 h the vial was removed from the oil bath and left to cool on the bench top, giving a highly viscous, pink liquid. $^1H$ NMR (55° C., neat, DMSO-$d_6$ lock) δ (ppm) 5.62 (bs, 1H), 2.42 (m, 6H), 0.48 (m, 9H); $^{27}Al$ NMR (55° C., neat, DMSO-$d_6$ lock) δ (ppm) 103.33; $^{13}C$ NMR (55° C., neat, DMSO-$d_6$ lock) δ (ppm) 47.42, 8.71.

Example 1-II. Triethylammonium [Chloroaluminate-Chlorozinchate][$HN_{222}$]$_{1.40}$[$0.60Al_2Cl_7$+ $0.40ZnCl_4$]

In an Ar-filled glove bag, a 20 mL borosilicate glass screw-top vial equipped with a Teflon coated magnetic stir bar was loaded with 6 mmol of liquid [HN$_{222}$][Al$_2$C$_4$] followed by addition of 4 mmol of white, crystalline [HN$_{222}$]$_2$[ZnCl$_4$]. After addition, the mixture was observed to form a mixture of liquid and white wet solid. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a viscous, brown liquid. The reaction was monitored at 1 h, 2 h and 4 h, and a color change from faint brown to pink was observed. After 4 h the vial was removed from oil bath and left to cool on the bench top, giving a gray solid. $^1$H NMR (55° C., neat, DMSO-d$_6$ lock) δ (ppm) 5.12 (bs, 1H), 2.44 (m, 6H), 0.50 (m, 9H); $^{27}$Al NMR (55° C., neat, DMSO-d$_6$ lock) δ (ppm) 103.35.

Example 1-III. Triethylammonium [Chloroaluminate-Chlorozinchate][HN$_{222}$]$_{1.33}$[10.67Al$_2$Cl$_7$+0.33ZnCl$_4$]

In an Ar-filled glove bag, a 20 mL borosilicate glass screw-top vial equipped with a Teflon coated magnetic stir bar was loaded with 6.7 mmol of liquid [HN$_{222}$][Al$_2$Cl$_4$] followed by addition of 3.3 mmol of white, crystalline [HN$_{222}$]$_2$[ZnCl$_4$]. After addition, the mixture was observed to form a mixture of liquid and white wet solid. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a viscous, brown liquid. The reaction was monitored at 1 h, 2 h and 4 h, and a color change from faint brown to pink was observed. After 4 h the vial was removed from oil bath and left to cool on the bench top, giving a gray crystalline solid. $^1$H NMR (55° C., neat, DMSO-d$_6$ lock) δ (ppm) 5.12 (bs, 1H), 2.44 (m, 6H), 0.50 (m, 9H); $^{27}$Al NMR (55° C., neat, DMSO-d$_6$ lock) δ (ppm) 103.35; $^{13}$C NMR (55° C., neat, DMSO-d$_6$ lock) δ (ppm) 47.90, 8.85.

Example 1-IV. Triethylammonium [Chloroaluminate Chlorozinchate][HN$_{222}$]$_{1.3}$[0.70Al$_2$Cl$_7$+0.30ZnCl$_4$]

In an Ar-filled glove bag, a 5 mL borosilicate glass screw-top vial equipped with a Teflon coated magnetic stir bar was loaded with 0.7 mmol of liquid [HN$_{222}$][Al$_2$Cl$_4$] followed by addition of 0.3 mmol of white, crystalline [HN$_{222}$]$_2$[ZnCl$_4$]. After addition, the mixture was observed to form a mixture of liquid and white wet solid. The vial was capped and sealed with Parafilm. It was then removed from the glove bag, and heated with magnetic stirring in a temperature-controlled oil bath at 75° C. The mixture liquefied within one min to give a viscous, milky white liquid. The reaction was monitored at 1 h, 2 h and 4 h, and no further change was observed. After 4 h the vial was removed from oil bath and left to cool on the bench top, giving a milky white solid. NMR (55° C., neat, DMSO-d$_6$ lock) δ (ppm) 4.84 (bs, 1H), 2.51 (m, 6H), 0.57 (m, 9H); $^{27}$Al NMR (55° C., neat, DMSO-d$_6$ lock) δ (ppm) 103.37 (large), 97.21 (small).

Example 1-V. Triethylammonium [Chloroaluminate Chlorozinchate][HN$_{222}$]$_{1.10}$[0.90Al$_2$Cl$_7$+0.10ZnCl$_4$]

In an Ar-filled glove bag, a 5 mL borosilicate glass screw-top vial equipped with a Teflon coated magnetic stir bar was loaded with 0.9 mmol of liquid [HN$_{222}$][Al$_2$C$_4$] followed by addition of 0.1 mmol of white, crystalline [HN$_{222}$]$_2$[ZnCl$_4$]. After addition, the mixture was observed to form a mixture of liquid and white wet solid. The vial was capped and sealed with Parafilm. It was then removed from the glove bag, and heated with magnetic stirring in a temperature-controlled oil bath at 75° C. The mixture liquefied within one min to give a viscous, brown liquid. The reaction was monitored at 1 h, 2 h and 4 h, and no further change was observed. After 4 h the vial was removed from oil bath and left to cool on the bench top, giving a gray viscous liquid. $^1$H NMR (55° C., neat, DMSO-d$_6$ lock) δ (ppm) 4.61 (bs, 1H), 2.43 (m, 6H), 0.51 (m, 9H); $^{27}$Al NMR (55° C., neat, DMSO-d$_6$ lock) δ (ppm) 106.41, 97.24.

Example 1-VI. Triethylammonium [Chloroaluminate Chlorozinchate][HN$_{222}$]$_{1.50}$[0.50Al$_2$Cl$_7$+0.50ZnCl$_4$]

In an Ar-filled glove bag, a 20 mL borosilicate glass screw-top vial equipped with a Teflon coated magnetic stir bar was loaded with 2 mmol of liquid [HN$_{222}$][Al$_2$C$_4$] in a 2 mL of benzene followed by addition of 2 mmol of white, crystalline [HN$_{222}$]$_2$[ZnCl$_4$]. After addition, the mixture was observed to form a biphasic layer contains colorless clear upper layer and hazy colorless lower layer. The vial was capped using a cap with a Teflon/silicon (10/90) septum, and sealed with Parafilm. It was then removed from the glove bag, and heated with magnetic stirring in a temperature-controlled oil bath at 75° C. The reaction was monitored at 1 h, 2 h and 4 h, and a color change of the lower phase was observed, from colorless to pink liquid. After 4 h, the vial was removed from oil bath and left to cool on the bench top, giving a biphasic layer contains colorless clear upper layer and hazy colorless lower layer. $^1$H NMR (27° C., neat (After evaporation of benzene), DMSO-d$_6$ lock) δ (ppm) 5.80 (bs, 1H), 2.38 (m, 6H), 0.45 (m, 9H); $^{27}$Al NMR (27° C., neat (after evaporation of benzene), DMSO-d$_6$ lock) δ (ppm) 103.53.

Example 2-I. Triethylammonium [Chloroaluminate Chloroferrate][HN$_{222}$][0.20AlCl$_4$+0.80FeCl$_4$]

In an Ar-filled glove bag, a 20 mL borosilicate glass screw-top vial equipped with a Teflon coated magnetic stir bar was loaded with 2 mmol of white solid [HN$_{222}$][AlCl$_4$], followed by addition of 8 mmol of green, crystalline [HN$_{222}$][FeCl$_4$]. After addition, a heterogeneous solid system was observed, composed by white and green solids. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a dark, green liquid. The reaction was monitored at 1 h, 2 h and 4 h, and no further change was observed. After 4 h, the vial was removed from oil bath and left to cool on the bench top, giving a homogeneous green solid. $^1$H NMR (55° C., neat, DMSO-d$_6$ lock) δ (ppm) 195.64 (bs, large), 179.88 (bs, small); $^{27}$Al NMR (55° C., neat, DMSO-d$_6$ lock) δ (ppm) 331.21; $^{13}$C NMR (55° C., neat, DMSO-d$_6$ lock) δ (ppm) 315.87, 306.17.

Example 2-II. Triethylammonium [Chloroaluminate Chloroferrate][HN$_{222}$][0.25AlCl$_4$+0.75FeCl$_4$]

In an Ar-filled glove bag, a 20 mL borosilicate glass screw-top vial equipped with a Teflon coated magnetic stir bar was loaded with 2.5 mmol of white solid [HN$_{222}$]

[AlCl$_4$], followed by addition of 7.5 mmol of green, crystalline [HN$_{222}$][FeCl$_4$]. After addition, a heterogeneous solid system was observed, composed by white and green solids. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a dark, green liquid. The reaction was monitored at 1 h, 2 h and 4 h, and no further change was observed. After 4 h the vial was removed from oil bath and left to cool on the bench top, giving a homogeneous green solid. $^1$H NMR (55° C., neat, DMSO-d$_6$ lock) δ (ppm) 185.42 (bs, large), 170.66 (bs, small); $^{27}$Al NMR (55° C., neat, DMSO-d$_6$ lock) δ (ppm) 317.55.

Example 2-III. Triethylammonium [Chloroaluminate Chloroferrate][HN$_{222}$][0.33AlCl$_4$+0.67FeCl$_4$]

In an Ar-filled glove bag, a 20 mL borosilicate glass screw-top vial equipped with a Teflon coated magnetic stir bar was loaded with 3.3 mmol of white solid [HN$_{222}$][AlCl$_4$] followed by addition of 6.7 mmol of green, crystalline [HN$_{222}$][FeCl$_4$]. After addition, a heterogeneous solid system was observed, composed by white and green solids. The vial was capped using a cap with a Teflon/silicon (10/90) septum, and sealed with Parafilm. It was then removed from the glove bag, and heated with magnetic stirring in a temperature-controlled oil bath at 7° C. The mixture liquefied within one min to give a, dark green liquid. The reaction was monitored at 1 h, 2 h and 4 h, and no further change was observed. After 4 h the vial was removed from oil bath and left to cool on the bench top, giving a homogeneous green solid.

Example 2-IV. Triethylammonium [Chloroaluminate Chloroferrate][HN$_{222}$][0.40AlCl$_4$+0.60FeCl$_4$]

In an Ar-filled glove bag, a 20 mL borosilicate glass screw-top vial equipped with a Teflon coated magnetic stir bar was loaded with 4 mmol of white solid [HN$_{222}$][AlCl$_4$] followed by addition of 6 mmol of green, crystalline [HN$_{222}$][FeCl$_4$]. After addition, the mixture was observed to form a mixture of white and green colors of two solids. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a, dark green liquid. The reaction was monitored at 1 h, 2 h and 4 h, and no further change was observed. After 4 h the vial was removed from oil bath and left to cool on the bench top, giving a homogeneous green solid. $^1$H NMR (55° C., neat, DMSO-d$_6$ lock) δ (ppm) 149.47 (bs, large), 138.65 (bs, small); $^{27}$Al NMR (55° C., neat, DMSO-d$_6$ lock) δ (ppm) 278.29.

Example 2-V. Triethylammonium [Chloroaluminate Chloroferrate][HN$_{222}$][0.50AlCl$_4$+0.50FeCl$_4$]

In an Ar-filled glove bag, a 20 mL borosilicate glass screw-top vial equipped with a Teflon coated magnetic stir bar was loaded with 5 mmol of white solid [HN$_{222}$][AlCl$_4$] followed by addition of 5 mmol of green, crystalline [HN$_{222}$][FeCl$_4$]. After addition, the mixture was observed to form a mixture of white and green colors of two solids. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a, dark green liquid. The reaction was monitored at 1 h, 2 h and 4 h, and no further change was observed. After 4 h the vial was removed from oil bath and left to cool on the bench top, giving a homogeneous green solid. $^1$H NMR (55° C., neat, DMSO-d$_6$ lock) δ (ppm) 121.52; $^{27}$Al NMR (55° C., neat, DMSO-d$_6$ lock) δ (ppm) 240.46; $^{13}$C NMR (55° C., neat, DMSO-d$_6$ lock) δ (ppm) 223.68, 202.09.

Example 2-VI. Triethylammonium [Chloroaluminate Chloroferrate][HN$_{222}$][0.60AlCl$_4$+0.40FeCl$_4$]

In an Ar-filled glove bag, a 20 mL borosilicate glass screw-top vial equipped with a Teflon coated magnetic stir bar was loaded with 6 mmol of white solid [HN$_{222}$][AlCl$_4$] followed by addition of 4 mmol of green, crystalline [HN$_{222}$][FeCl$_4$]. After addition, the mixture was observed to form a mixture of white and green colors of two solids. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a, green liquid. The reaction was monitored at 1 h, 2 h and 4 h, and no further change was observed. After 4 h the vial was removed from oil bath and left to cool on the bench top, giving a homogeneous green solid. $^1$H NMR (55° C., neat, DMSO-d$_6$ lock) δ (ppm) 103.38; $^{27}$Al NMR (55° C., neat, DMSO-d$_6$ lock) δ (ppm) 223.22.

Example 2-VII. Triethylammonium [Chloroaluminate Chloroferrate][HN$_{222}$][0.67AlCl$_4$+0.33FeCl$_4$]

In an Ar-filled glove bag, a 20 mL borosilicate glass screw-top vial equipped with a Teflon coated magnetic stir bar was loaded with 6.7 mmol of white solid [HN$_{222}$][AlCl$_4$] followed by addition of 3.3 mmol of green, crystalline [HN$_{222}$][FeCl$_4$]. After addition, the mixture was observed to form a mixture of white and green colors of two solids. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a, green liquid. The reaction was monitored at 1 h, 2 h and 4 h, and no further change was observed. After 4 h the vial was removed from oil bath and left to cool on the bench top, giving a homogeneous green solid. $^1$H NMR (55° C., neat, DMSO-d$_6$ lock) δ (ppm) 82.26; $^{27}$Al NMR (55° C., neat, DMSO-d$_6$ lock) δ (ppm) 199.04; $^{13}$C NMR (55° C., neat, DMSO-d$_6$ lock) δ (ppm) 152.51, 123.72.

Example 2-VIII. Triethylammonium [Chloroaluminate Chloroferrate][HN$_{222}$][0.80AlCl$_4$+0.20FeCl$_4$]

In an Ar-filled glove bag, a 20 mL borosilicate glass screw-top vial equipped with a Teflon coated magnetic stir bar was loaded with 8 mmol of white solid [HN$_{222}$][AlCl$_4$] followed by addition of 2 mmol of green, crystalline [HN$_{222}$][FeCl$_4$]. After addition, the mixture was observed to form a mixture of white and green colors of two solids. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a, yellow liquid. The reaction was monitored at 1 h, 2 h and 4 h, and no further change was observed. After 4 h the vial was removed from oil bath and left to cool on the bench top, giving a homogeneous green solid. $^{1}$H NMR (55° C., neat, DMSO-d$_6$ lock) δ (ppm) 50.40; $^{27}$Al NMR (55° C., neat, DMSO-d$_6$ lock) δ (ppm) 162.37; $^{13}$C NMR (55° C., neat, DMSO-d$_6$ lock) δ (ppm) 119.17, 86.99.

Example 2-IX Triethylammonium [Chloroaluminate Chloroferrate][HN$_{222}$][0.50AlCl$_4$+0.50FeCl$_4$]

In an Ar-filled glove bag, a 20 mL borosilicate glass screw-top vial equipped with a Teflon coated magnetic stir bar was loaded with 2 mmol of white solid [HN$_{222}$][AlCl$_4$] in a 2 mL of benzene followed by addition of 2 mmol of green, crystalline [HN$_{222}$][FeCl$_4$]. After addition, the mixture was observed to form a biphasic layer contains clear faint yellow upper layer and dark yellow lower layer. The vial was capped using a cap with a Teflon/silicon (10/90) septum, and sealed with Parafilm. It was then removed from the glove bag, and heated with magnetic stirring in a temperature-controlled oil bath at 75° C. The reaction was monitored at 1 h, 2 h and 4 h, and a color change of the lower layer from dark yellow to dark brown was observed. After 4 h the vial was removed from oil bath and left to cool on the bench top, giving a biphasic layer contains clear yellow upper layer and dark brown lower layer. $^{1}$H NMR (55° C., neat (After evaporation of benzene), DMSO-d$_6$ lock) δ (ppm) 118.69; $^{27}$Al NMR (55° C., neat (After evaporation of benzene), DMSO-d$_6$ lock) δ (ppm) 242.31.

Example 3-I. Triethylammonium [Chloroaluminate Chloroferrate][HN$_{222}$][10.50Al$_2$Cl$_7$+0.50FeCl$_4$]

In an Ar-filled glove bag, a 5 mL borosilicate glass screw-top vial equipped with a Teflon coated magnetic stir bar was loaded with 1 mmol of very faint brown liquid [HN$_{222}$][Al$_2$Cl$_7$] followed by addition of 1 mmol of green, crystalline [HN$_{222}$][FeCl$_4$]. After addition, the mixture was observed to form a mixture of wet dark brown solid. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a, dark brown liquid. The reaction was monitored at 1 h, 2 h and 4 h, and no further change was observed. After 4 h the vial was removed from oil bath and left to cool on the bench top, giving a viscous dark black liquid.

Example 4-I. Triethylammonium [Chlorozinckate Chloroferrate][HN$_{222}$]$_{1.50}$[0.5ZnCl$_4$+0.5FeCl$_4$]

In an Ar-filled glove bag, a 20 mL borosilicate glass screw-top vial equipped with a Teflon coated magnetic stir bar was loaded with 5 mmol of white, crystalline [HN$_{222}$]$_2$[ZnCl$_4$] followed by addition of 5 mmol of green, crystalline [HN$_{222}$][FeCl$_4$]. After addition, the mixture was observed to form a mixture of white and green solids. The vial was capped using a cap with a Teflon/silicon (10/90) septum, and sealed with Parafilm. It was then removed from the glove bag, and heated with a magnetic stirrer in a temperature-controlled oil bath at 75° C. The mixture liquefied within one min to give a yellow gold viscous liquid. The reaction was monitored at 1 h, 2 h and 4 h, and no further change was observed. After 4 h the vial was removed from oil bath and left to cool on the bench top, giving a homogeneous pale yellow solid.

Example 5-I Triethylammonium [Chloroaluminate-Chlorozinchate][HN$_{222}$][0.33Al$_2$Cl$_7$+0.67ZnCl$_3$]

In an Ar-filled glove bag, a 10 mL borosilicate glass screw-top vial equipped with a Teflon coated magnetic stir bar was loaded with 3.3 mmol of liquid [HN$_{222}$][Al$_2$C$_4$] followed by addition of 6.7 mmol of colorless, viscous liquid [HN$_{222}$][ZnCl$_3$]. The vial was capped using a cap with a Teflon/silicon (10/90) septum, and sealed with Parafilm. It was then removed from the glove bag, and heated with magnetic stirring in a temperature-controlled oil bath at 75° C. After 4 h the vial was removed from oil bath and left to cool on the bench top, giving a homogeneous brown viscous liquid.

Example 6-I. Triethylammonium [Chloroaluminate-Hydrogensulfate][HN$_{222}$][0.8Al$_2$Cl$_7$+0.2HSO$_4$]

In an Ar-filled glove bag, a 10 mL borosilicate glass screw-top vial equipped with a Teflon coated magnetic stir bar was loaded with 8 mmol of liquid [HN$_{222}$][Al$_2$Cl$_4$] followed by addition of 2 mmol of pale yellow solid [HN$_{222}$][HSO$_4$]. After addition, the mixture was observed to form a mixture of brown liquid and white wet solid. The vial was capped and sealed with Parafilm. It was then removed from the glove bag, and heated with magnetic stirring in a temperature-controlled oil bath at 75° C. After 12 h the vial was removed from oil bath and left to cool on the bench top, giving a homogeneous black viscous liquid.

Example 6-II. Triethylammonium [Chloroaluminate-Hydrogensulfate][HN$_{222}$][0.67Al$_2$Cl$_7$+0.33HSO$_4$]

In an Ar-filled glove bag, a 10 mL borosilicate glass screw-top vial equipped with a Teflon coated magnetic stir bar was loaded with 6.7 mmol of liquid [HN$_{222}$][Al$_2$Cl$_4$] followed by addition of 3.3 mmol of pale yellow solid [HN$_{222}$][HSO$_4$]. After addition, the mixture was observed to form a mixture of brown liquid and white wet solid. The vial was capped and sealed with Parafilm. It was then removed from the glove bag, and heated with magnetic stirring in a temperature-controlled oil bath at 75° C. After 12 h the vial was removed from oil bath and left to cool on the bench top, giving a homogeneous black highly viscous liquid.

Example 6-III. Triethylammonium [Chloroaluminate-Hydrogensulfate][HN$_{222}$][0.5Al$_2$Cl$_7$+0.5HSO$_4$]

In an Ar-filled glove bag, a 10 mL borosilicate glass screw-top vial equipped with a Teflon coated magnetic stir bar was loaded with 5 mmol of liquid [HN$_{222}$][Al$_2$Cl$_4$] followed by addition of 5 mmol of pale yellow solid [HN$_{222}$][HSO$_4$]. After addition, the mixture was observed to form a mixture of brown liquid and white wet solid. The vial was capped and sealed with Parafilm. It was then removed from the glove bag, and heated with magnetic stirring in a temperature-controlled oil bath at 75° C. After 12 h the vial was removed from oil bath and left to cool on the bench top, giving a homogeneous greyish white gel.

Example 6-IV. Triethylammonium [Chloroaluminate-Hydrogensulfate][HN$_{222}$][0.33Al$_2$Cl$_7$+0.67HSO$_4$]

In an Ar-filled glove bag, a 10 mL borosilicate glass screw-top vial equipped with a Teflon coated magnetic stir bar was loaded with 3.3 mmol of liquid $[HN_{222}][Al_2Cl_4]$ followed by addition of 6.7 mmol of pale yellow solid $[HN_{222}][HSO_4]$. After addition, the mixture was observed to form a mixture of liquid and white wet solid. The vial was capped and sealed with Parafilm. It was then removed from the glove bag, and heated with magnetic stirring in a temperature-controlled oil bath at 75° C. After 12 h the vial was removed from oil bath and left to cool on the bench top, giving a faint brown gel.

Examples 7-8 are DSIL Prepared by Nonstoichiometric Addition of Salts or Addition of Neutral Metal Halides to ILs Example 7-I. Triethylammonium [Chloroaluminate Chloroferrate]$[HN_{222}]_{0.5}[0.5AlCl_4+0.5FeCl_3]$ In an Ar-filled glove bag, a 20 mL borosilicate glass screw-top vial equipped with a Teflon coated magnetic stir bar was loaded with 5 mmol of very faint brown liquid $[HN_{222}][AlCl_4]$ followed by addition of 5 mmol of green solid $FeCl_3$. After addition, the mixture was observed to form a mixture of black slurry. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a red brown liquid. The reaction was monitored at 1 h, 2 h and 4 h, and no further change was observed. After 4 h the vial was removed from oil bath and left to cool on the bench top, giving a viscous red brown liquid.

Example 8-I. Triethylammonium [Chlorozinckate Chloroaluminate]$[HN_{222}][0.5AlCl_3+0.5ZnCl_4]$ In an Ar-filled glove bag, a 20 mL borosilicate glass screw-top vial equipped with a Teflon coated magnetic stir bar was loaded with 5 mmol of white, crystalline $[HN_{222}]_2[ZnCl_4]$ followed by addition of 5 mmol of white solid $AlCl_3$. After addition, a mixture of two solids was observed. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a colorless viscous liquid. The reaction was monitored at 1 h, 2 h and 4 h, and no further change was observed. After 4 h the vial was removed from oil bath and left to cool on the bench top, giving a homogeneous colorless viscous liquid.

Example 8-II. Triethylammonium [Chlorozinckate Chloroaluminate]$[HN_{222}]_{0.8}[0.6AlCl_3+0.4ZnCl_4]$ In an Ar-filled glove bag, a 20 mL borosilicate glass screw-top vial equipped with a Teflon coated magnetic stir bar was loaded with 4 mmol of white, crystalline $[HN_{222}]_2[ZnCl_4]$ followed by addition of 6 mmol of white solid $AlCl_3$. After addition, a mixture of two solids was observed. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a colorless viscous liquid. The reaction was monitored at 1 h, 2 h and 4 h, and no further change was observed. After 4 h the vial was removed from oil bath and left to cool on the bench top, giving a homogeneous brown soft solid.

Example 8-III. Triethylammonium [Chlorozinckate Chloroaluminate]$[HN_{222}]_{0.66}[0.67AlCl_3+0.33ZnCl_4]$ In an Ar-filled glove bag, a 20 mL borosilicate glass screw-top vial equipped with a Teflon coated magnetic stir bar was loaded with 3.3 mmol of white, crystalline $[HN_{222}]_2[ZnCl_4]$ followed by addition of 6.7 mmol of white solid $AlCl_3$. After addition, a mixture of two solids was observed. The vial was capped using a cap with a Teflon/silicon (10/90) septum, and sealed with Parafilm. It was then removed from the glove bag, and heated with magnetic stirring in a temperature-controlled oil bath at 75° C. The mixture liquefied within one min to give a, viscous liquid. The reaction was monitored at 1 h, 2 h and 4 h, and no further change was observed. After 4 h the vial was removed from oil bath and left to cool on the bench top, giving a homogeneous white hard solid.

Example 9 Includes Application of DSIL in Beckmann Rearrangement Reaction

Example 9-I. Beckmann Reaction Using $[HN_{222}]_4[ZnCl_4]$

In an Ar-filled glove bag, a 5 mL borosilicate glass screw-top vial equipped with a Teflon coated magnetic stir bar was loaded with 0.1 mmol of $[HN_{222}]_2[ZnCl_4]$ followed by addition of 2 mL of acetonitrile as a solvent and further acetophenone oxime added into the reaction. After addition, the mixture was observed to form a homogeneous liquid. The vial was capped using a rubber septum, and sealed with Parafilm. The vial was then removed from the glove bag and the reaction mixture was heated in a temperature controlled oil bath with magnetic stirring at 80° C. for 3 h. After 3 h, a small aliquot mixture was withdrawal from the reaction mixture and monitored by using GC-MS.

Example 9-II. Beckmann Reaction Using $[HN_{222}][0.5AlCl_3+0.5ZnCl_4]$

In an Ar-filled glove bag, a 5 mL borosilicate glass screw-top vial equipped with a Teflon coated magnetic stir bar was loaded with 0.1 mmol of $[HN_{222}][0.5AlCl_3+0.5ZnCl_4]$ followed by addition of 2 mL of acetonitrile as a solvent and further acetophenone oxime added into the reaction. After addition, the mixture was observed to form a white solid precipitate at the bottom. The vial was capped using a rubber septum, and sealed with Parafilm. The vial was then removed from the glove bag and the reaction mixture was heated in a temperature controlled oil bath with magnetic stirring at 80° C. for 3 h. After 3 h, a small aliquot mixture was withdrawal from the reaction mixture and monitored by using GC-MS.

Example 9-III. Beckmann Reaction Using $[HN_{222}]_{0.66}[0.67AlCl_3+0.33ZnCl_4]$ In an Ar-filled glove bag, a 5 mL borosilicate glass screw-top vial equipped with a Teflon coated magnetic stir bar was loaded with 0.1 mmol of $[HN_{222}]0.66[0.67AlCl_3+0.33ZnCl_4]$ followed by addition of 2 mL of acetonitrile as a solvent and further acetophenone oxime added into the reaction. After addition, the mixture was observed to form a white solid precipitate at the bottom. The vial was capped using a rubber septum, and sealed with Parafilm. The vial was then removed from the glove bag and the reaction mixture was heated in a temperature controlled oil bath with magnetic stirring at 80° C. for 3 h. After 3 h, a small aliquot mixture was withdrawal from the reaction mixture and monitored by using GC-MS.

Example 9-IV. Beckmann Reaction Using [HN$_{222}$][Al$_2$Cl$_7$]

In an Ar-filled glove bag, a 5 mL borosilicate glass screw-top vial equipped with a Teflon coated magnetic stir bar was loaded with 0.1 mmol of [HN$_{222}$][Al$_2$Cl$_7$] followed by addition of 2 mL of acetonitrile as a solvent and further acetophenone oxime added into the reaction. After addition, the mixture was observed to form a white solid precipitate at the bottom. The vial was capped using a rubber septum, and sealed with Parafilm. The vial was then removed from the glove bag and the reaction mixture was heated in a temperature controlled oil bath with magnetic stirring at 80° C. for 3 h. After 3 h, a small aliquot mixture was withdrawal from the reaction mixture and monitored by using GC-MS.

Example 10 Includes Application of DSIL in Meyer-Schuster Rearrangement Reaction Example 10-I. Meyer-Schuster Rearrangement Reaction Using [HN$_{222}$]$_4$[ZnCl$_4$]

In an Ar-filled glove bag, a 5 mL borosilicate glass screw-top vial equipped with a Teflon coated magnetic stir bar was loaded with 1.0 mmol of phenylacetylene and 1.05 mmol of benzaldehyde and followed by addition of 0.1 mmol of [HN$_{222}$]$_2$[ZnCl$_4$] catalyst into the reaction. After addition, the mixture was observed to form a heterogeneous mixture of solid and liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, the reaction mixture was observed as a pale yellow sticky solid and further a small aliquot mixture was withdrawal from the reaction mixture and dissolved in ethyl acetate and monitored by using GC-MS.

Example 10-II. Meyer-Schuster Rearrangement Reaction Using [HN$_{222}$][0.5AlCl$_3$+0.5ZnCl$_4$]

In an Ar-filled glove bag, a 5 mL borosilicate glass screw-top vial equipped with a Teflon coated magnetic stir bar was loaded with 1.0 mmol of phenylacetylene and 1.05 mmol of benzaldehyde and followed by addition of 0.1 mmol of [HN$_{222}$][0.5AlCl$_3$+0.5ZnCl$_4$] into the reaction. After addition, the mixture was observed to form a biphasic liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, the reaction mixture was observed as a brown sticky solid and further a small aliquot mixture was withdrawal from the reaction mixture and dissolved in ethyl acetate and monitored by using GC-MS.

Example 10-III. Meyer-Schuster Rearrangement Reaction Using [HN$_{222}$]$_{0.8}$[0.6AlCl$_3$+0.4ZnCl$_4$]

In an Ar-filled glove bag, a 5 mL borosilicate glass screw-top vial equipped with a Teflon coated magnetic stir bar was loaded with 1.0 mmol of phenylacetylene and 1.05 mmol of benzaldehyde and followed by addition of 0.1 mmol of [HN$_{222}$]$_{0.8}$[0.6AlCl$_{3+0.4}$ZnCl$_4$] into the reaction. After addition, the mixture was observed to form a heterogeneous mixture contains sticky solid and liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, the reaction mixture was observed as a brown sticky solid and further a small aliquot mixture was withdrawal from the reaction mixture and dissolved in ethyl acetate and monitored by using GC-MS.

Example 10-IV. Meyer-Schuster Rearrangement Reaction Using [HN$_{222}$]$_{0.66}$[0.67AlCl$_3$+0.33ZnCl$_4$]

In an Ar-filled glove bag, a 5 mL borosilicate glass screw-top vial equipped with a Teflon coated magnetic stir bar was loaded with 1.0 mmol of phenylacetylene and 1.05 mmol of benzaldehyde and followed by addition of 0.1 mmol of [HN$_{222}$]$_{0.66}$[0.67AlCl$_3$+0.33ZnCl$_4$] into the reaction. After addition, the mixture was observed to form a heterogeneous mixture contains sticky solid and liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, the reaction mixture was observed as a dark brown sticky solid and further a small aliquot mixture was withdrawal from the reaction mixture and dissolved in ethyl acetate and monitored by using GC-MS.

Example 10-V. Meyer-Schuster Rearrangement Reaction Using AlCl$_3$

In an Ar-filled glove bag, a 5 mL borosilicate glass screw-top vial equipped with a Teflon coated magnetic stir bar was loaded with 1.0 mmol of phenylacetylene and 1.05 mmol of benzaldehyde and followed by addition of 0.1 mmol of AlCl$_3$ into the reaction. After addition, the mixture was observed to form a heterogeneous mixture of solid and liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, the reaction mixture was observed as a light brown sticky solid and further a small aliquot mixture was withdrawal from the reaction mixture and dissolved in ethyl acetate and monitored by using GC-MS.

Example 10-VI. Meyer-Schuster Rearrangement Reaction Using [HN$_{222}$][AlCl$_4$]

In an Ar-filled glove bag, a 5 mL borosilicate glass screw-top vial equipped with a Teflon coated magnetic stir bar was loaded with 1.0 mmol of phenylacetylene and 1.05 mmol of benzaldehyde and followed by addition of 0.1 mmol of [HN$_{222}$][AlCl$_4$] added into the reaction. After addition, the mixture was observed to form a heterogeneous mixture contains sticky solid and liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, reaction mixture was observed as a light brown sticky solid and further a small aliquot mixture was withdrawal from the reaction mixture and dissolved in ethyl acetate and monitored by using GC-MS.

Example 10-VII. Meyer-Schuster Rearrangement Reaction Using [HN$_{222}$][Al$_2$Cl$_7$]

In an Ar-filled glove bag, a 5 mL borosilicate glass screw-top vial equipped with a Teflon coated magnetic stir bar was loaded with 1.0 mmol of phenylacetylene and 1.05 mmol of benzaldehyde and followed by addition of 0.1 mmol of [HN$_{222}$][Al$_2$Cl$_7$] added into the reaction. After addition, the mixture was observed to form a biphasic liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, reaction mixture was observed as a dark brown sticky solid and further a small aliquot mixture was withdrawal from the reaction mixture and dissolved in ethyl acetate and monitored by using GC-MS.

Example 11 Includes Application of DSIL in Heterocyclic Synthesis Quinoline

Example 11-I. Quinoline Synthesis Using [HN$_{222}$]$_2$[ZnCl$_4$]

In an Ar-filled glove bag, a 5 mL borosilicate glass screw-top vial equipped with a Teflon coated magnetic stir bar was loaded with 1.0 mmol of phenylacetylene, 1.0 mmol of aniline, and 1.05 mmol of benzaldehyde and followed by addition of 0.1 mmol of [HN$_{222}$]$_2$[ZnCl$_4$] added into the reaction. After addition, the mixture was observed to form a turbid pale yellow solution. The vial was capped using a rubber septum, and sealed with Parafilm. The vial was then removed from the glove bag and the reaction mixture was heated in a temperature controlled oil bath with magnetic stirring at 90° C. for 24 h. After 24 h, reaction mixture was observed as a light green viscous liquid and further a small aliquot mixture was withdrawal from the reaction mixture and dissolved in ethyl acetate and monitored by using GC-MS.

Example 11-II. Quinoline Synthesis Using [HN$_{222}$]$_{0.66}$[0.67AlCl$_3$+0.33ZnCl$_4$]

In an Ar-filled glove bag, a 5 mL borosilicate glass screw-top vial equipped with a Teflon coated magnetic stir bar was loaded with 1.0 mmol of phenylacetylene, 1.0 mmol of aniline, and 1.05 mmol of benzaldehyde and followed by addition of 0.1 mmol of [HN$_{222}$]$_{0.66}$[0.67AlCl$_3$+0.33ZnCl$_4$] into the reaction. After addition, the mixture was observed to form a heterogeneous mixture contains sticky solid and liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, the reaction mixture was observed as a dark green solid and further a small aliquot mixture was withdrawal from the reaction mixture and dissolved in ethyl acetate and monitored by using GC-MS.

Example 11-III. Quinoline Synthesis Using [HN$_{222}$][AlCl$_4$]

In an Ar-filled glove bag, a 5 mL borosilicate glass screw-top vial equipped with a Teflon coated magnetic stir bar was loaded with 1.0 mmol of phenylacetylene, 1.0 mmol of aniline, and 1.05 mmol of benzaldehyde and followed by addition of 0.1 mmol of [HN$_{222}$][AlCl$_4$] into the reaction. After addition, the mixture was observed to form a heterogeneous mixture contains sticky solid and liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, the reaction mixture was observed as a dark green solid and further a small aliquot mixture was withdrawal from the reaction mixture and dissolved in ethyl acetate and monitored by using GC-MS.

Example 11-IV. Quinoline Synthesis Using [HN$_{222}$][Al$_2$Cl$_7$]

In an Ar-filled glove bag, a 5 mL borosilicate glass screw-top vial equipped with a Teflon coated magnetic stir bar was loaded with 1.0 mmol of phenylacetylene, 1.0 mmol of aniline, and 1.05 mmol of benzaldehyde and followed by addition of 0.1 mmol of [HN$_{222}$][Al$_2$Cl$_7$] into the reaction. After addition, the mixture was observed to form a biphasic sticky liquid and free flow liquid. The vial was capped using a rubber septum, and sealed with Parafilm. The vial was then removed from the glove bag and the reaction mixture was heated in a temperature controlled oil bath with magnetic stirring at 90° C. for 24 h. After 24 h, the reaction mixture was observed as a dark green sticky solid and further a small aliquot mixture was withdrawal from the reaction mixture and dissolved in ethyl acetate and monitored by using GC-MS.

The examples detailed above are summarized in Table 15. Evidence for the formation of new species was observed through physical transformations, color changes, and changes in spectra.

TABLE 15

Physical state of DSIL (selected examples)

| Anions | Example | Composition | Physical State |
|---|---|---|---|
| [(1 − x)Al$_2$Cl$_7$ + xZnCl$_4$] | 1-I | [HN$_{222}$]$_{1.50}$[0.50Al$_2$Cl$_7$ + 0.50ZnCl$_4$] | Viscous pink liquid |
| | 1-II | [HN$_{222}$]$_{1.40}$[0.60Al$_2$Cl$_7$ + 0.40ZnCl$_4$] | Gray crystals solid |
| | 1-III | [HN$_{222}$]$_{1.33}$[0.67Al$_2$Cl$_7$ + 0.33ZnCl$_4$] | Gray crystals solid |
| | 1-IV | [HN$_{222}$]$_{1.30}$[0.70Al$_2$Cl$_7$ + 0.30ZnCl$_4$] | Milky white solid |
| | 1-V | [HN$_{222}$]$_{1.10}$[0.90Al$_2$Cl$_7$ + 0.10ZnCl$_4$] | Gray liquid |
| [(1 − x)AlCl$_4$ + xFeCl$_4$] | 2-I | [HN$_{222}$][0.20AlCl$_4$ + 0.80FeCl$_4$] | Green solid |
| | 2-III | [HN$_{222}$][0.25AlCl$_4$ + 0.75FeCl$_4$] | Green solid |
| | 2-III | [HN$_{222}$][0.33AlCl$_4$ + 0.67FeCl$_4$] | Green solid |
| | 2-IV | [HN$_{222}$][0.40AlCl$_4$ + 0.60FeCl$_4$] | Green solid |
| | 2-V | [HN$_{222}$][0.50AlCl$_4$ + 0.50FeCl$_4$] | Green solid |

TABLE 15-continued

Physical state of DSIL (selected examples)

| Anions | Example | Composition | Physical State |
|---|---|---|---|
| | 2-VI | $[HN_{222}][0.60AlCl_4 + 0.40FeCl_4]$ | Green solid |
| | 2-VII | $[HN_{222}][0.67AlCl_4 + 0.33FeCl_4]$ | Green solid |
| | 2-VIII | $[HN_{222}][0.80AlCl_4 + 0.20FeCl_4]$ | Green solid |
| $[(1-x)Al_2Cl_7 + xFeCl_4]$ | 3-I | $[HN_{222}][0.50Al_2Cl_7 + 0.50FeCl_4]$ | Viscous dark black liquid |
| $[(1-x)ZnCl_4 + xFeCl_4]$ | 4-I | $[HN_{222}]_{1.5}[0.50ZnCl_4 + 0.50FeCl_4]$ | Pale green solid |
| $[(1-x)Al_2Cl_7 + xZnCl_3]$ | 5-I | $[HN_{222}][0.33AlCl_3 + 0.67ZnCl_3]$ | Black viscous liquid |
| $[(1-x)Al_2Cl_7 + xHSO_4]$ | 6-I | $[HN_{222}][0.8Al_2Cl_7 + 0.2HSO_4]$ | Black highly viscous liquid |
| | | $[HN_{222}][0.67Al_2Cl_7 + 0.33HSO_4]$ | Greyish white gel |
| | | $[HN_{222}][0.5Al_2Cl_7 + 0.5HSO_4]$ | Faint brown gel |
| | | $[HN_{222}][0.33Al_2Cl_7 + 0.67HSO_4]$ | Faint brown gel and solid |
| $[(1-x)AlCl_4 + xFeCl_3]$ | 7-I | $[HN_{222}]_{0.5}[0.50AlCl_4 + 0.50FeCl_3]$ | Dark red brown liquid |
| $[(1-x)AlCl_3 + xZnCl_4]$ | 8-I | $[HN_{222}][0.5AlCl_3 + 0.5ZnCl_4]$ | Viscous colorless liquid |
| | 8-II | $[HN_{222}]_{0.8}[0.6AlCl_3 + 0.4ZnCl_4]$ | Brown solid |
| | 8-III | $[HN_{222}]_{0.66}[0.67AlCl_3 + 0.33ZnCl_4]$ | Colorless solid |

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ionic liquid comprising a salt, wherein the salt comprises at least one organic cation and at least two metal halide anions with a melting point at or below about 150° C., wherein the at least two metal halide anions interact non-covalently, are present in a molar ratio from 1:1 to 1:9, and comprise a metal selected from aluminum, iron, chromium, zinc, copper, tin, titanium, palladium, zirconium, gallium, or combinations thereof, and wherein when the at least one organic cation includes triethylammonium, the ionic liquid does not include chlorocuprate.

2. The ionic liquid of claim 1, wherein the salt having the formula

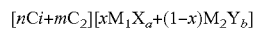

$$[nC_i+mC_2][xM_1X_a+(1-x)M_2Y_b]$$

wherein
C$_1$ and C$_2$ are cations;
M$_1$ and M$_2$ are metals;
X$_a$ and Y$_b$ are halides;
n is a number from 0 to 5;
m is a number from 0 to 5;
x is a number from 0.1 to 0.9;
wherein the sum of n+m is greater than 0; and
wherein at least one of C$_1$ and C$_2$ comprises an organic cation.

3. The ionic liquid of claim 1, wherein the at least one organic cation is selected from an alkylammonium, an arylammonium, an allylammonium, an imidazolium, a pyridinium, a phosphonium, a sulphonium, and a combination thereof.

4. The ionic liquid of claim 1, wherein the at least one organic cation is an ammonium cation of the structure $^+NR^1R^2R^3R^4$, wherein R$^1$, R$^2$, R$^3$, and R$^4$ are each independently selected from hydrogen, substituted or unsubstituted C$_{1-20}$ alkyl, substituted or unsubstituted C$_{2-20}$ alkenyl, substituted or unsubstituted C$_{2-20}$ alkynyl, substituted or unsubstituted aryl, substituted or unsubstituted C$_{1-20}$ heteroalkyl, substituted or unsubstituted C$_{2-20}$ heteroalkenyl, substituted or unsubstituted C$_{2-20}$ heteroalkynyl, substituted or unsubstituted heteroaryl, and substituted or unsubstituted carbonyl, or wherein two or more of R$^1$, R$^2$, R$^3$, and R$^4$ optionally combine to form a ring.

5. The ionic liquid of claim 4, wherein one or more of R$^1$, R$^2$, R$^3$, and R$^4$ are methyl, ethyl, propyl, or butyl.

6. The ionic liquid of claim 4, wherein two or more of R$^1$, R$^2$, R$^3$, and R$^4$ combine to form a ring, the ring including between 3 and 12 atoms.

7. The ionic liquid of claim 4, wherein two or more of R$^1$, R$^2$, R$^3$, and R$^4$ combine to form a ring, the ring including at least one double bond.

8. The ionic liquid of claim 1, wherein the at least one organic cation is a substituted or unsubstituted heteroaryl cation.

9. The ionic liquid of claim 8, wherein the heteroaryl cation is selected from a substituted or unsubstituted pyridinium cation, a substituted or unsubstituted imidazolium cation, a substituted or unsubstituted morpholinium, a substituted or unsubstituted pyrrolidinium cation, a substituted or unsubstituted quinolinium cation, a substituted or unsubstituted isoquinolinium cation, and a substituted or unsubstituted morpholinium cation.

10. The ionic liquid of claim 1, wherein the at least one organic cation is a phosphonium cation of the structure $^+PR^1R^2R^3R^4$, wherein R$^1$, R$^2$, R$^3$, and R$^4$ are each independently selected from hydrogen, substituted or unsubstituted C$_{1-20}$ alkyl, substituted or unsubstituted C$_{2-20}$ alkenyl, substituted or unsubstituted C$_{2-20}$ alkynyl, substituted or unsubstituted aryl, substituted or unsubstituted C$_{1-20}$ heteroalkyl, substituted or unsubstituted C$_{2-20}$ heteroalkenyl, substituted or unsubstituted C$_{2-20}$ heteroalkynyl, substituted or unsubstituted heteroaryl, and substituted or unsubstituted carbonyl, or wherein two or more of R$^1$, R$^2$, R$^3$, and R$^4$ optionally combine to form a ring.

11. The ionic liquid of claim 1, wherein the at least one organic cation is selected from the group consisting of dimethylammonium, trimethylammonium, tetramethylammonium, diethylammonium, triethylammonium, tetraethylammonium, dipropylammonium, tripropylammonium, and tetrapropylammmonium.

12. The ionic liquid of claim 1, wherein the at least two metal halide anions are each independently a halometallate.

13. The ionic liquid of claim 1, wherein the at least two metal halide anions are each independently selected from the group consisting of chloroaluminate, chlorozincate, chloroferrate, chlorogallate, chlorostannate, chloroindate, chlorochromate, chlorocuprate, chlorotitannate, chlorozirconate, chloropalladate, and combinations thereof.

14. The ionic liquid of claim 1, wherein the molar ratio of the at least two metal halide anions is selected from 1, 1.5, 2, 2.33, 3, 4, and 9.

15. The ionic liquid of claim 1, further comprising a solvent or a mixture of solvents.

16. A method of making an ionic liquid of claim 1, the method comprising: combining two or more metal halide containing salts, wherein the metal halide containing salts include at least one organic cation and at least two metal halide anions,
wherein the at least two metal halide anions are present in a molar ratio from 1:1 to 1:9, and comprise a metal selected from aluminum, iron, chromium, zinc, copper, tin, titanium, palladium, zirconium, gallium, or combinations thereof, and
wherein when the at least one organic cation includes triethylammonium, the ionic liquid does not include chlorocuprate.

17. The method of claim 16, wherein the organic cation is selected from alkylammonium, arylammonium, allylammonium, imidazolium, pyridiunium, phosphonium, sulphonium, and combinations thereof.

18. A catalyst comprising the ionic liquid of claim 1.

19. The ionic liquid of claim 1, wherein the at least two metal halide anions do not include chlorocuprate.

20. The ionic liquid of claim 1, wherein the at least two metal halide anions do not include copper.

* * * * *